United States Patent
Jeon et al.

(10) Patent No.: US 11,124,521 B2
(45) Date of Patent: Sep. 21, 2021

(54) CONDENSED CYCLIC COMPOUND AND ORGANIC LIGHT-EMITTING DEVICE INCLUDING THE SAME

(71) Applicant: Samsung Electronics Co., Ltd., Suwon-si (KR)

(72) Inventors: Soonok Jeon, Suwon-si (KR); Hiroshi Miyazaki, Hwaseong-si (KR); Yeonsook Chung, Seoul (KR); Kyungdoc Kim, Seoul (KR); Youngmin Nam, Seoul (KR); Myungsun Sim, Suwon-si (KR); Hasup Lee, Seoul (KR); Sooghang Ihn, Hwaseong-si (KR); Yasushi Koishikawa, Hwaseong-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 368 days.

(21) Appl. No.: 16/166,800

(22) Filed: Oct. 22, 2018

(65) Prior Publication Data
US 2019/0315760 A1    Oct. 17, 2019

(30) Foreign Application Priority Data
Apr. 11, 2018    (KR) .......................... 10-2018-0042198

(51) Int. Cl.
*H01L 51/50*    (2006.01)
*C07D 487/14*    (2006.01)
(Continued)

(52) U.S. Cl.
CPC ............. *C07D 487/14* (2013.01); *C07C 13/62* (2013.01); *C07C 43/235* (2013.01); *C07C 211/54* (2013.01); *C07C 321/30* (2013.01); *C07D 209/82* (2013.01); *C07D 307/91* (2013.01); *C07D 401/10* (2013.01); *C07D 401/14* (2013.01); *C07D 403/14* (2013.01);
(Continued)

(58) Field of Classification Search
None
See application file for complete search history.

(56) References Cited

U.S. PATENT DOCUMENTS

| 9,290,513 B2 | 3/2016 | Park et al. |
| 9,960,364 B2 | 5/2018 | Nakano et al. |
| 2015/0270496 A1 | 9/2015 | Nakano et al. |

FOREIGN PATENT DOCUMENTS

| CN | 105399748 | * 3/2016 | ............. C09K 11/06 |
| CN | 106467482 A | 3/2017 | |

(Continued)

*Primary Examiner* — Gregory D Clark
(74) *Attorney, Agent, or Firm* — Cantor Colburn LLP

(57) ABSTRACT

A condensed cyclic compound represented by Formula 1:

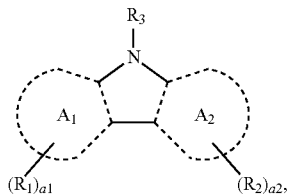

wherein, in Formula 1, groups and variables are the same as described in the specification.

19 Claims, 1 Drawing Sheet

10

| 19 |
|---|
| 15 |
| 11 |

(51) Int. Cl.
    *C07D 209/82*     (2006.01)
    *C07D 401/14*     (2006.01)
    *C07D 401/10*     (2006.01)
    *C07D 409/14*     (2006.01)
    *C07D 405/10*     (2006.01)
    *C07D 405/14*     (2006.01)
    *C07D 307/91*     (2006.01)
    *C07D 403/14*     (2006.01)
    *C07C 13/62*     (2006.01)
    *C07C 43/235*     (2006.01)
    *C07C 211/54*     (2006.01)
    *C07C 321/30*     (2006.01)
    *H01L 51/00*     (2006.01)
    *H01L 51/52*     (2006.01)
    *C07D 487/16*     (2006.01)

(52) U.S. Cl.
    CPC ......... *C07D 405/10* (2013.01); *C07D 405/14* (2013.01); *C07D 409/14* (2013.01); *C07D 487/16* (2013.01); *H01L 51/0055* (2013.01); *H01L 51/0056* (2013.01); *H01L 51/0058* (2013.01); *H01L 51/0059* (2013.01); *H01L 51/0072* (2013.01); *H01L 51/0073* (2013.01); *H01L 51/0074* (2013.01); *H01L 51/5016* (2013.01); *H01L 51/5092* (2013.01); *H01L 51/5096* (2013.01); *H01L 51/5206* (2013.01); *H01L 51/5221* (2013.01); *C07C 2603/54* (2017.05); *H01L 51/5056* (2013.01); *H01L 51/5072* (2013.01)

(56) References Cited

FOREIGN PATENT DOCUMENTS

| | | |
|---|---|---|
| CN | 106467485 A | 3/2017 |
| CN | 106467486 A | 3/2017 |
| CN | 106467526 A | 3/2017 |
| CN | 106467532 A | 3/2017 |
| KR | 10-2011-0016288 A | 1/2012 |
| KR | 10-2012-0092908 A | 8/2012 |
| KR | 10-2014-0097044 A | 8/2014 |
| KR | 10-2015-0064737 A | 6/2015 |
| KR | 10-2016-0061522 A | 6/2016 |
| WO | 2012-159213 A1 | 11/2012 |
| WO | 2014-057684 A1 | 4/2014 |
| WO | 2014057684 A1 | 4/2014 |

\* cited by examiner

10

| 19 |
|----|
| 15 |
| 11 |

CONDENSED CYCLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2018-0042198, filed on Apr. 11, 2018, in the Korean Intellectual Property Office, and all the benefits accruing therefrom under 35 U.S.C. § 119, the content of which is incorporated herein in its entirety by reference.

BACKGROUND

1. Field

One or more embodiments relate to a condensed cyclic compound and an organic light-emitting device including the same.

2. Description of the Related Art

Organic light-emitting devices (OLEDs) are self-emission devices, which have wide viewing angles, high contrast ratios, short response times, as well as excellent characteristics in terms of brightness, driving voltage, and response speed, and which produce full-color images.

In an example, an organic light-emitting device includes an anode, a cathode, and an organic layer disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons transit from an excited state to a ground state, thereby generating light.

Various types of organic light emitting devices are known. However, there still remains a need in OLEDs having low driving voltage, high efficiency, high brightness, and long lifespan.

SUMMARY

One or more embodiments include a condensed cyclic compound and an organic light-emitting device including the same.

Additional aspects will be set forth in part in the description which follows and, in part, will be apparent from the description, or may be learned by practice of the presented embodiments.

An aspect provides a condensed cyclic compound represented by Formula 1 below:

Formula 1

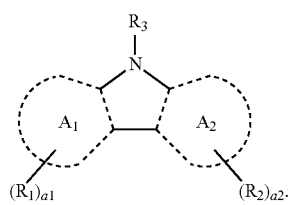

In Formula 1, $A_1$ and $A_2$ may each be a carbazole group, $R_1$ to $R_3$ may each independently be selected from hydrogen, deuterium, —F, —Cl, —Br, —I, a hydroxyl group, a cyano group, a cyano group-containing group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), wherein at least one of $R_1$ to $R_3$ is a cyano group or a cyano group-containing group, when at least two of $R_1$ to $R_3$ are a cyano group-containing group, $R_1$ to $R_3$ may be identical to or different from each other, a1 and a2 may each independently be an integer of 1 to 7, when a1 is two or more, two or more groups $R_1$ may be identical to or different from each other, when a2 is two or more, two or more groups $R_2$ may be identical to or different from each other, the number of cyano groups included in the condensed cyclic compound represented by Formula 1 may be 1 to 10, at least one substituent of the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $-Si(Q_{11})(Q_{12})(Q_{13})$, $-N(Q_{14})(Q_{15})$, and $-B(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, $-CD_3$, $-CD_2H$, $-CDH_2$, $-F$, $-Cl$, $-Br$, $-I$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $-Si(Q_{21})(Q_{22})(Q_{23})$, $-N(Q_{24})(Q_{25})$, and $-B(Q_{26})(Q_{27})$; and $-Si(Q_{31})(Q_{32})(Q_{33})$, $-N(Q_{34})(Q_{35})$, and $-B(Q_{36})(Q_{37})$, and $Q_1$ to $Q_7$, $Q_{11}$ to $Q_{17}$, $Q_{21}$ to $Q_{27}$, and $Q_{31}$ to $Q_{37}$ may each independently be selected from hydrogen, deuterium, $-F$, $-Cl$, $-Br$, $-I$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

Another aspect provides an organic light-emitting device including:

a first electrode;

a second electrode facing the first electrode; and an organic layer disposed between the first electrode and the second electrode, wherein the organic layer includes an emission layer, and wherein the organic layer includes at least one condensed cyclic compound described above.

BRIEF DESCRIPTION OF THE DRAWING

These and/or other aspects will become apparent and more readily appreciated from the following description of the embodiments, taken in conjunction with the FIGURE which is a schematic cross-sectional view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

An aspect of the present disclosure provides a condensed cyclic compound represented by Formula 1 illustrated below:

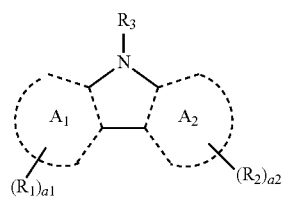

Formula 1

In Formula 1, $A_1$ and $A_2$ may each independently be a carbazole group.

In Formula 1, $R_1$ to $R_3$ may each independently be selected from hydrogen, deuterium, —F, —Cl, —Br, —I, a hydroxyl group, a cyano group, a cyano group-containing group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si$(Q_1)(Q_2)$$(Q_3)$, —N$(Q_4)(Q_5)$, and —B$(Q_6)(Q_7)$, wherein at least one selected from $R_1$ to $R_3$ may be a cyano group or a cyano group-containing group, and when two or more of $R_1$ to $R_3$ each includes a cyano group-containing group, two or more of groups $R_1$ to $R_3$ may be identical to or different from each other.

In the present specification, "a cyano group-containing group" may refer to a substitute of the $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, or the substituted monovalent non-aromatic condensed heteropolycyclic group, each substituted with a cyano group. In addition, a substituent consisting of only "a cyano group", i.e., "a cyano group" does not refer to "a cyano group-containing group".

In an embodiment, the cyano group-containing group may be a group represented by Formula 2:

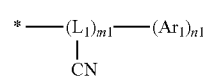

Formula 2

In Formula 2, $L_1$ may be a $C_5$-$C_{30}$ carbocyclic group or a $C_1$-$C_{30}$ heterocyclic group, m may be a integer of 1 to 5, wherein, when m1 is two or more, two or more of groups $L_1$ may be identical to or different from each other, $Ar_1$ may be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si$(Q_1)(Q_2)$$(Q_3)$, —N$(Q_4)(Q_5)$, and —B$(Q_6)(Q_7)$, n1 may be an integer of 1 to 4, wherein, when n1 is two or more, two or more of groups $Ar_1$ may be identical to or different from each other, and

* indicates a binding site to a neighboring atom.

In an embodiment, $L_1$ in Formula 2 may be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

For example, $L_1$ in Formula 2 may be selected from a benzene group, a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a carbazole group, a benzocarbazole group, a dibenzofuran group, and a dibenzothiophene group.

For example, $L_1$ in Formula 2 may be a benzene group, but embodiments of the present disclosure are not limited thereto.

For example, the group represented by Formula 2 may be selected from Formulae 3-1 to 3-9:

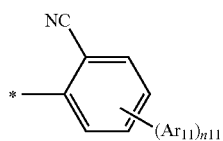

3-1

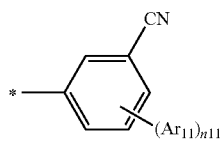

3-2

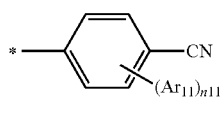

3-3

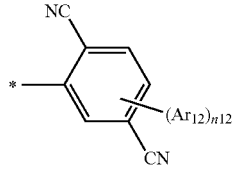

3-4

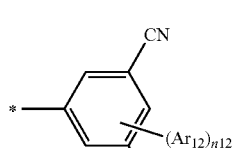

3-5

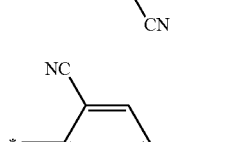

3-6

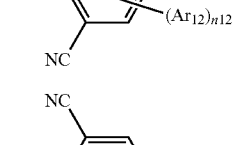

3-7

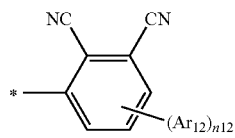

3-8

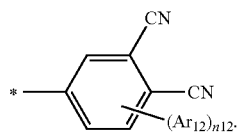

3-9

In Formulae 3-1 to 3-9,
$Ar_{11}$ and $Ar_{12}$ may respectively be the same as $Ar_1$,
$n_{11}$ may be an integer of 1 to 4,
$n_{12}$ may be integer of 1 to 3,
$Ar_1$ in Formula 2 may be selected from:
hydrogen, deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyrimidoindolyl, a benzofuropyrimidinyl group, a benzothienopyrimidinyl group, a phenoxazinyl group, a pyridobenzooxazinyl group, and a pyridobenzothiazinyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyrimidobenzooxaxinyl group, and a pyrimidobenzothiazinyl group, each substituted with at least one selected from deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a biphenyl group, a terphenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —Si($Q_{31}$)($Q_{32}$)($Q_{33}$), —N($Q_{34}$)($Q_{35}$), and —B($Q_{36}$)($Q_{37}$); and —Si($Q_1$)($Q_2$)($Q_3$), —N($Q_4$)($Q_5$), and —B($Q_6$)($Q_7$), and $Q_1$ to $Q_7$ and $Q_{31}$ to $Q_{37}$ may each independently be selected from hydrogen, a $C_1$-$C_{20}$ alkyl group, a $C_1$-$C_{20}$ alkoxy group, a phenyl group, a biphenyl group, a terphenyl group, a naphthyl group, a fluorenyl group, a carbazolyl group, a dibenzofuranyl group, and a dibenzothiophenyl group.

In one or more embodiments, in Formula 2, $Ar_1$ may be selected from:

hydrogen, deuterium, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, a cyano group, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group; and a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group, each substituted with at least one selected from deuterium, a $C_1$-$C_{20}$ alkyl group, a $C_1$-$C_{20}$ alkoxy group, a phenyl group, a biphenyl group, a terphenyl group, and a naphthyl group.

For example, $Ar_1$ may be selected from hydrogen, deuterium, a $C_1$-$C_{20}$ alkyl group, and a $C_1$-$C_{20}$ alkoxy group; and a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group, each substituted with at least one selected from deuterium, a $C_1$-$C_{20}$ alkyl group, a $C_1$-$C_{20}$ alkoxy group, a phenyl group, a biphenyl group, a terphenyl group, and a naphthyl group, but embodiments of the present disclosure are not limited thereto.

In an embodiment, in Formula 1, $R_1$ to $R_3$ each independently be selected from:

a cyano group-containing group, hydrogen, deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, a pyrimidinyl group, a pyrazinyl group, a pyridazinyl group, and a triazinyl group;

a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyridimidinyl group, and an imidazopyridinyl group; and a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyridimidinyl group, and an imidazopyridinyl group, each substituted with at least one selected from deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

For example, $R_1$ to $R_3$ may each independently be selected from:

a cyano group-containing group, hydrogen, deuterium, —F, —Cl, —Br, —I, $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group; and a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group, each substituted with at least one selected from deuterium, a $C_1$-$C_{20}$ alkyl group, a $C_1$-$C_{20}$ alkoxy group, a phenyl group, a biphenyl group, a terphenyl group, and a naphthyl group.

For example, $R_1$ to $R_3$ may each independently be selected from:

a cyano group-containing group, hydrogen, deuterium, —F, —Cl, —Br, —I, $C_1$-$C_{20}$ alkyl group, and a $C_1$-$C_{20}$ alkoxy group; and a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group, each substituted with at least one selected from deuterium, a $C_1$-$C_{20}$ alkyl group, a $C_1$-$C_{20}$ alkoxy group, a phenyl group, a biphenyl group, a terphenyl group, and a naphthyl group, but embodiments of the present disclosure are not limited thereto.

In Formula 1, a1 and a2 may each independently be an integer of 1 to 7, wherein, when a1 is two or more, two or more of groups $R_1$ may be identical to or different from each other, and when a2 is two or more, two or more of groups $R_2$ may be identical to or different from each other.

The number of the cyano group included in the condensed cyclic compound represented by Formula 1 may be selected from 1 to 10.

The number of the cyano group included in the condensed cyclic compound represented by Formula 1 may be 1 or 2.

In an embodiment, the condensed cyclic compound represented by Formula 1 may be a compound represented by one selected from Formulae 1-1 to 1-21:

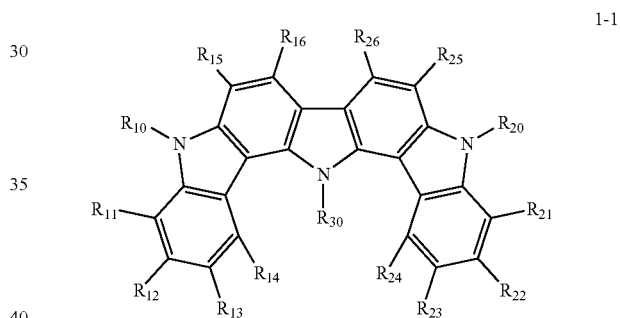

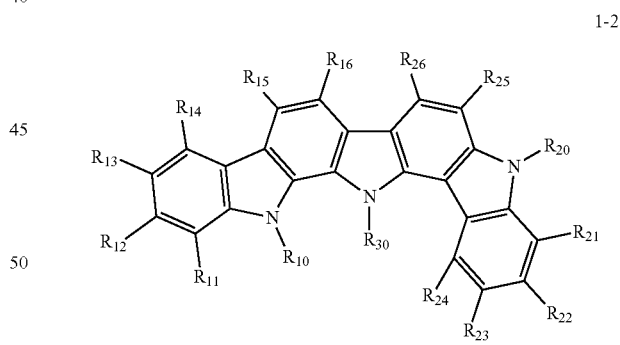

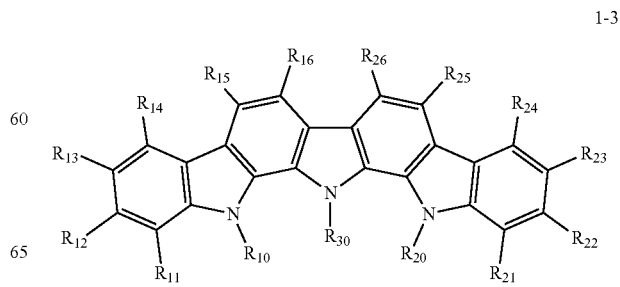

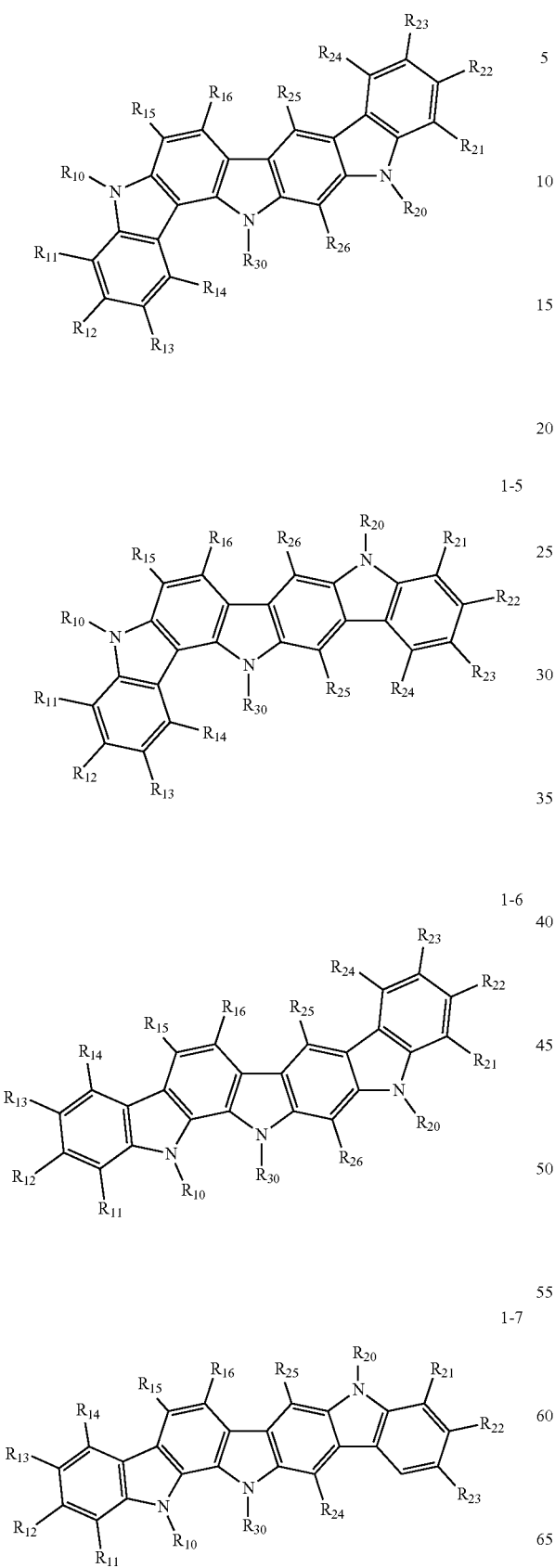
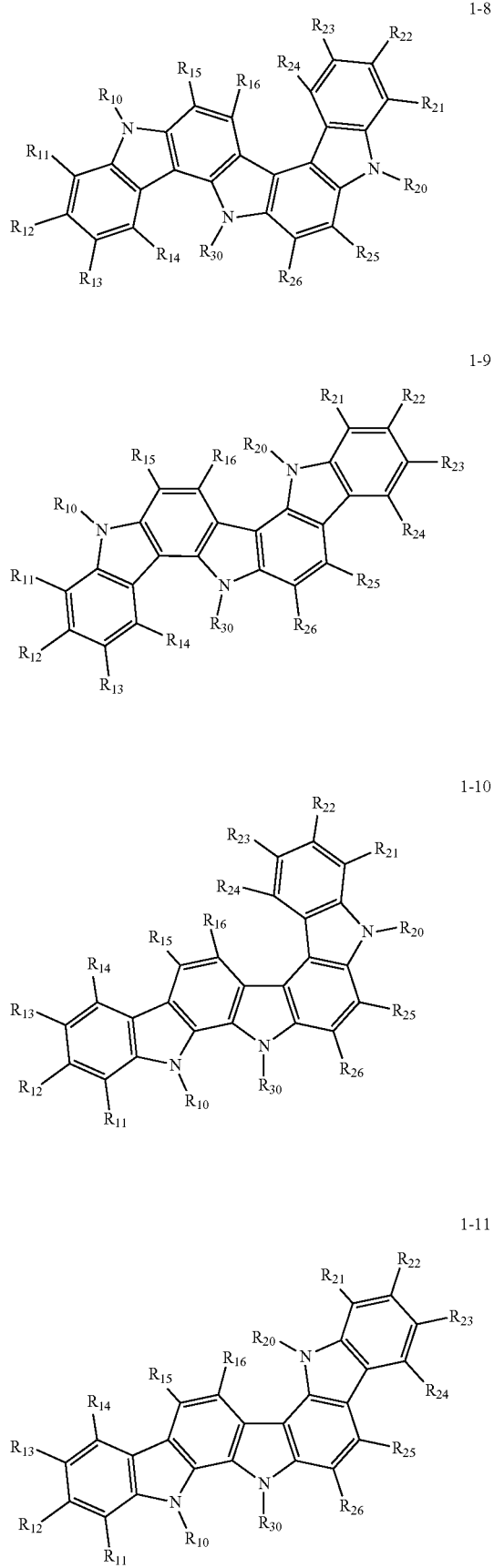

-continued
1-12
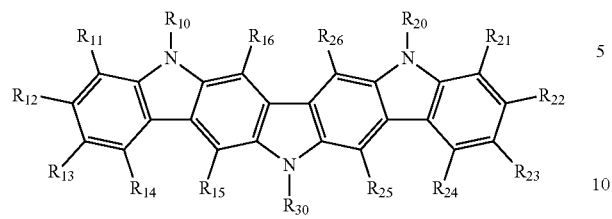
1-13
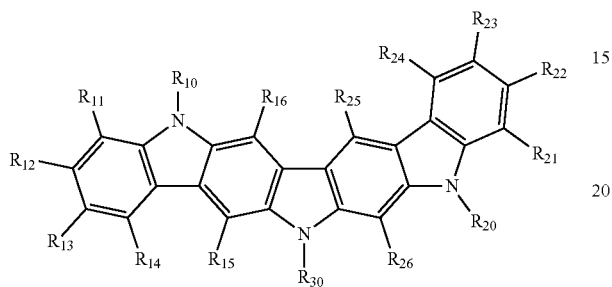
1-14
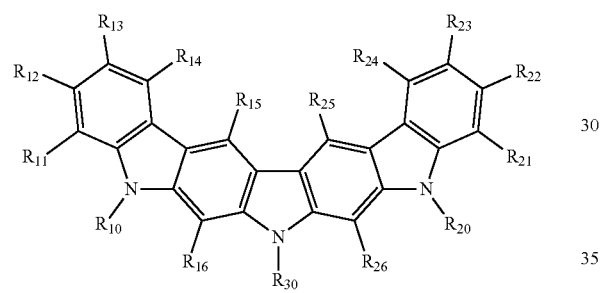
1-15
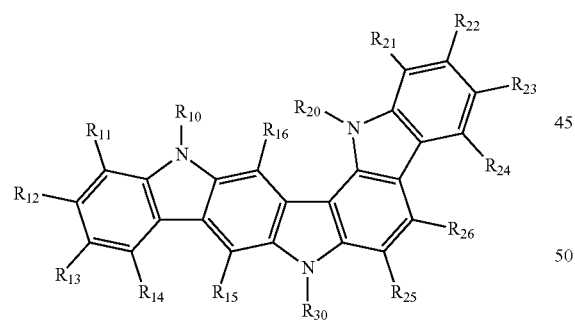
1-16
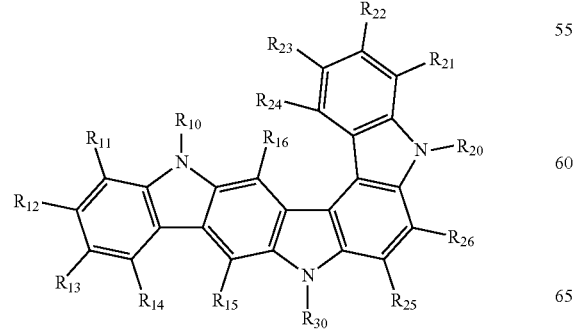
-continued
1-17
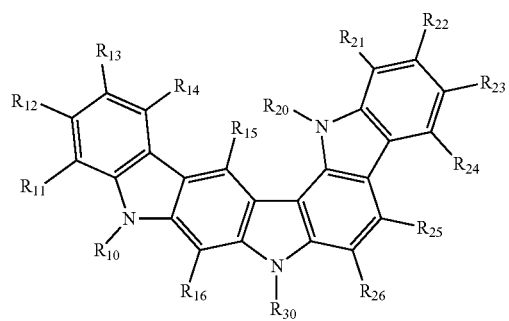
1-18
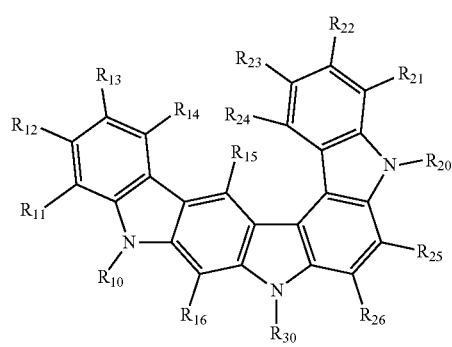
1-19
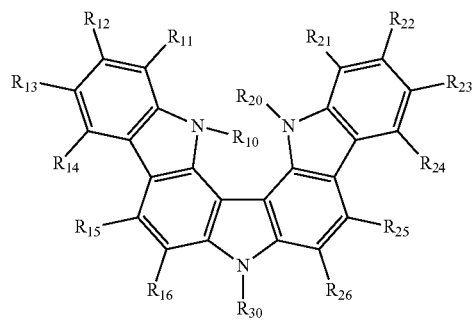
1-20
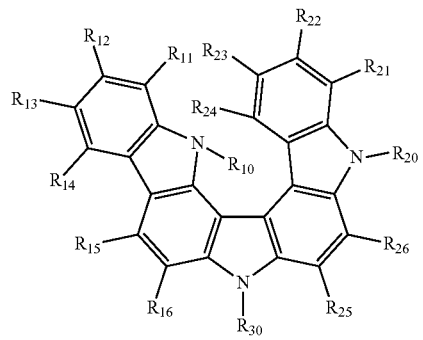

-continued

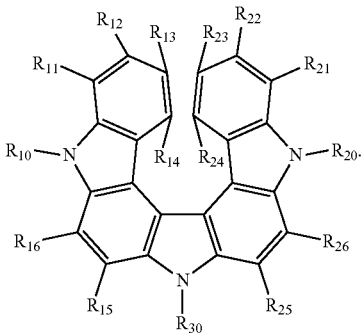

1-21

In Formulae 1-1 to 1-21, $R_{10}$ to $R_{16}$ may respectively be the same as $R_1$, $R_{20}$ to $R_{26}$ may respectively be the same as $R_2$, $R_{30}$ may be the same as $R_3$, at least one of $R_{10}$ to $R_{16}$, $R_{20}$ to $R_{26}$, and $R_{30}$ may be a cyano group or a cyano group-containing group.

In an embodiment, at least one of $R_{10}$, $R_{20}$, and $R_{30}$ may be a cyano group-containing group, or at least one of $R_{11}$ to $R_{16}$ and $R_{21}$ to $R_{26}$ may be a cyano group.

In an embodiment, the condensed cyclic compound represented by Formula 1 may be a compound represented by Formula 1-1.

In an embodiment, at least one of $R_{10}$ to $R_{14}$, $R_{20}$ to $R_{24}$, and $R_{30}$ in Formulae 1-1 to 1-21 may be a cyano group or a cyano group-containing group.

In an embodiment, at least one of $R_{10}$, $R_{20}$, and $R_{30}$ in Formulae 1-1 to 1-21 may be a cyano group-containing group.

In one or more embodiments, in Formulae 1-1 to 1-21, (i) $R_{10}$ and $R_{20}$ may each independently be a cyano group-containing group, (ii) $R_{10}$ and $R_{30}$ may each independently be a cyano group-containing group, (iii) one of $R_{11}$ to $R_{14}$ and $R_{21}$ to $R_{24}$ may be a cyano group, and one of $R_{10}$ to $R_{30}$ may be a cyano group-containing group, or (iv) one of $R_{15}$, $R_{16}$, $R_{25}$, and $R_{26}$ may be a cyano group, and one of $R_{10}$ to $R_{30}$ may be a cyano group-containing group.

In one or more embodiments, in Formulae 1-1 to 1-21, (i) $R_{10}$ and $R_{20}$ may each independently be a cyano group-containing group, (ii) $R_{10}$ and $R_{30}$ may each independently be a cyano group-containing group, (iii) one of $R_{11}$ to $R_{14}$; and $R_{10}$ may each independently be a cyano group-containing group, or (iv) one of $R_{21}$ to $R_{24}$; and $R_{20}$ may each independently be a cyano group-containing group.

At least one substituent of the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_{60}$ alkoxy group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{14})(Q_{15})$, and —$B(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{24})(Q_{25})$, and —$B(Q_{26})(Q_{27})$; and —$Si(Q_{31})(Q_{32})(Q_{33})$, —$N(Q_{34})(Q_{35})$, and —$B(Q_{36})(Q_{37})$, and $Q_1$ to $Q_7$, $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In an embodiment, the condensed cyclic compound represented by Formula 1 may be selected from Compounds 1 to 112, but embodiments of the present disclosure are not limited thereto:

1

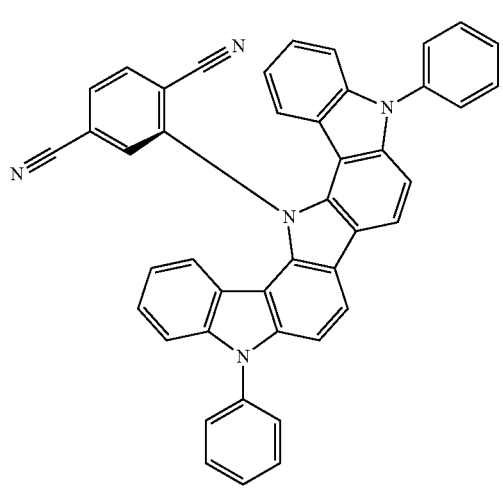

2

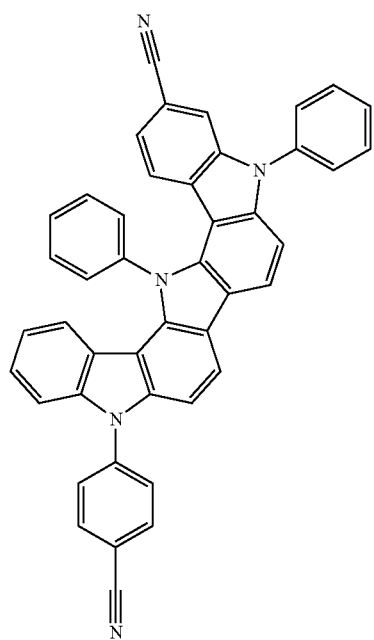

-continued

3

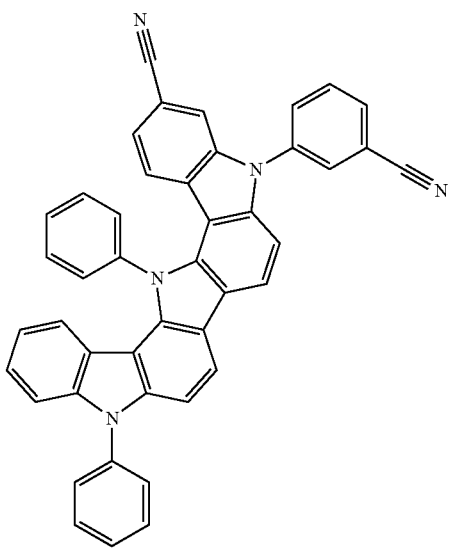

4

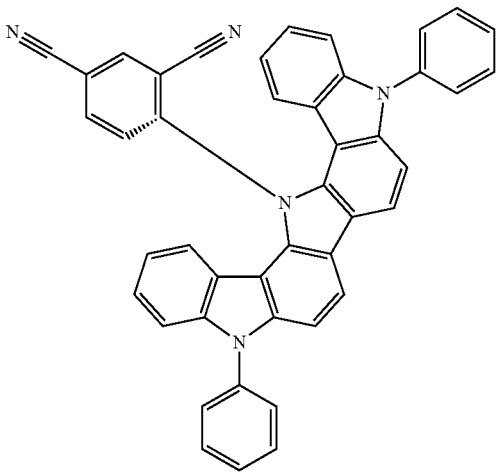

5

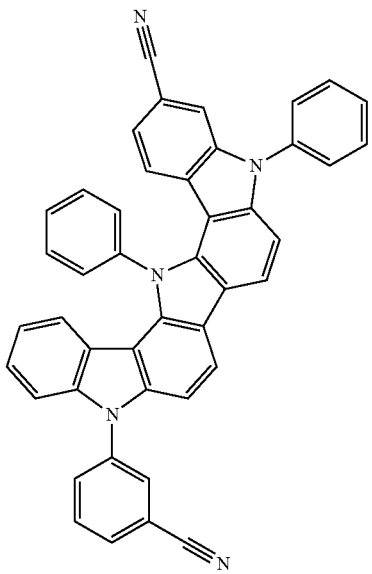

-continued
6
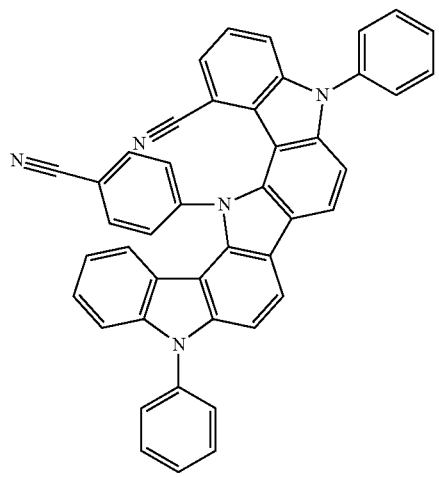
5
-continued
9
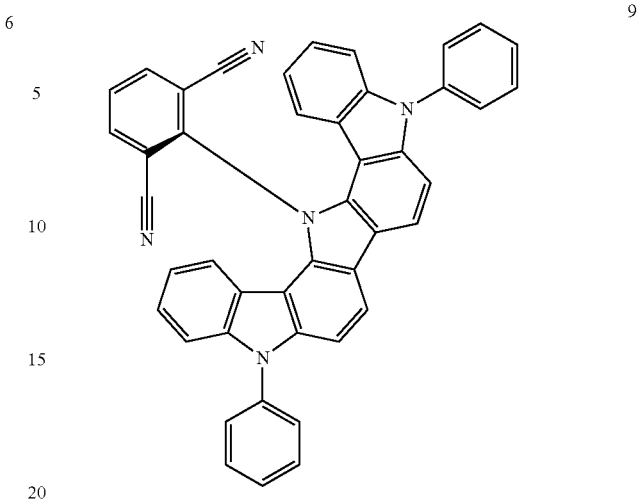
7
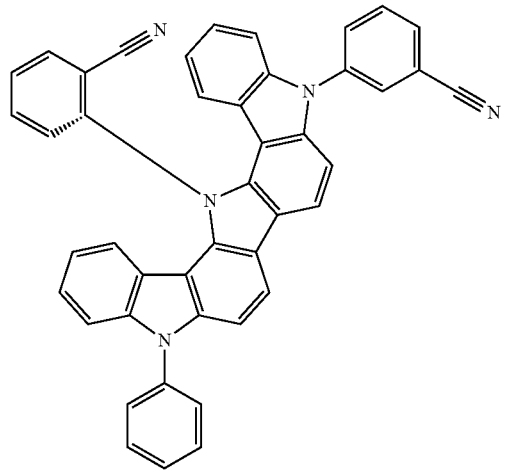
10
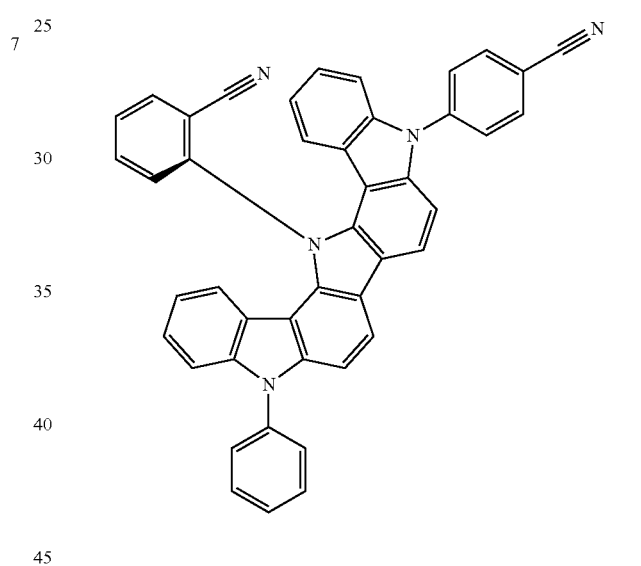
8
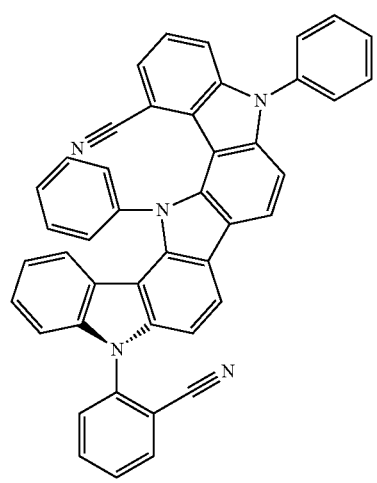
11
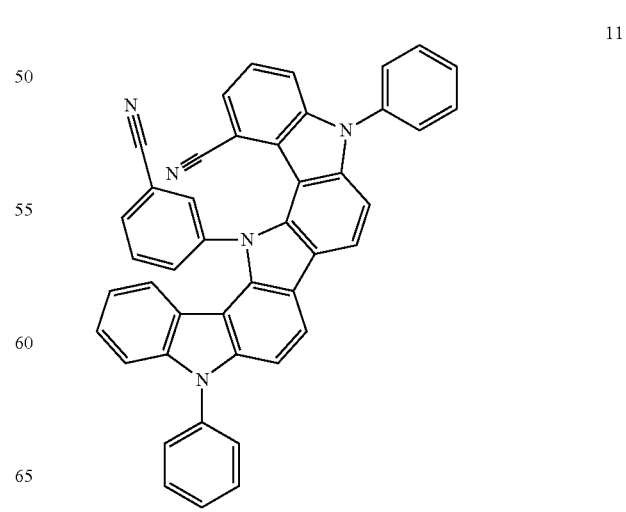

12
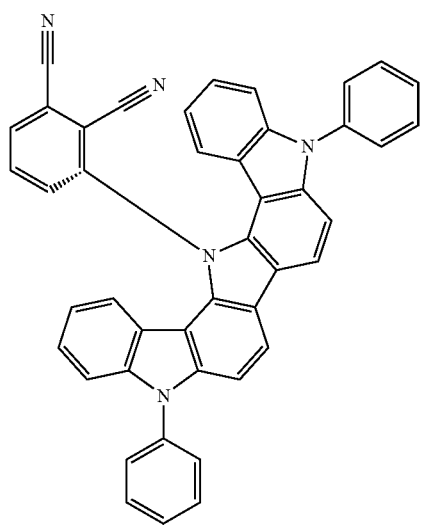
13
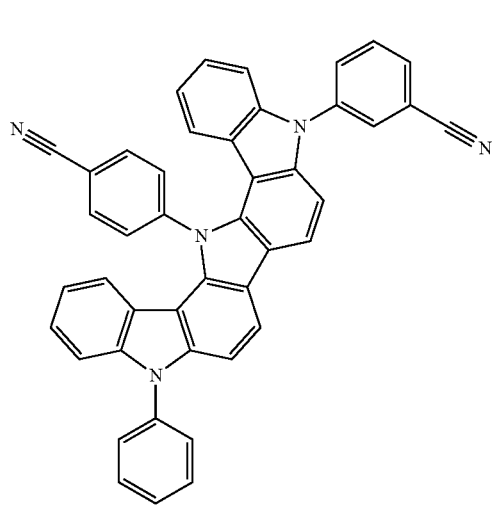
14
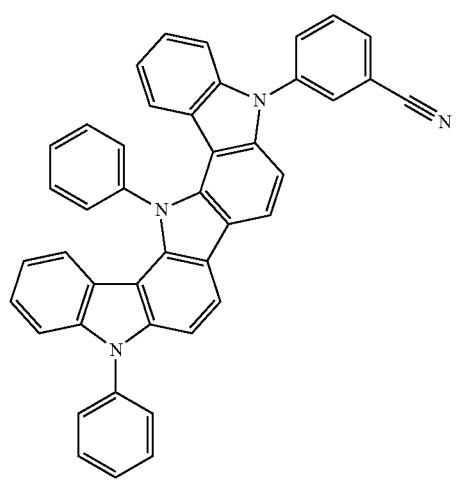
15
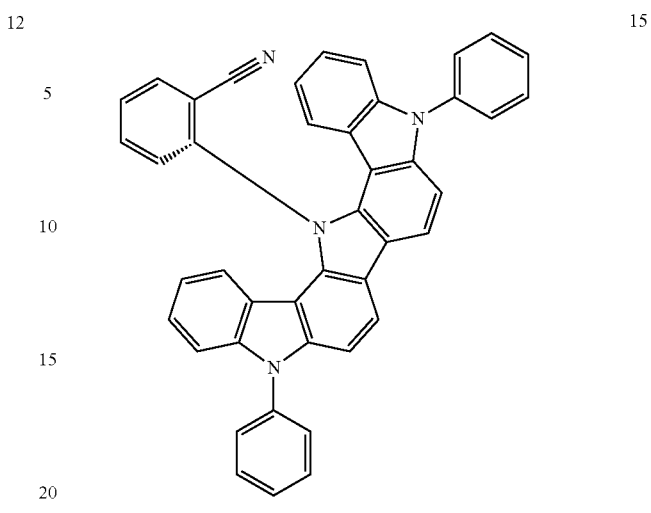
16
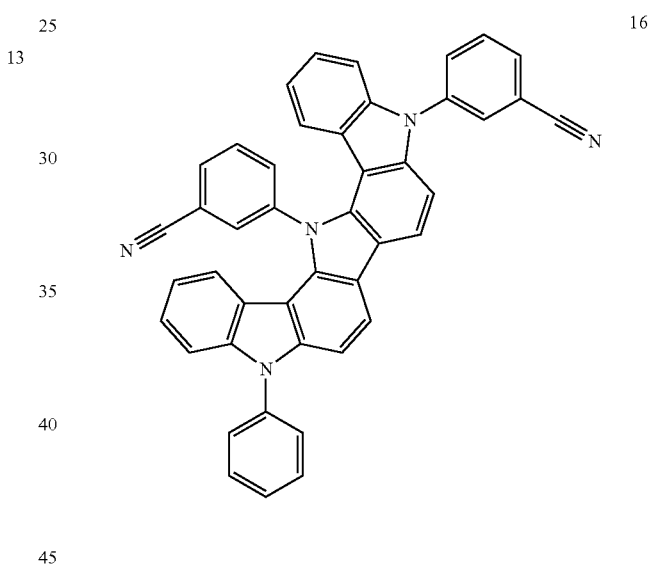
17

18
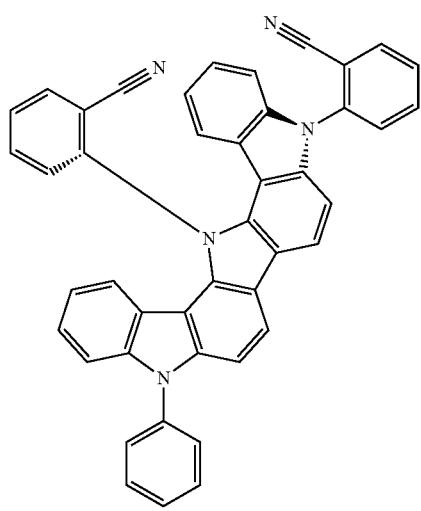
19
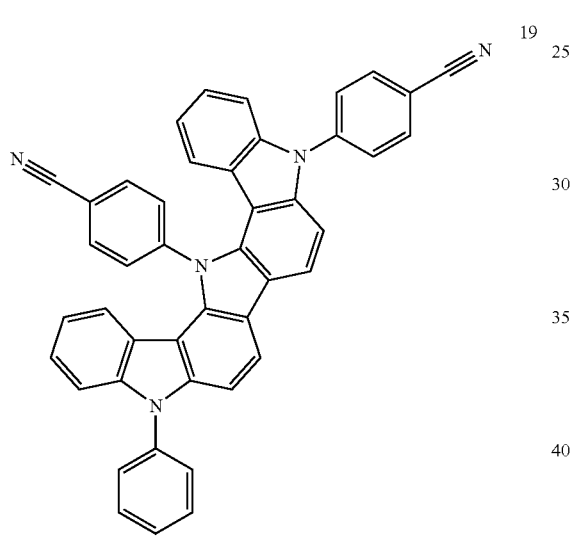
20
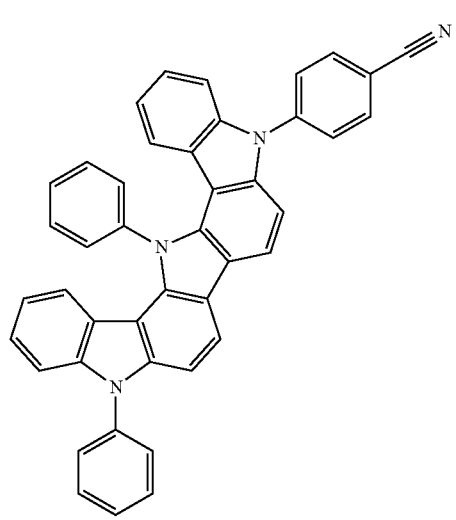
21
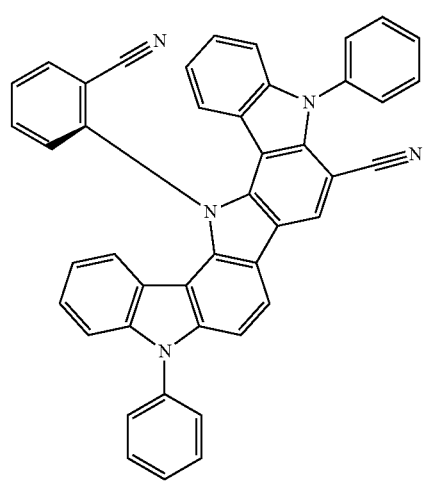
22
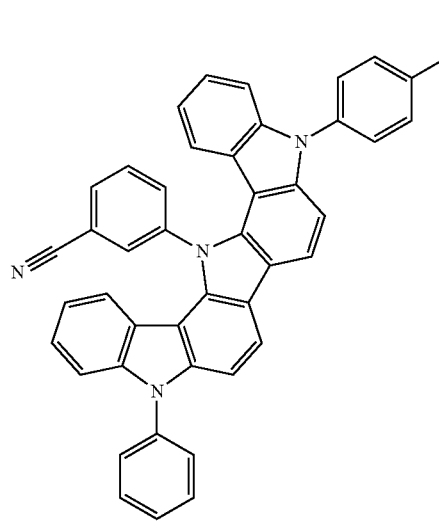
23
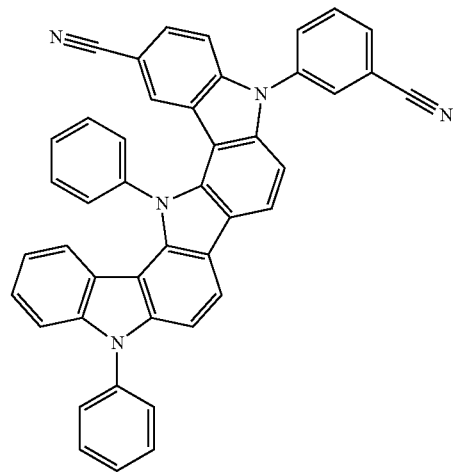

24
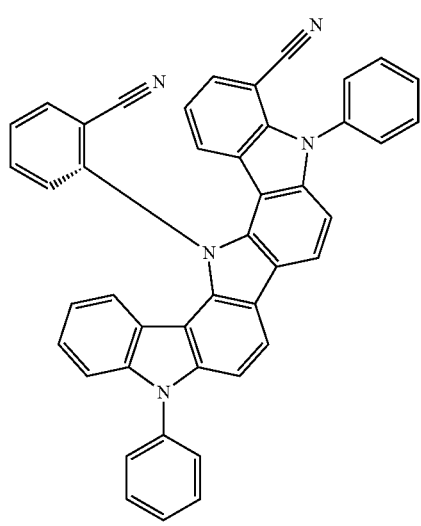
25
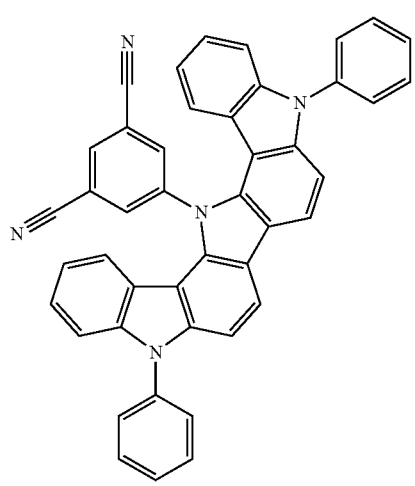
26
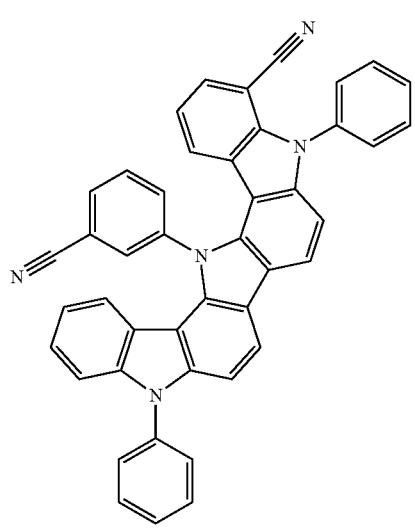
27
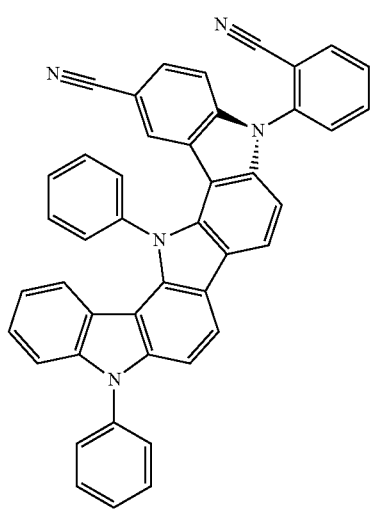
28
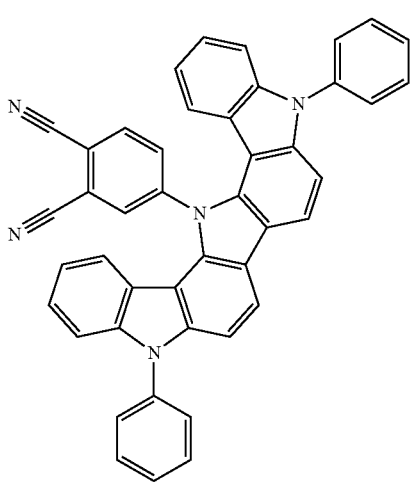
29
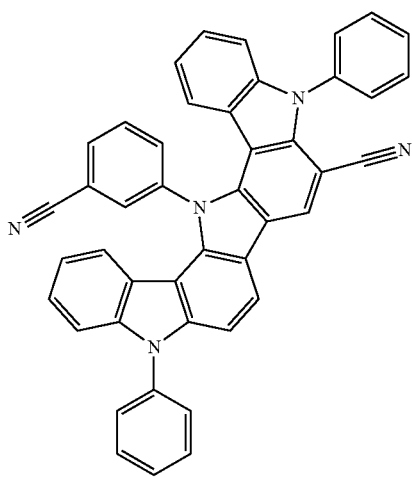

29
-continued
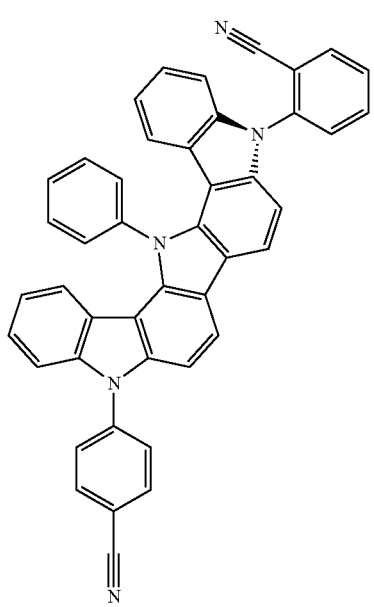
30
-continued
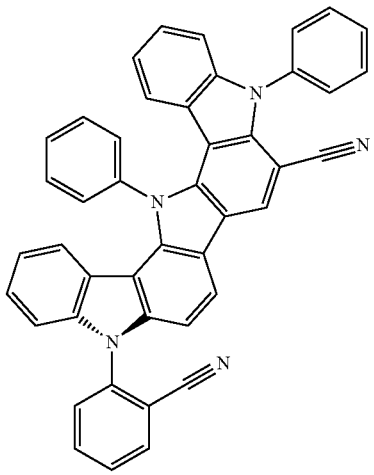
31
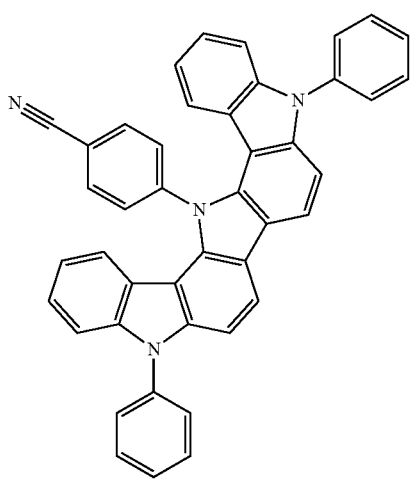
32
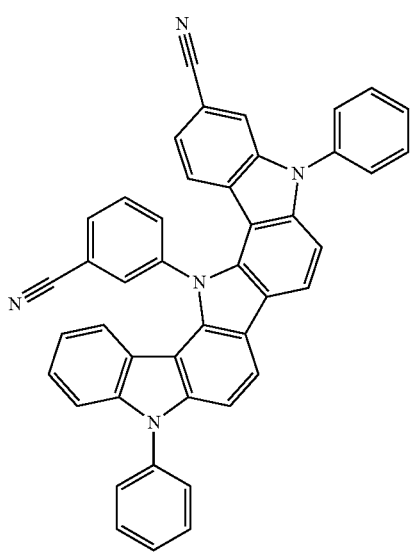
33
34
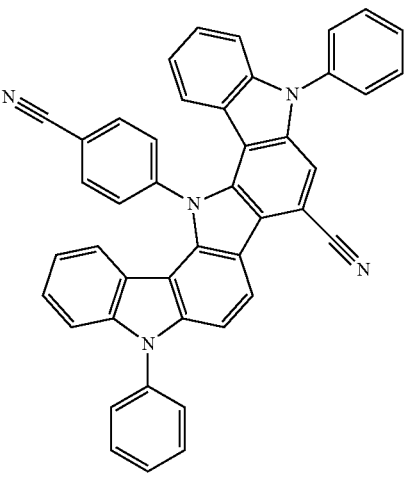
35

36
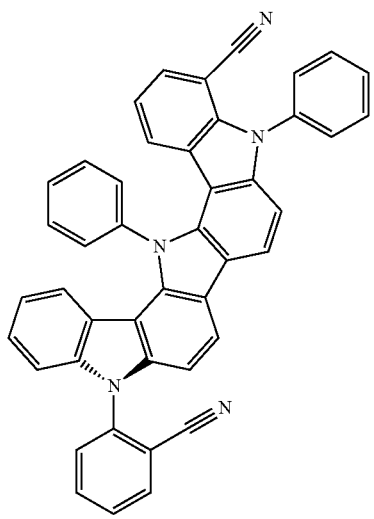
37
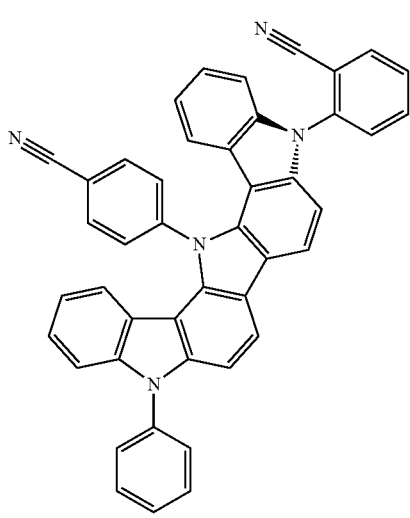
38
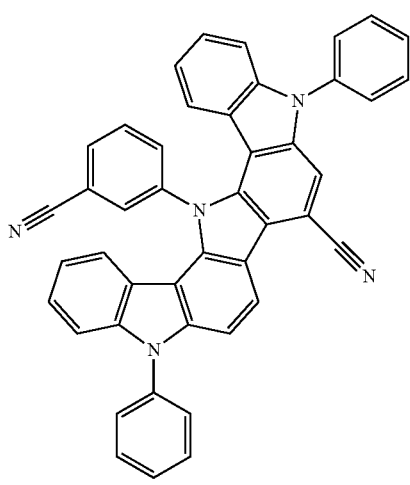
39
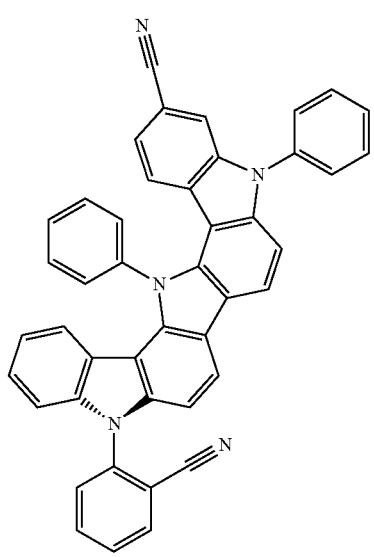
40
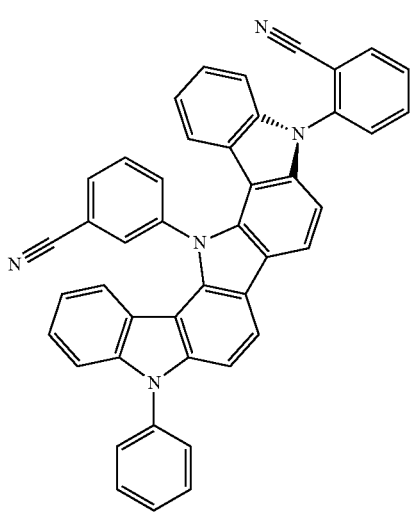
41
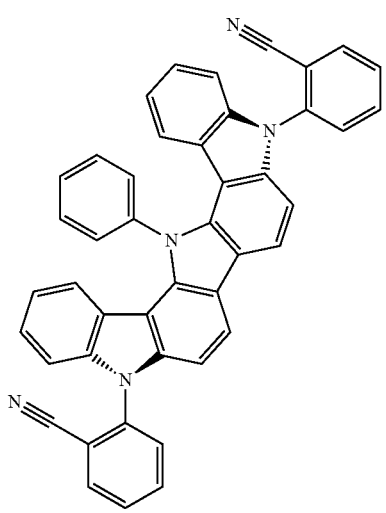

42
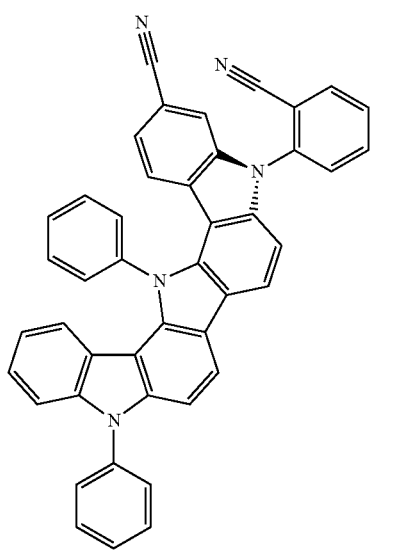
43
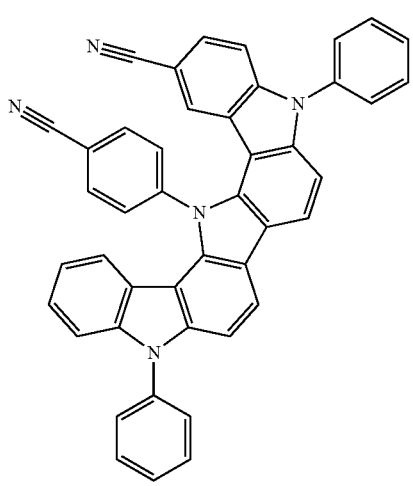
44
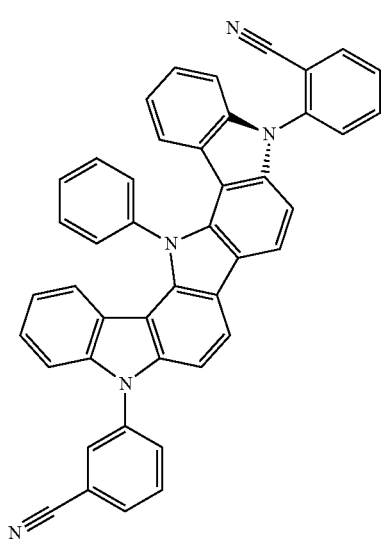
45
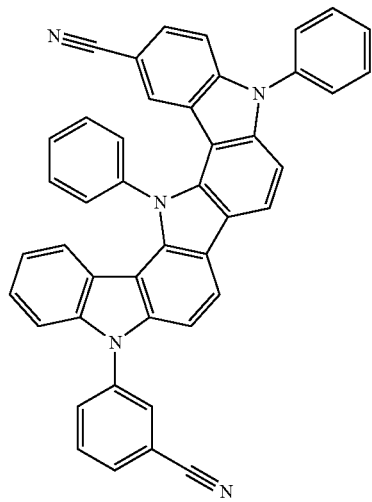
46
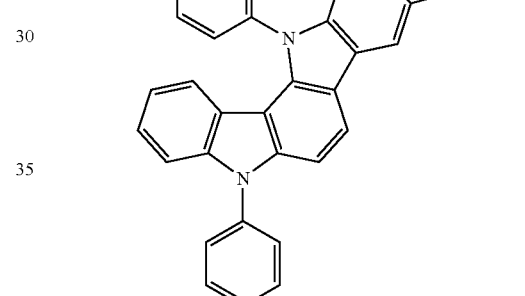
47
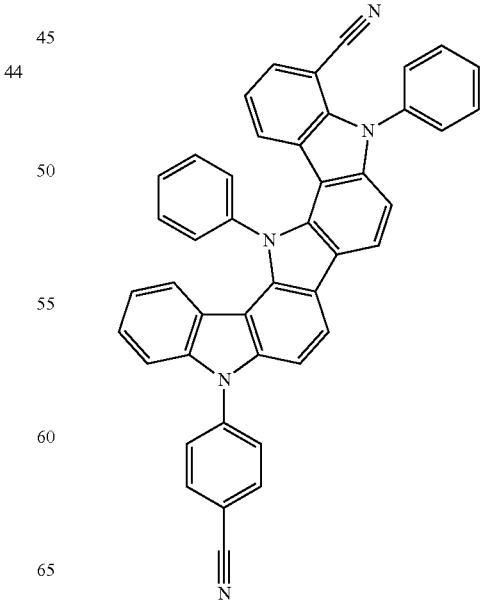

48
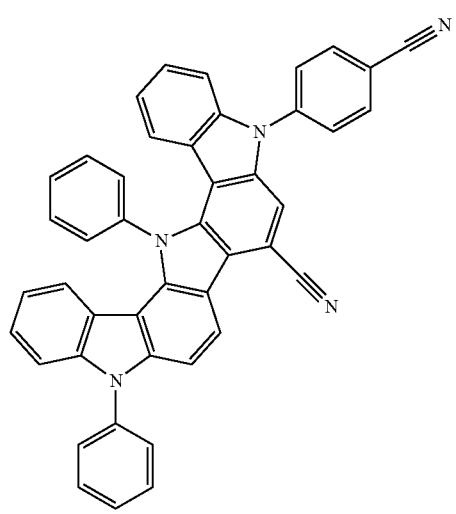
49
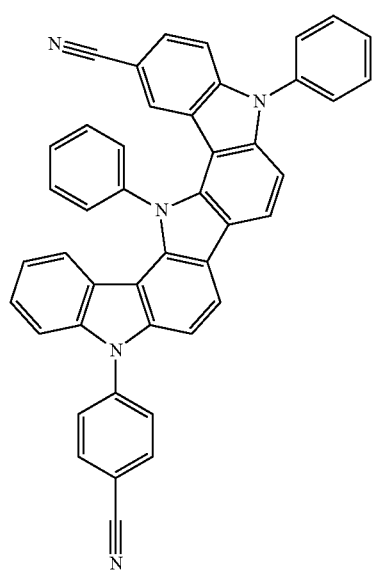
50
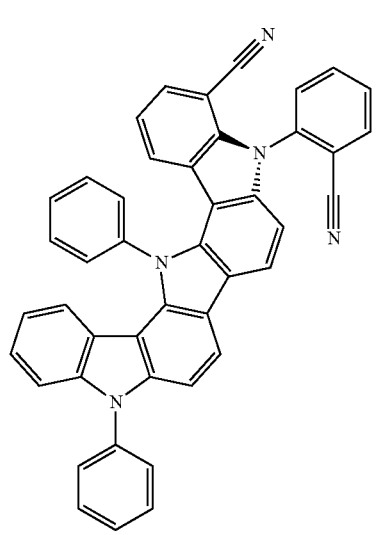
51
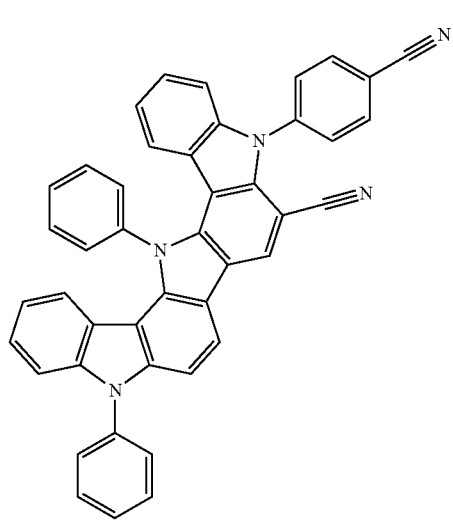
52
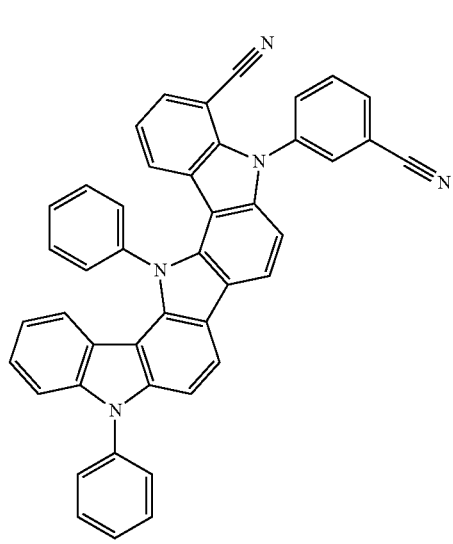
53
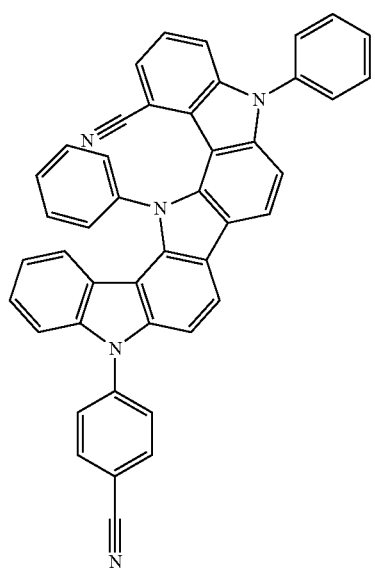

54
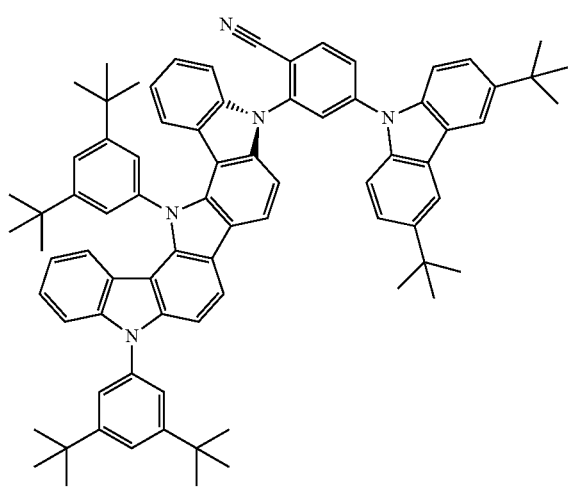
56
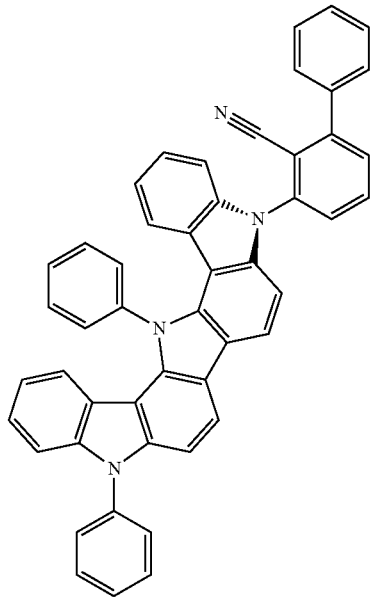
55
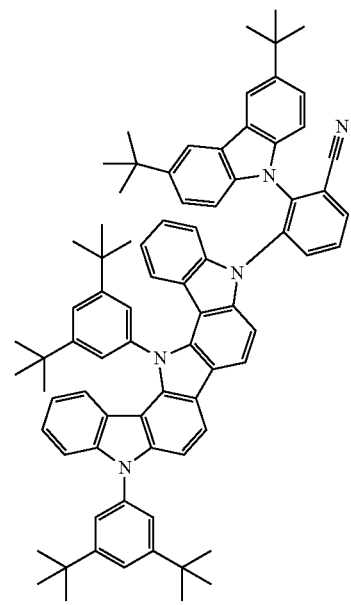
57
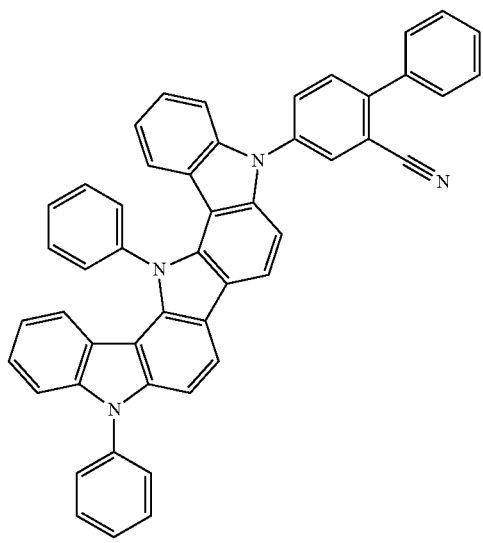

58
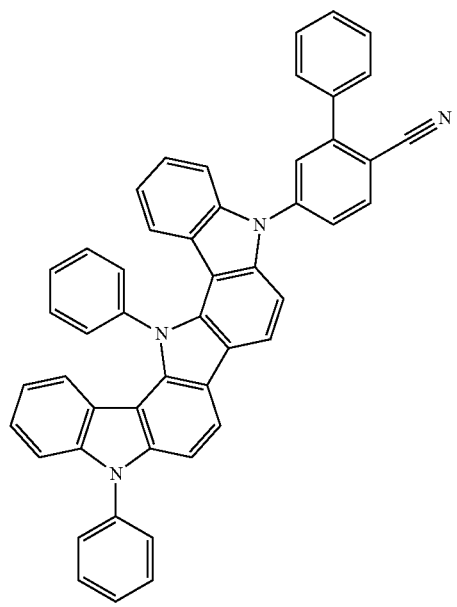
59
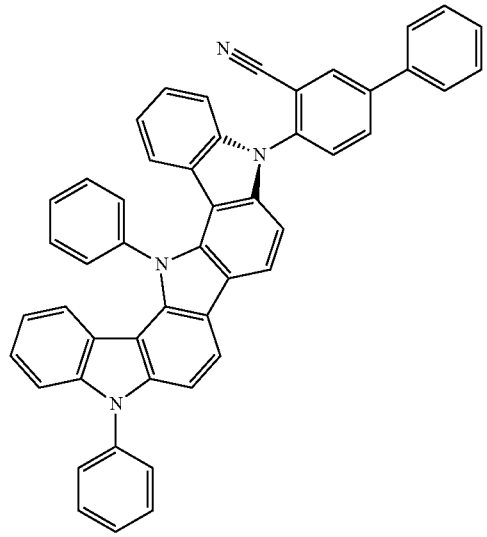
60
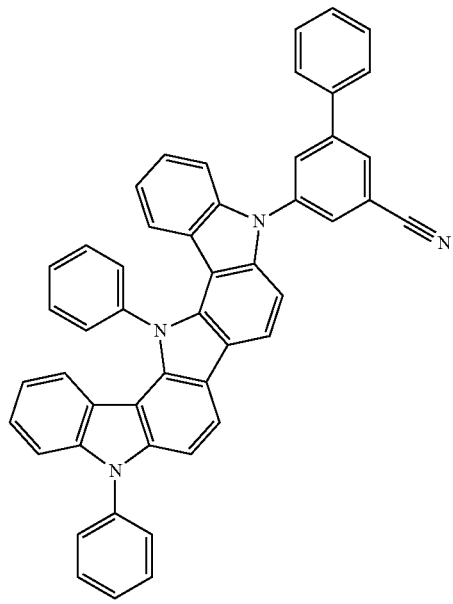
61
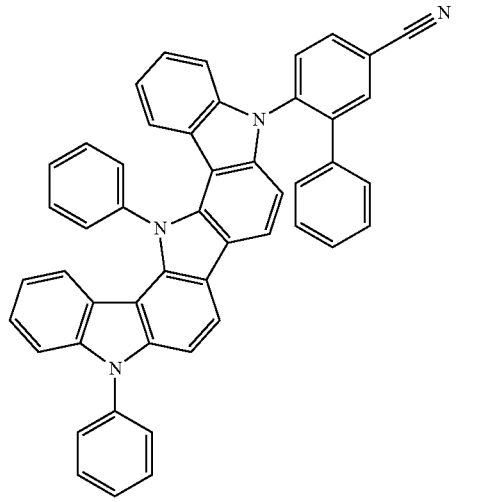
62
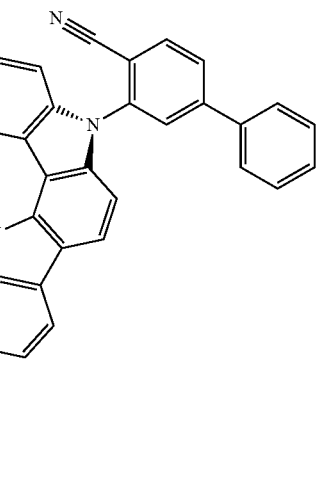

63
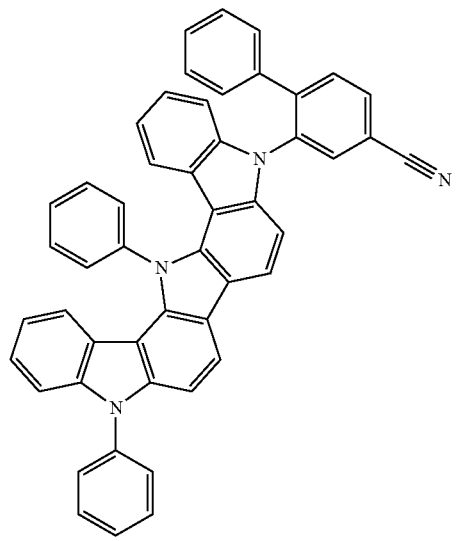
65
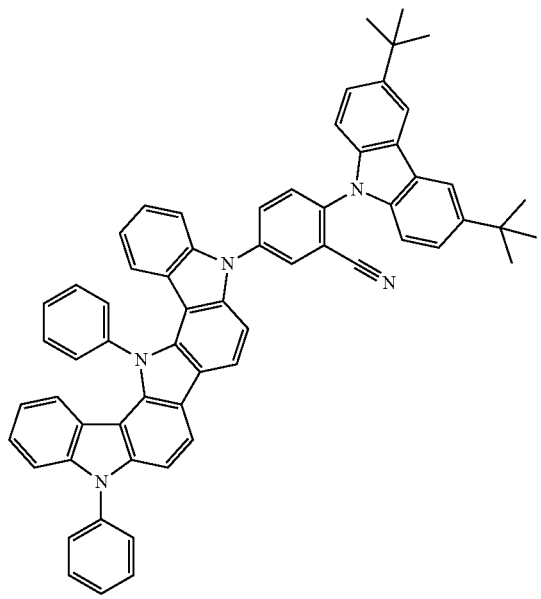
64
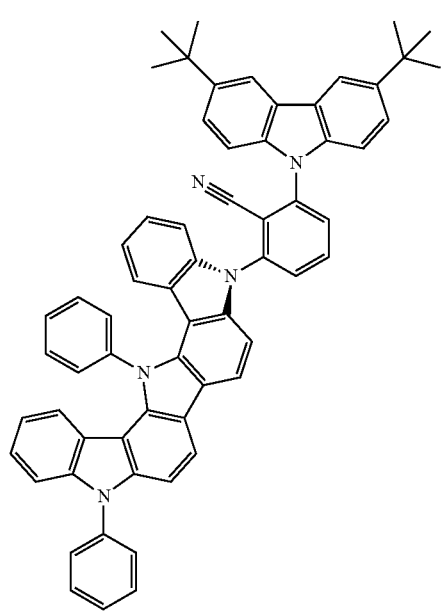
66
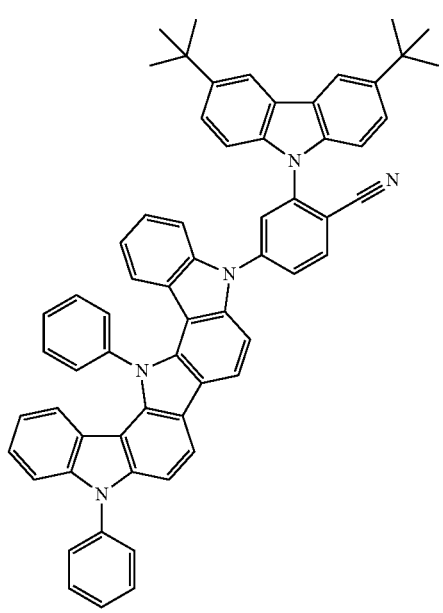

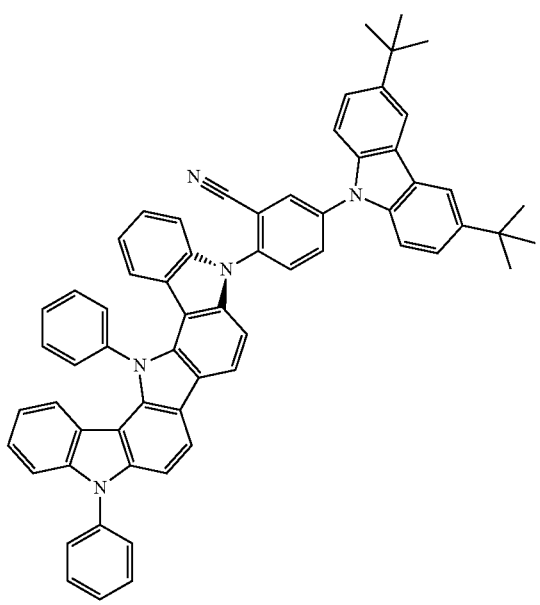
67
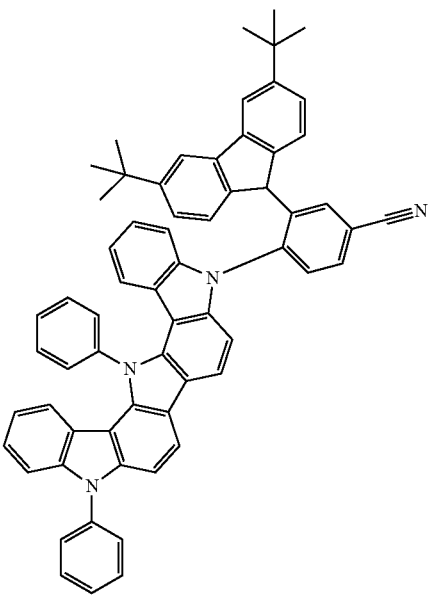
69
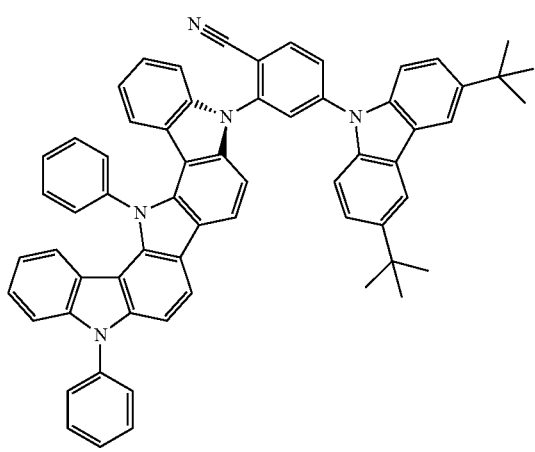
70
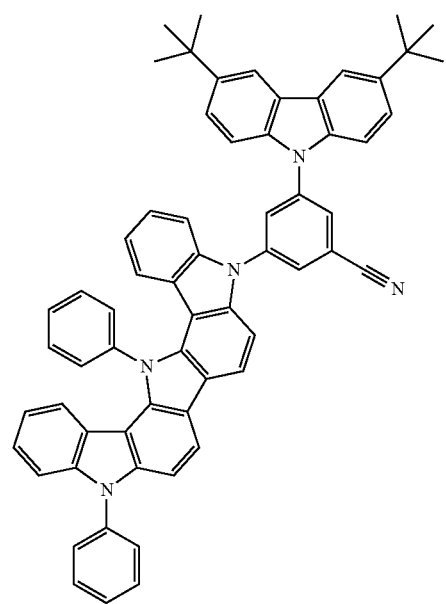
68
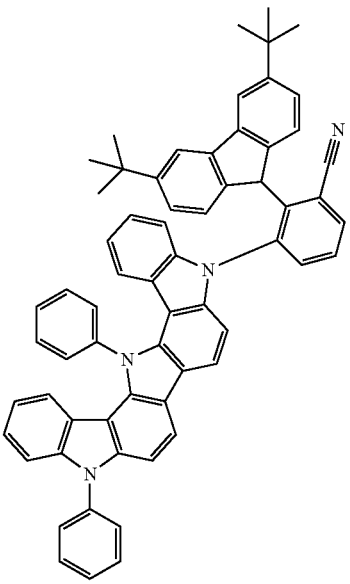
71

72
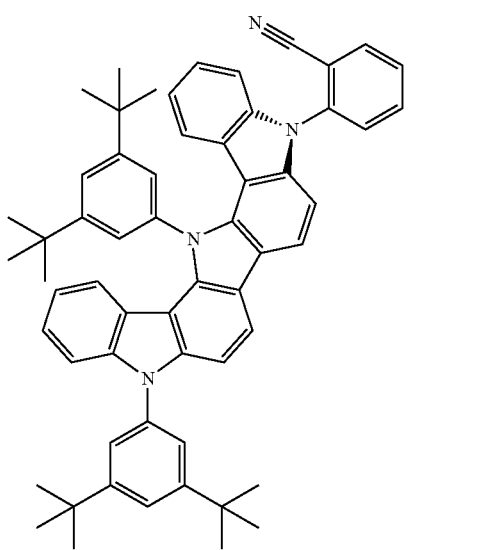
73
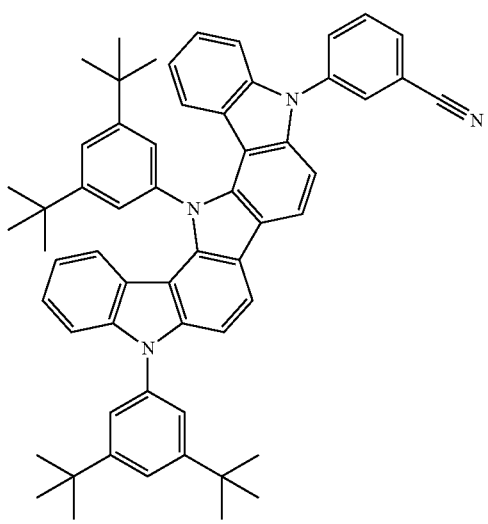
74
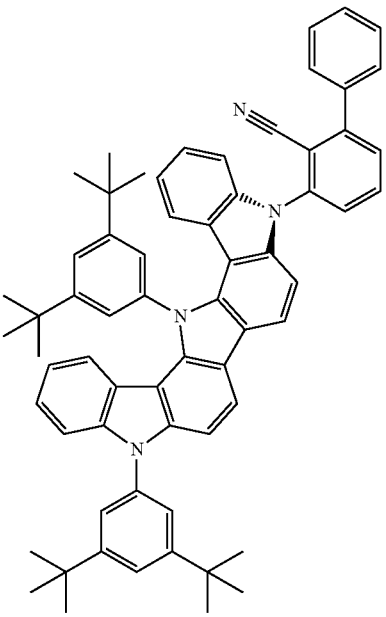
75
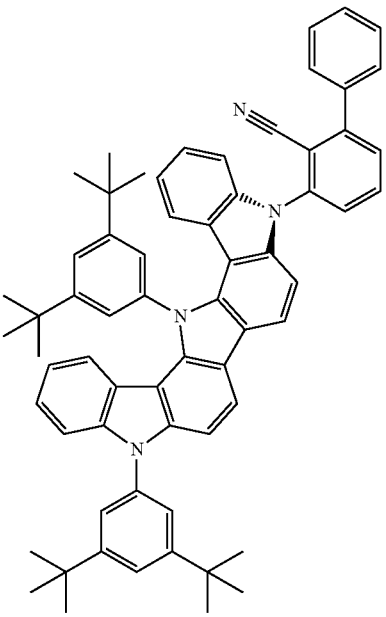
76
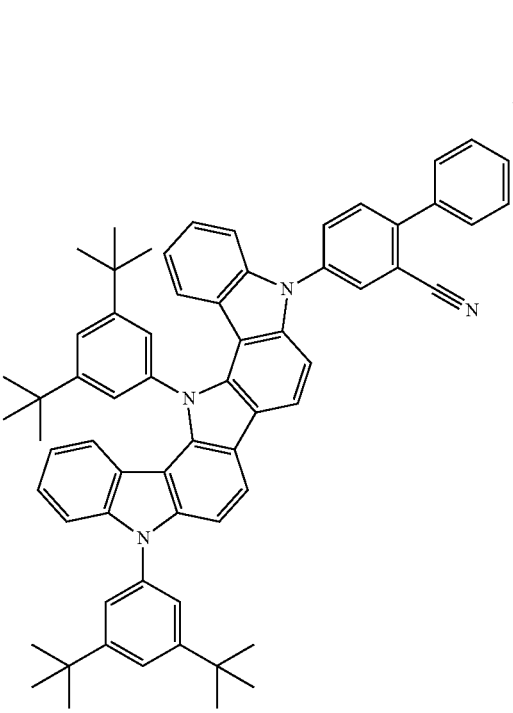

77
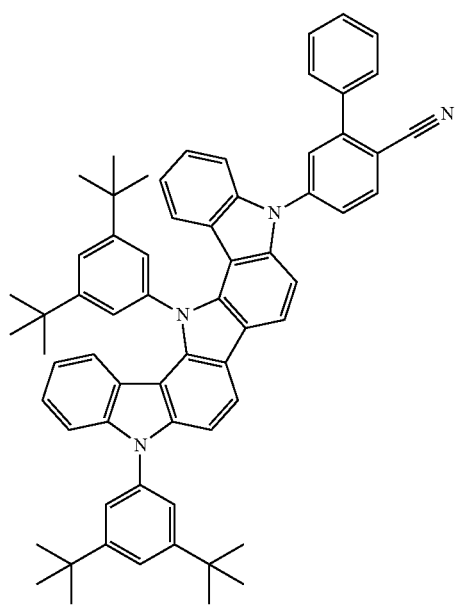
78
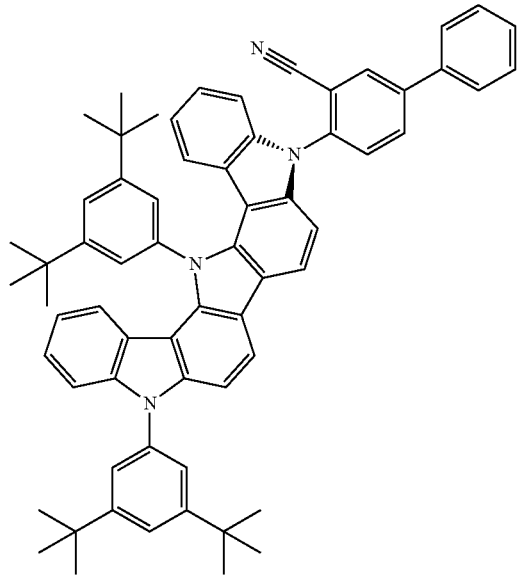
79
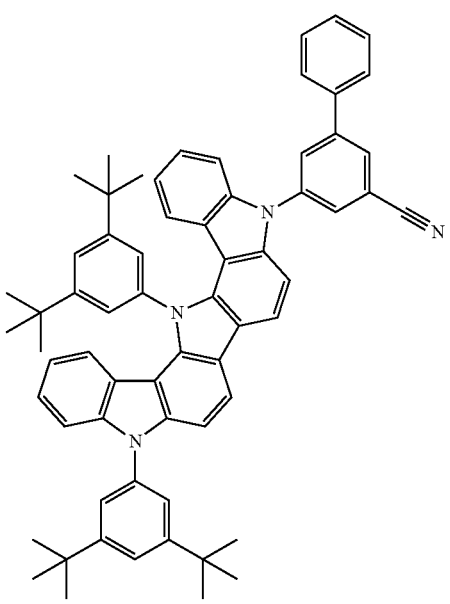
80
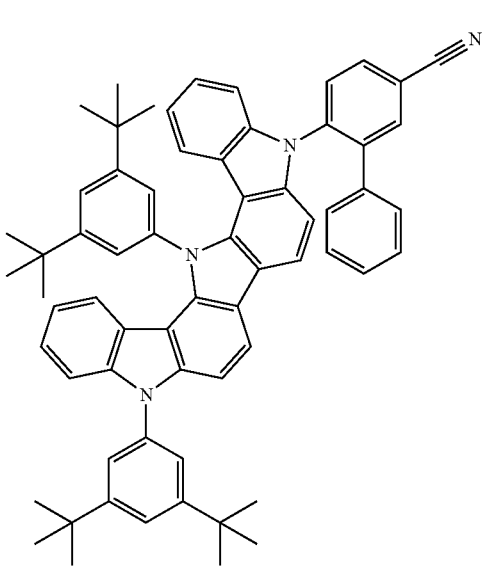

81
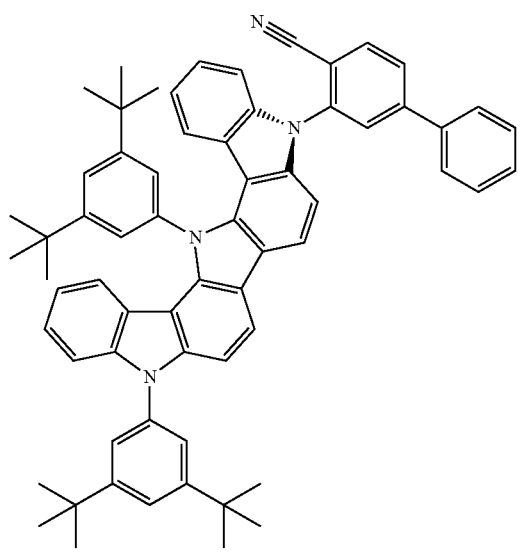
83
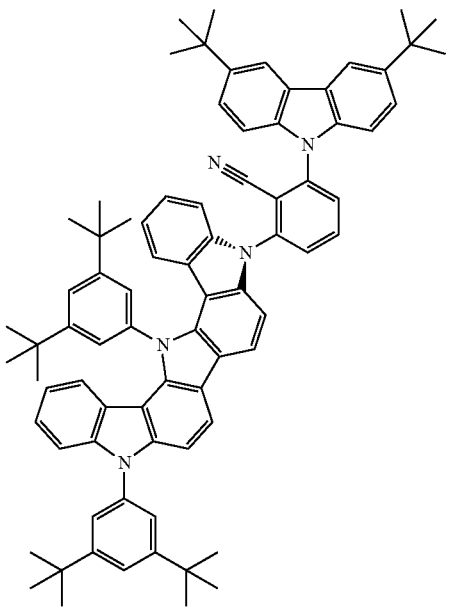
82
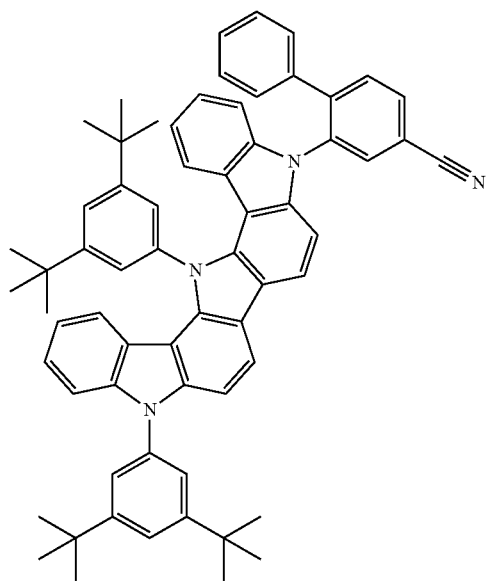
84
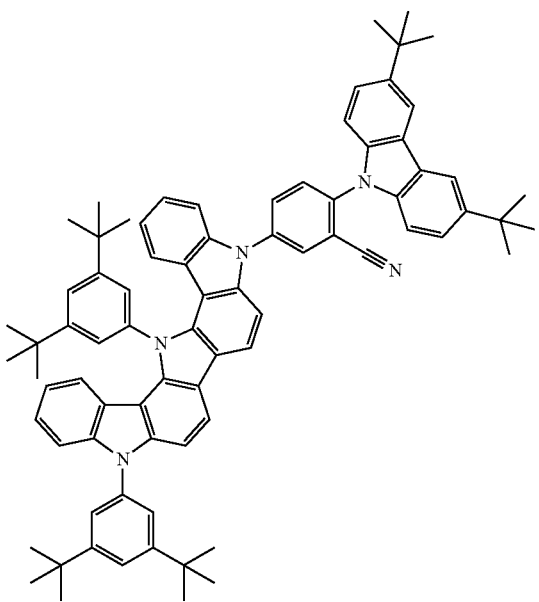

85
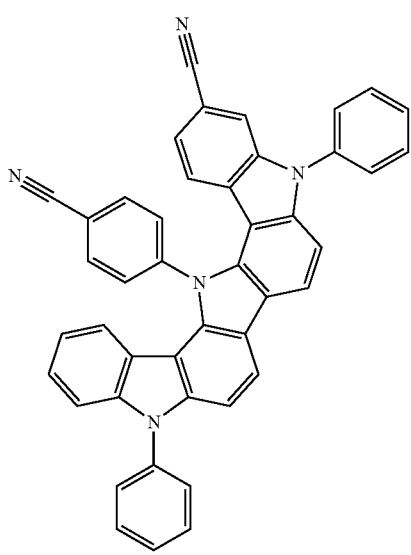
86
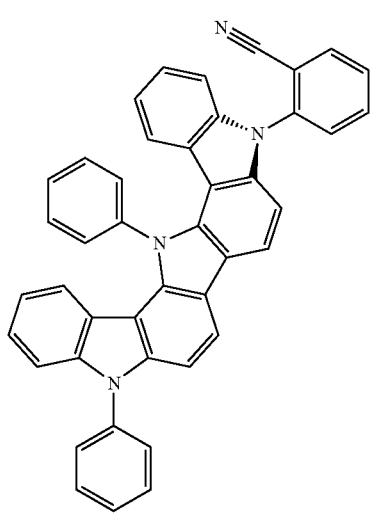
87
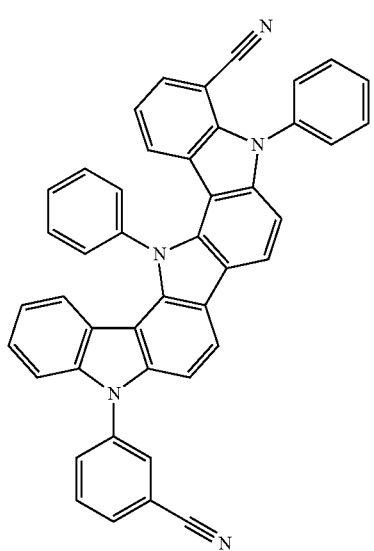
88
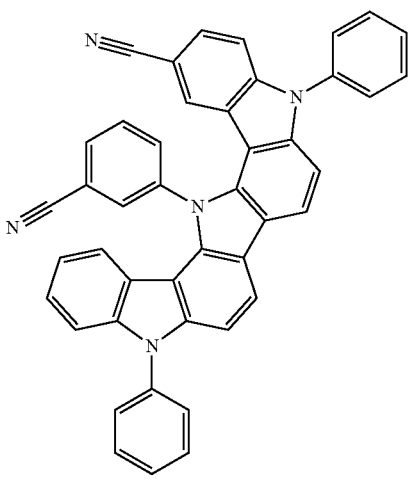
89
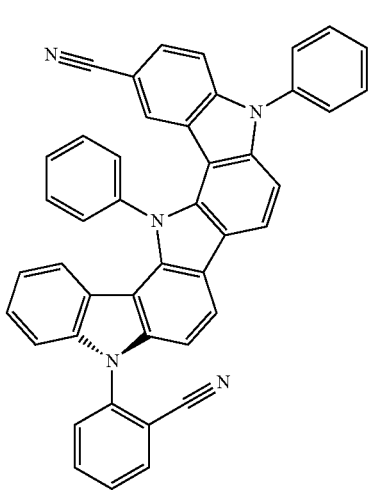
90
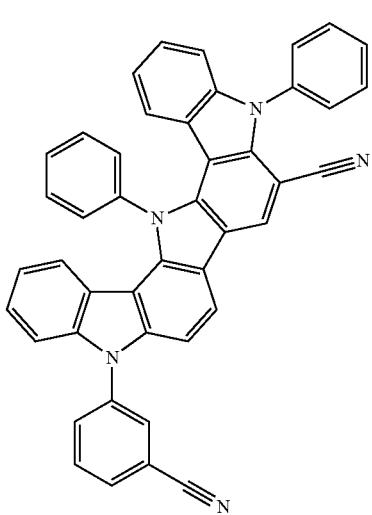

91
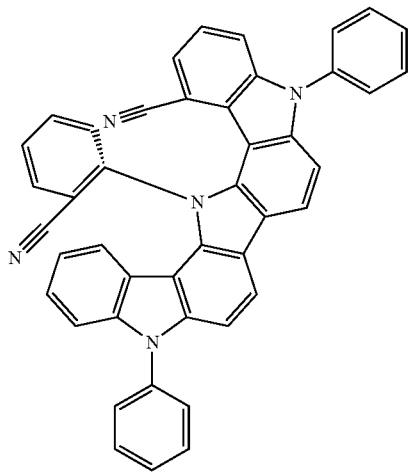
92
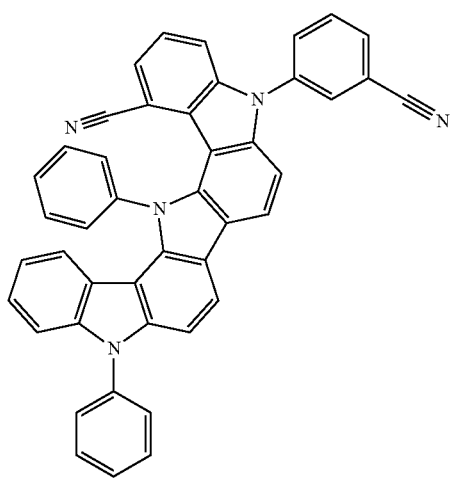
93
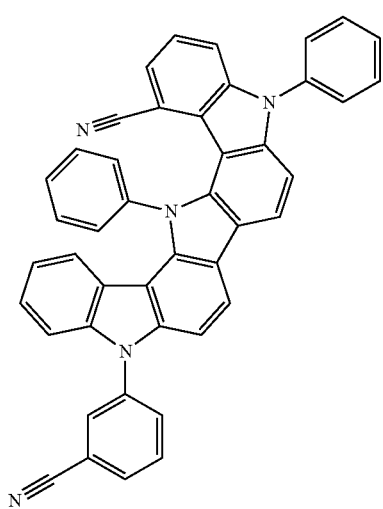
94
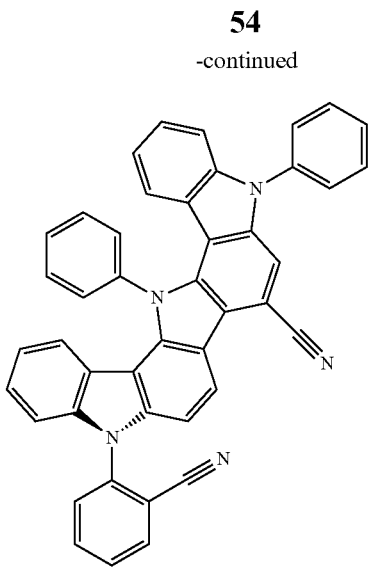
95
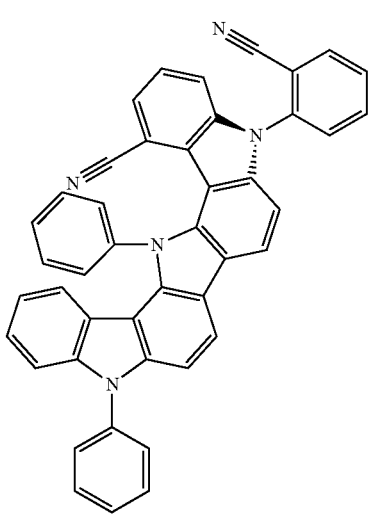
96
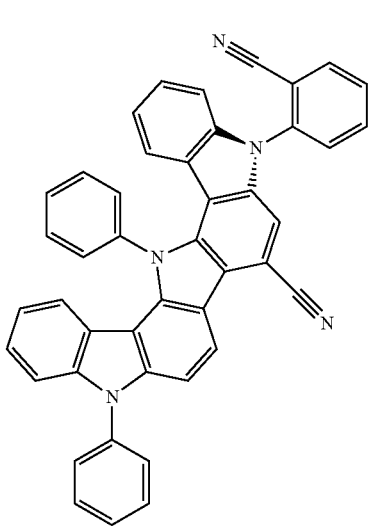

97
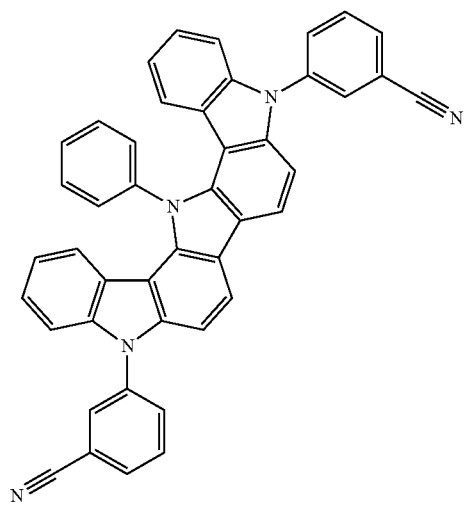
98
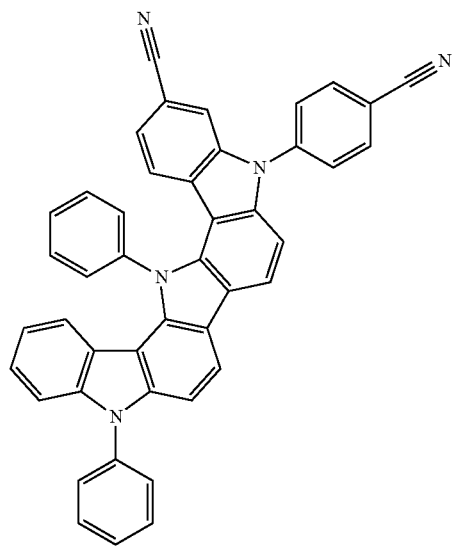
99
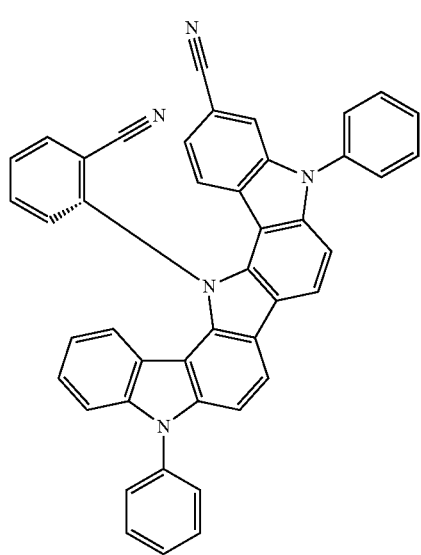
100
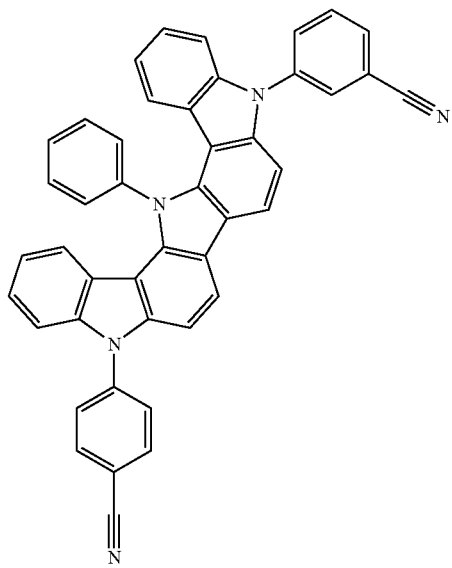
101
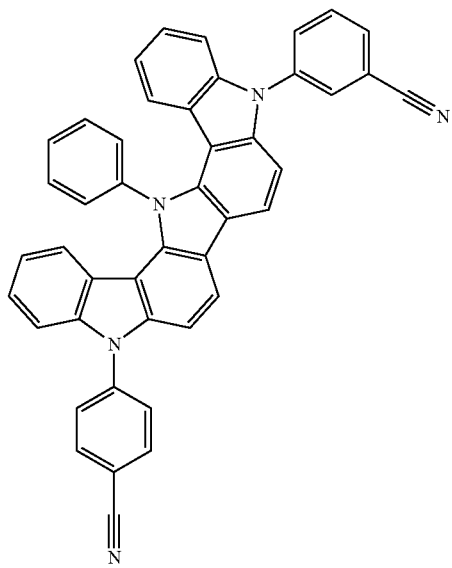
102
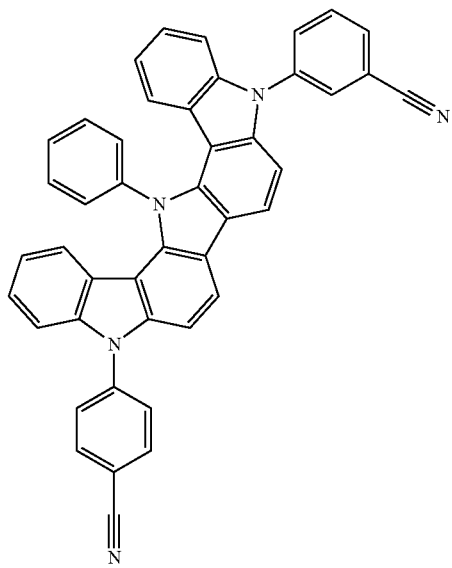

103
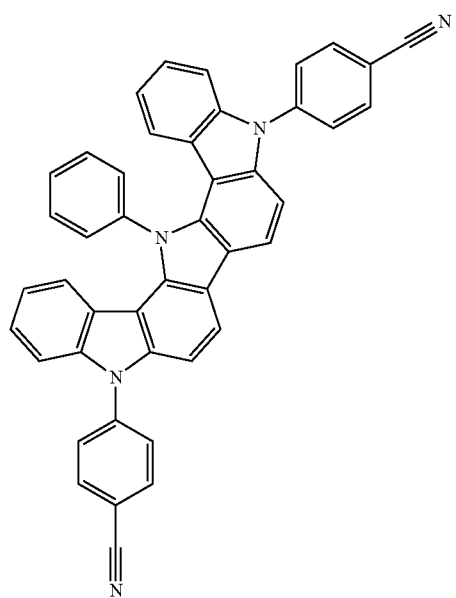
104
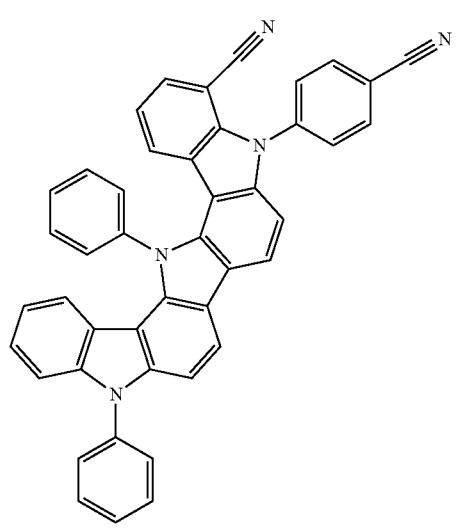
105
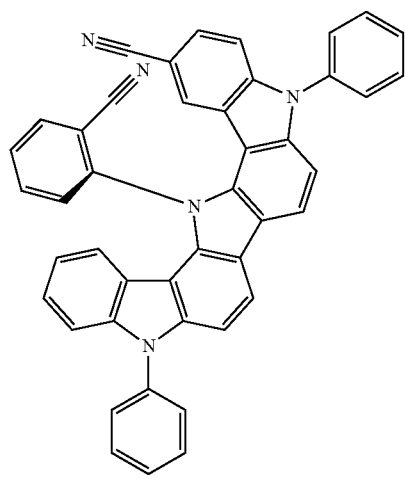
106
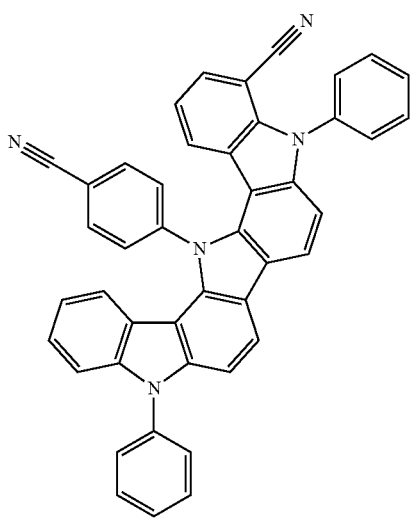
107
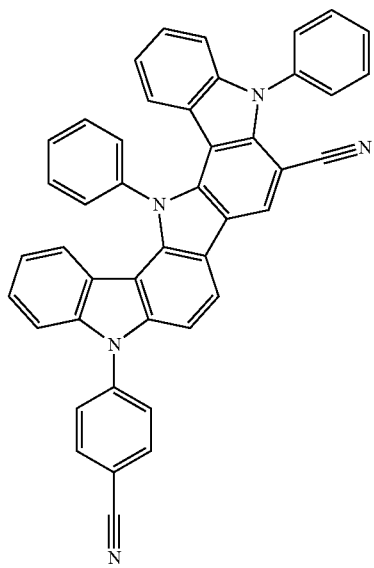
108
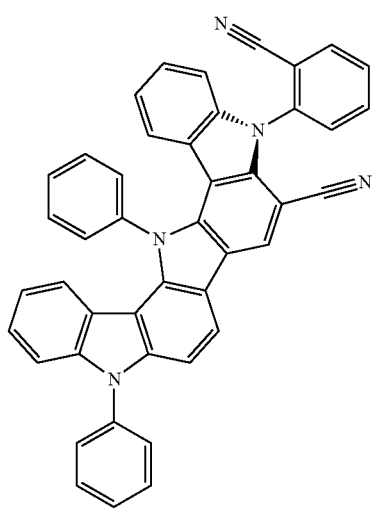

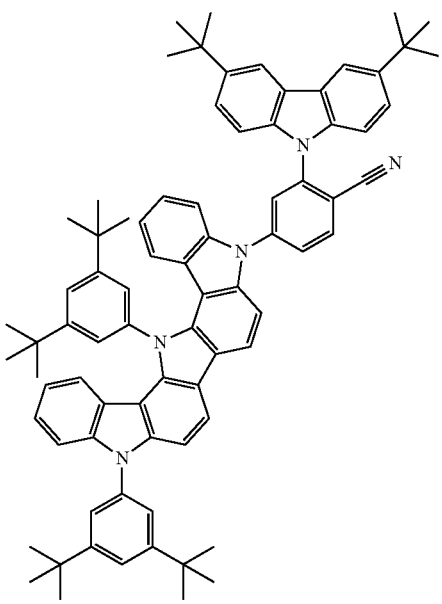

109

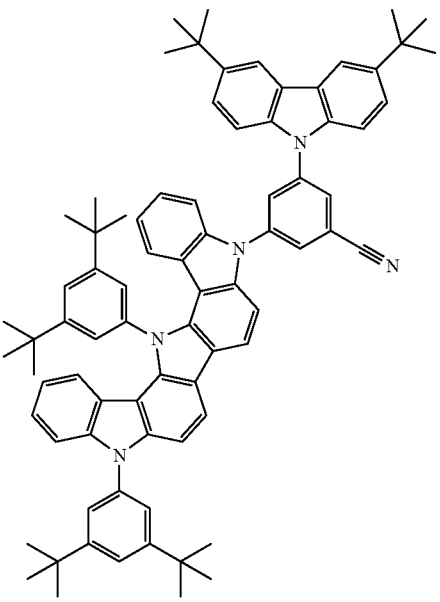

111

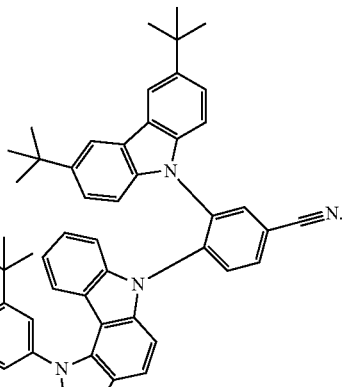

112

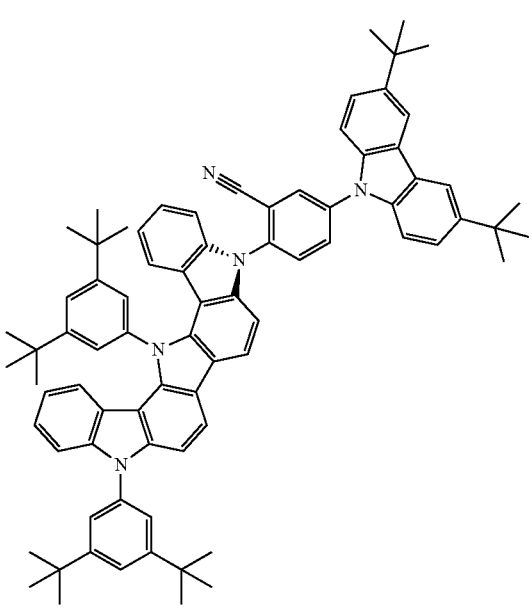

110

In an embodiment, the condensed cyclic compound represented by Formula 1 may satisfy Equations 1 and 2:

$$2.5\ eV < E_{S1(TD)} < 3\ eV \qquad \text{Equation 1}$$

$$\Delta E_{ST} < 0.3\ eV. \qquad \text{Equation 2}$$

$E_{S1(TD)}$ in Equation 1 is singlet energy (eV) of the condensed cyclic compound, and $\Delta E_{ST}$ in Equation 2 is a difference between singlet energy (eV) and triplet energy (eV) of the condensed cyclic compound.

Since the compound represented by Formula 1 includes one to ten cyano groups or cyano group-containing groups, the condensed cyclic compound represented by Formula 1 may have excellent electric stability. In particular, due to molecular characteristics in which a cyano group or a cyano group-containing group is substituted with an N atom or a benzene ring included in a diindolocarbazole skeleton, when applying to the organic light-emitting device, charge mobility is high and it is suitable for implementation of short wavelength such as blue light. Therefore, an electronic device, for example, an organic light-emitting device, which includes the condensed cyclic compound represented by Formula 1 may have a long lifespan, high quantum efficiency, and high current efficiency.

In addition, since the compound represented by Formula 1 configures diindolocarbazole in which seven ring structures are condensed, the compound has a long molecular length and a rigid skeleton. Thus, the polarization of the electron density easily occurs in the condensed cyclic compound represented by Formula 1, and thus, the condensed cyclic compound may have a high triplet energy value and excellent charge transport characteristics. Therefore, an electronic device, for example, an organic light-emitting device, which includes the condensed cyclic compound represented by Formula 1 may have a low driving voltage, high quantum efficiency, high current efficiency, and high luminance.

The molecular weight, highest occupied molecular orbital (HOMO) energy level, lowest unoccupied molecular orbital (LUMO) energy level, $T_1$ energy level, and $S_1$ energy level of some Compounds in the condensed cyclic compound represented by Formula 1 were evaluated by using Gaussian 09 program accompanied by molecular structure optimization by a density functional theory (DFT) based on B3LYP, and evaluation results are shown in Table 1.

TABLE 1

|  | HOMO (eV) | LUMO (eV) | $T_1$ (eV) | $S_1$ (eV) | $\Delta E_{ST}$ |
|---|---|---|---|---|---|
| Compound 41 | −4.855 | −1.613 | 2.664 | 2.726 | 0.061 |
| Compound 61 | −4.805 | −1.656 | 2.612 | 2.689 | 0.078 |
| Compound 84 | −4.771 | −1.678 | 2.563 | 2.665 | 0.102 |
| Compound 80 | −4.724 | −1.626 | 2.572 | 2.646 | 0.074 |
| Compound 76 | −4.709 | −1.599 | 2.583 | 2.703 | 0.119 |

Referring to Table 1, it is confirmed that the condensed cyclic compound represented by Formula 1 has excellent electric characteristics, for example, a high $T_1$ energy level.

Synthesis methods of the condensed cyclic compound represented by Formula 1 may be recognizable by one of ordinary skill in the art by referring to Synthesis Examples provided below.

Accordingly, another aspect of embodiments provides an organic light-emitting device that includes: a first electrode; a second electrode; and an organic layer that is disposed between the first electrode, wherein the second electrode includes an organic layer including an emission layer, and wherein the organic layer includes at least one of the condensed cyclic compound represented by Formula 1.

The condensed cyclic compound represented by Formula 1 may be used in the organic layer of the organic light-emitting device. For example, the condensed cyclic compound represented by Formula 1 may be used as a host in the emission layer of the organic layer. However, embodiments of the present disclosure are not limited thereto.

The organic light-emitting device may have, due to the inclusion of an organic layer including the condensed cyclic compound represented by Formula 1, low driving voltage, high quantum efficiency, high brightness, and long lifespan.

In addition, the organic light-emitting device may include the emission layer including the condensed cyclic compound represented by Formula 1, thereby emitting blue light having a maximum emission wavelength in a range of about 440 nanometers (nm) to about 490 nm.

The condensed cyclic compound represented by Formula 1 is suitable for use in an organic layer of an organic light-emitting device, for example, for use a material for forming a hole transport layer, a material for forming an electron blocking layer, and/or a material for forming an emission layer of the organic layer. Thus, another aspect of the present description provides an organic light-emitting device that includes: a first electrode; a second electrode; and an organic layer that is disposed between the first electrode and the second electrode, wherein the organic layer includes an emission layer; and wherein the organic layer includes at least one condensed cyclic compound represented by Formula 1.

The organic light-emitting device may have, due to the inclusion of an organic layer including the condensed cyclic compound represented by Formula 1, low driving voltage, high quantum efficiency, high brightness, high quantum emission efficiency, and a long lifespan.

For example, the condensed cyclic compound represented by Formula 1 may be included in the emission layer.

In an embodiment, the condensed cyclic compound represented by Formula 1 may be included in the emission layer, and the condensed cyclic compound represented by Formula 1 may be a material for delayed fluorescence.

In an embodiment, the emission layer includes a host and a dopant, wherein an amount of the host may be greater than that of the dopant. The host may include the compound represented by Formula 1. The condensed cyclic compound which serves as the host may deliver energy to the dopant according to the delayed fluorescence emission mechanism. The dopant may include at least one selected from a fluorescent dopant and a phosphorescent dopant. The dopant may be selected from any known dopants. The host may further include any host selected from known hosts.

In one or more embodiment, the emission layer may include a host and a dopant, wherein an amount of the host may be greater than that of the dopant. The dopant may include the condensed cyclic compound represented by Formula 1. The condensed cyclic compound which serves as the dopant may emit delayed fluorescence according to the delayed fluorescence emission mechanism. The dopant may be selected from any known dopants.

The emission layer may emit red light, green light, or blue light.

In an embodiment, the emission layer may be a blue emission layer including a phosphorescent dopant, but embodiments of the present disclosure are not limited thereto.

In an embodiment, the condensed cyclic compound represented by Formula 1 may be included in the hole transport region.

For example, the hole transport region of the organic light-emitting device may include at least one selected from the hole transport layer and the electron blocking layer, wherein at least one of the hole transport layer and the electron blocking layer may include the condensed cyclic compound represented by Formula 1.

For example, the hole transport region of the organic light-emitting device may include the hole transport layer, wherein the hole transport layer includes the condensed cyclic compound represented by Formula 1.

For example, the hole transport region of the organic light-emitting device may include the electron blocking layer, wherein the electron blocking layer includes the condensed cyclic compound represented by Formula 1. The electron blocking layer may directly contact the emission layer.

In an embodiment, the condensed cyclic compound represented by Formula 1 may be included in the electron transport region.

For example, the electron transport region of the organic light-emitting device may include the electron transport layer, wherein the electron transport layer includes the condensed cyclic compound represented by Formula 1.

For example, the electron transport region of the organic light-emitting device may include the hole blocking layer, wherein the hole blocking layer includes the condensed cyclic compound represented by Formula 1. The hole blocking layer may directly contact the emission layer.

In an embodiment, the emission layer may include the condensed cyclic compound. Here, a percentage of the fluorescence emitting components among the total light-emitting components emitted from the emission layer may be at least 90%, for example, at least 95% (for example, at least 98%). In addition, the emission layer may include the condensed cyclic compound represented by Formula 1, but may not include a phosphorescence emitting compound (for example, an organometallic compound including a heavy metal). Thus, the emission layer may be distinctly distinguished from a phosphorescence emission layer which includes a phosphorescent dopant and accordingly has at least 80% of the phosphorescent component among the total light-emitting components.

The emission layer of the organic light-emitting device may be embodied according to Embodiments 1, 2, or 3, according to use of the condensed cyclic compound represented by Formula 1.

First Embodiment

A first embodiment is an embodiment in which the condensed cyclic compound included in the emission layer is used as a fluorescent emitter, that is, the condensed cyclic compound is a fluorescent emitter.

Therefore, according to the first embodiment, a percentage of the light-emitting components emitted from the condensed cyclic compound among the total light-emitting components emitted from the emission layer may be about 80% or more, for example, 90% or more. For example, the percentage of the light-emitting components emitted from the condensed cyclic compound among the total light-emitting components emitted from the emission layer may be 95% or more. The light-emitting components of the condensed cyclic compound may be the sum of the prompt emission components of the condensed cyclic compound and the delayed fluorescence components caused by the reverse intersystem crossing of the condensed cyclic compound.

According to the first embodiment, the emission layer may consist of the condensed cyclic compound; or the emission layer may further include a host (the host is not identical to the condensed cyclic compound).

In the first embodiment, when the emission layer further includes the host in addition to the condensed cyclic compound, an amount of the condensed cyclic compound may be in a range of about 50 parts by weight or less, for example, about 30 parts by weight or less, based on 100 parts by weight of the emission layer, and an amount of the host in the emission layer may be in a range of about 50 parts by weight or more, for example, about 70 parts by weight or more, based on 100 parts by weight of the emission layer, but embodiments of the present disclosure are not limited thereto.

The host in the first embodiment may be understood by referring to the description provided below.

Second Embodiment

A second embodiment is an embodiment in which the condensed cyclic compound included in the emission layer is used as a fluorescent host.

Therefore, according to the second embodiment, the emission layer includes a host and a fluorescent dopant. The host may include the condensed cyclic compound, and a percentage of the light-emitting components of the fluorescent dopant among the total light-emitting components emitted from the emission layer may be about 80% or more, for example, about 90% or more (for example, 95% or more).

In the second embodiment, an amount of the fluorescent dopant in the emission layer may be in a range of about 50 parts by weight or less, for example, about 30 parts by weight or less, based on 100 parts by weight of the emission layer, and an amount of the host in the emission layer may be in a range of 50 parts by weight or more, for example, about 70 parts by weight or more, based on 100 parts by weight of the emission layer, but embodiments of the present disclosure are not limited thereto.

The fluorescent dopant in the second embodiment may be understood by referring to the description provided below.

In the second embodiment, the host may consist of the condensed cyclic compound, or may further include other known host. The other known host will be described below.

Third Embodiment

A third embodiment is an embodiment in which the condensed cyclic compound included in the emission layer is used as an auxiliary dopant.

Therefore, according to the third embodiment, the emission layer may include a host, an auxiliary dopant, and a fluorescent dopant, wherein the auxiliary dopant may include the condensed cyclic compound, and the emission layer may satisfy Equations 2 and 3:

$$E_{T1(HOST)} - E_{T1(AD)} > 0.05 \text{ eV} \qquad \text{Equation 3}$$

$$E_{S1(FD)} - E_{S1(AD)} < 0 \text{ eV}. \qquad \text{Equation 4}$$

In Equation 3, $E_{T1(HOST)}$ is triplet energy (eV) of the host, and $E_{T1(AD)}$ is triplet energy (eV) of the auxiliary dopant, in Equation 4, $E_{S1(FD)}$ is singlet energy (eV) of the fluorescent dopant, and $E_{S1(AD)}$ is singlet energy (eV) of the auxiliary dopant, and $E_{T1(HOST)}$, $E_{T1(AD)}$, and $E_{S1(FD)}$ are evaluated by using a DFT method of Gaussian program structurally optimized at a level of B3LYP/6-31G(d,p).

In the third embodiment, since Equation 3 is satisfied (for example, since $E_{T1(HOST)} - E_{T1(AD)}$ is in a range of 0.10 eV to 0.65 eV), the energy of triplet exciton generated in the auxiliary dopant of the emission layer cannot be transferred to the host of the emission layer, and the probability that the triplet exciton will be lost in the path other than the light emission may be reduced. Therefore, the organic light-emitting device may have high efficiency.

In addition, in the third embodiment, since Equation 4 is satisfied (for example, since $E_{S1(FD)} - E_{S1(AD)}$ is in a range of −0.4 eV to −0.05 eV), the energy of singlet exciton generated in the auxiliary dopant of the emission layer can be rapidly transferred to the fluorescent dopant. Therefore, the light emission is substantially performed only in the fluorescent dopant in the emission layer of the organic light-emitting device, and the fluorescence spectrum having excellent color purity based on the fluorescent dopant may be implemented. In addition, the fluorescent material having a relatively short lifespan may be obtained, and it is possible to suppress the roll-off phenomenon that may occur under high luminance due to interaction between a plurality of excitons (exciton-exciton interaction) or interaction between exciton and charge (hole or electron) (exciton-platon interaction), so that an organic light-emitting device having high efficiency may be implemented. Furthermore, since the auxiliary dopant has a short exciton lifespan, the probability of chemical or physical deterioration that may occur in the exciton state of the auxiliary dopant may be reduced, and thus, the organic light-emitting device satisfying Equation 4 may have improved durability.

In the second embodiment, an amount of the fluorescent dopant in the emission layer may be in a range of about 50 parts by weight or less, for example, about 30 parts by weight or less, based on 100 parts by weight of the emission layer, and an amount of the host in the emission layer may be in a range of about 50 parts by weight or more, for example, about 70 parts by weight or more, based on 100 parts by weight of the emission layer, and an amount of the auxiliary dopant may be in a range of about 30 parts by weight or less, for example, about 20 parts by weight or less, based on 100 parts by weight of the emission layer, but embodiments of the present disclosure are not limited thereto.

The host and the fluorescent dopant in the third embodiment may be understood by referring to the description provided below.

The emission layer according to the second embodiment may include: i) the condensed cyclic compound (host) defined herein and ii) the fluorescent dopant (fluorescent emitter), and the emission layer according to the third embodiment may include i) the host, ii) the fluorescent dopant (fluorescent emitter), and iii) the condensed cyclic compound (auxiliary dopant) defined herein. In the emission layers according to the second embodiment and the third embodiment, energy transfer from the condensed cyclic compound to the fluorescent dopant (fluorescent emitter) may be obtained according to the foster energy transfer mechanism.

The hosts according to the first embodiment and the second embodiments may be selected from known fluorescent hosts.

For example, the host may have a triplet energy level of about 2.9 electron volts (eV) or more, for example, a triplet energy level of 2.9 eV to 4.5 eV. Therefore, energy transfer from the host to the fluorescent emitter, the fluorescent dopant, and/or the fluorescent dopant may be effectively obtained, so that the organic light-emitting device may have high efficiency.

For example, the host may include at least one compound selected from a fluorene-containing compound, a carbazole-containing compound, a dibenzofuran-containing compound, a dibenzothiophene-containing compound, indeno carbazole-containing compound, an indolocarbazole-containing compound, a benzofurocarbazole-containing compound, a benzothienocarbazole-containing compound, an acridine-containing compound, dihydroacridine-containing compound, a triindolobenzene-containing compound, a pyridine-containing compound, a pyrimidine-containing compound, a triazine-containing compound, a silicon-containing compound, a cyano group-containing compound, a phosphine oxide-containing compound, and a sulfoxide-containing compound, but embodiments of the present disclosure are not limited thereto.

In an embodiment, the host may include a compound including at least one carbazole ring and at least one cyano group.

For example, the host may include at least one compound selected from Compounds H1 to H19, but embodiments of the present disclosure are not limited thereto:

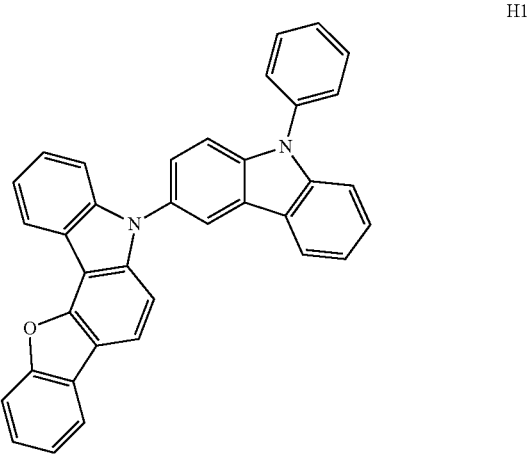

H1

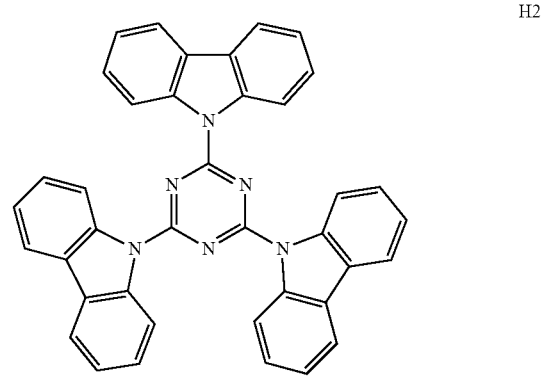

H2

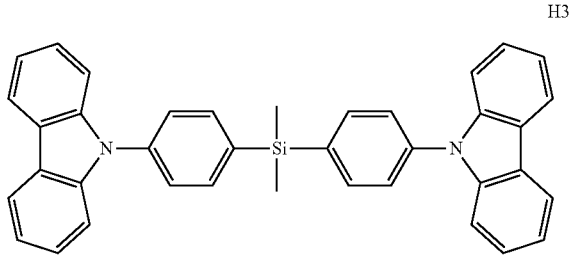

H3

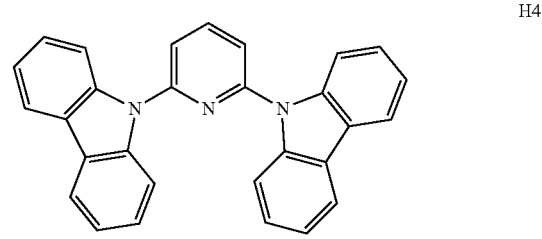

H4

H5
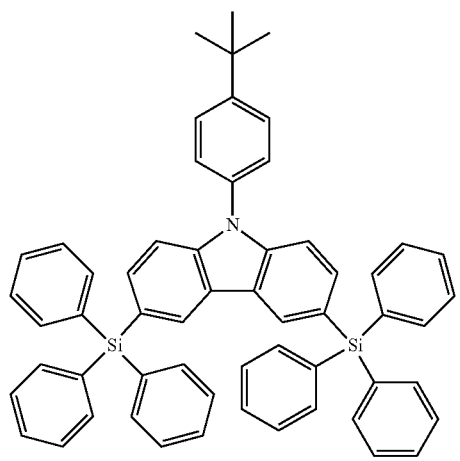
H6
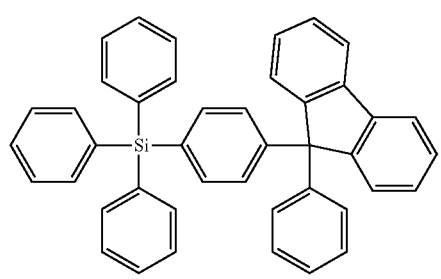
H7
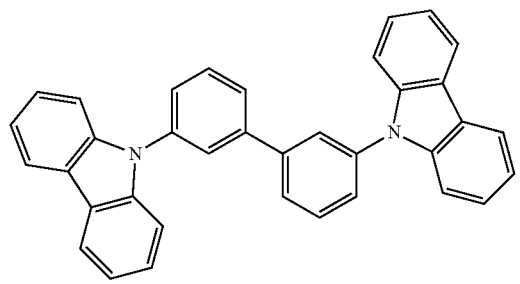
H8
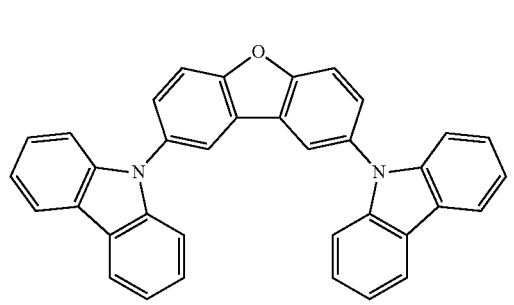
H9
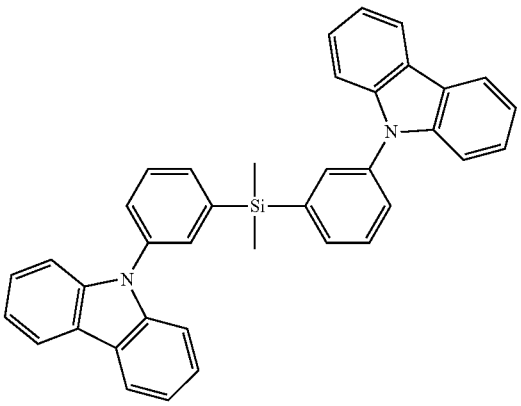
H10
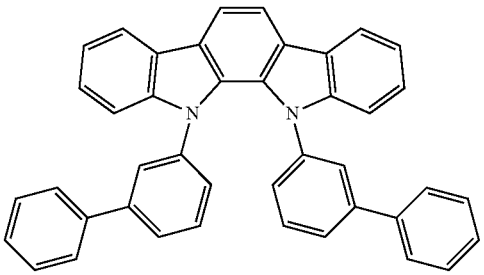
H11
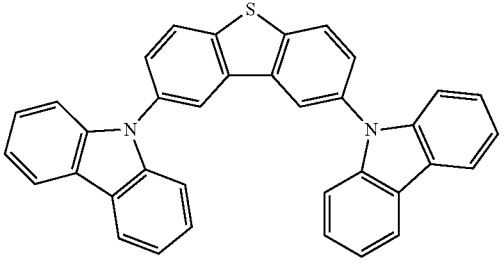
H12
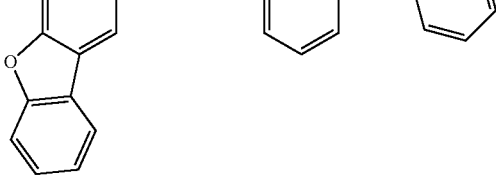

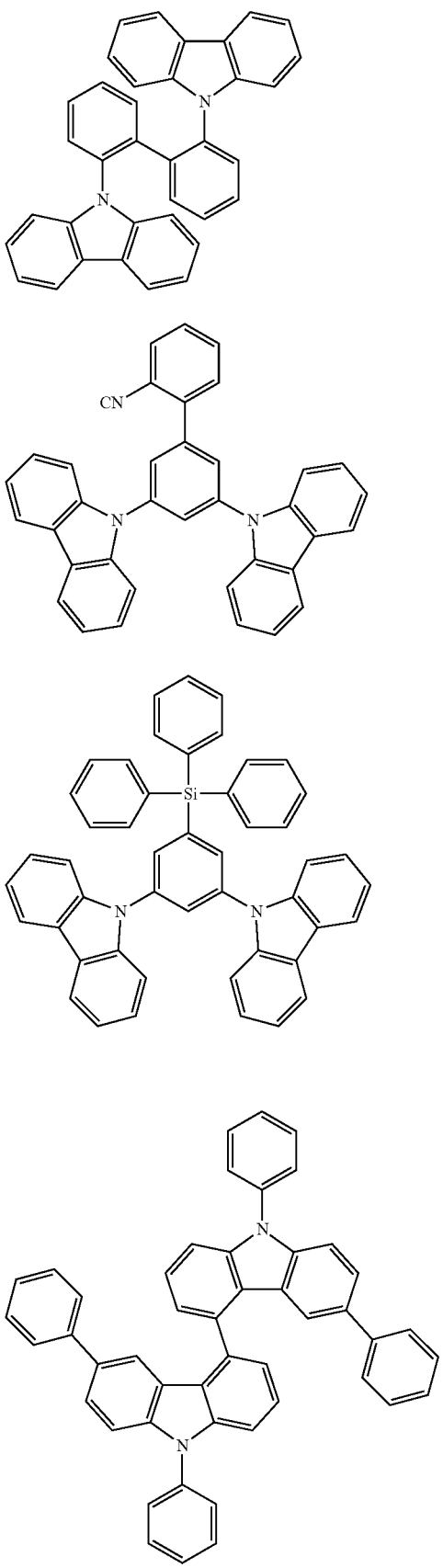

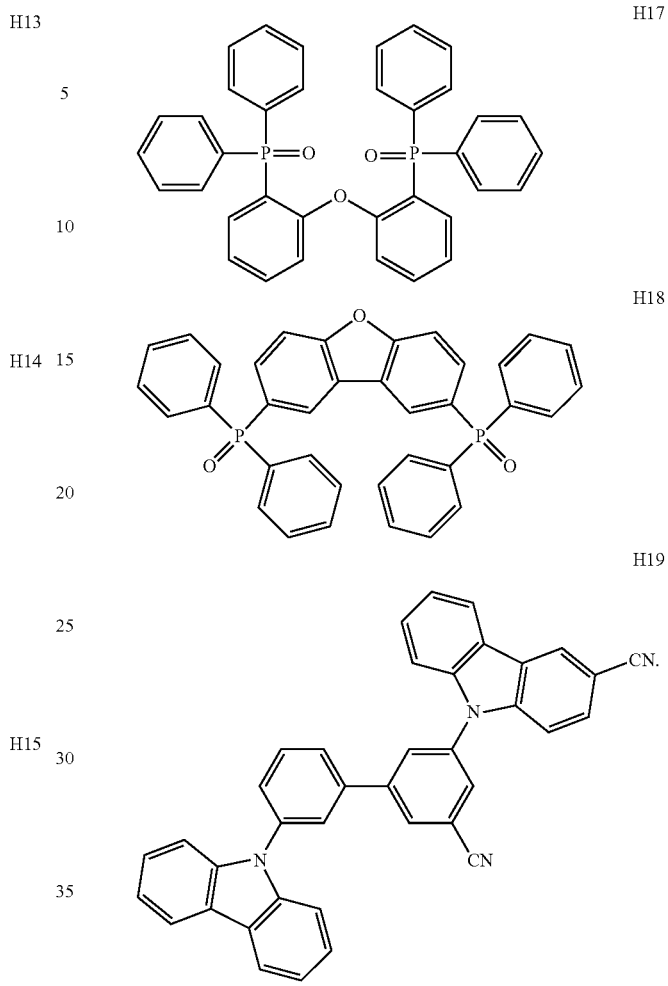

The fluorescent dopants of Embodiments 2 and 3 may each be selected from a condensed polycyclic compound and a styryl-based compound.

For example, the fluorescent dopant may include one selected from a naphthalene-containing core, a fluorene-containing core, a spiro-bifluorene-containing core, a benzofluorene-containing core, a dibenzofluorene-containing core, a phenanthrene-containing core, an anthracene-containing core, a fluoranthene-containing core, a triphenylene-containing core, a pyrene-containing core, a chrysene-containing core, a naphthacene-containing core, a picene-containing core, a perylene-containing core, a pentaphene-containing core, an indenoanthracene-containing core, a tetracene-containing core, a bisanthracene-containing core, and cores represented by Formulae 501-1 to 501-18, but embodiments of the present disclosure are not limited thereto:

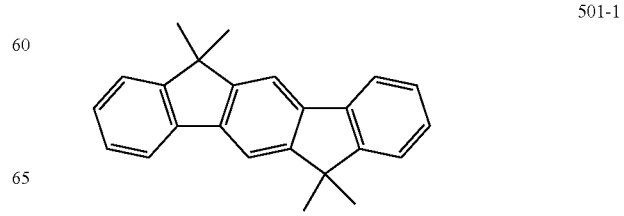

-continued
501-2
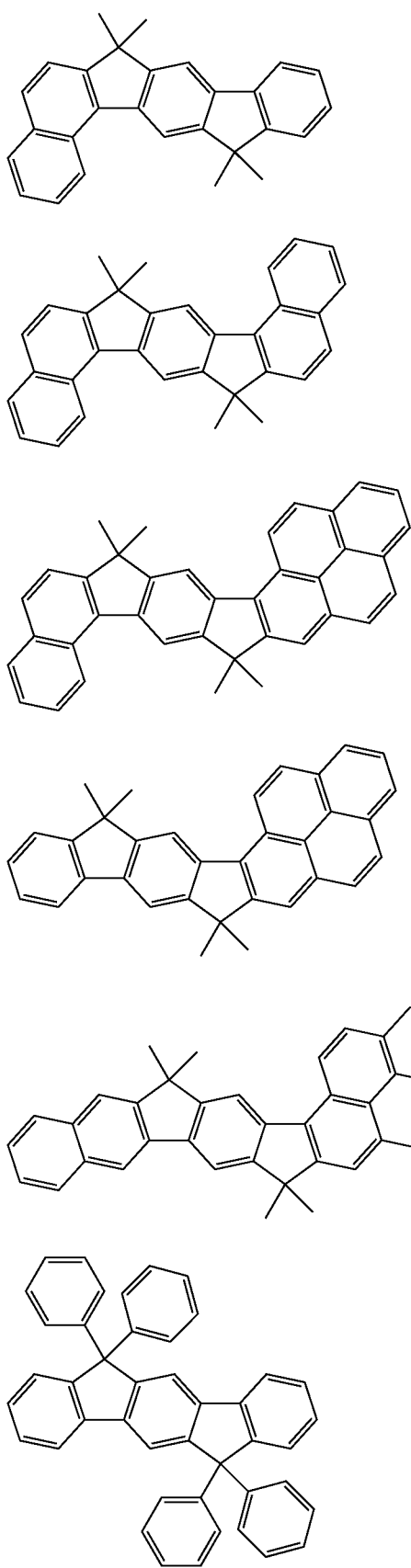
501-3
501-4
501-5
501-6
501-7
-continued
501-8
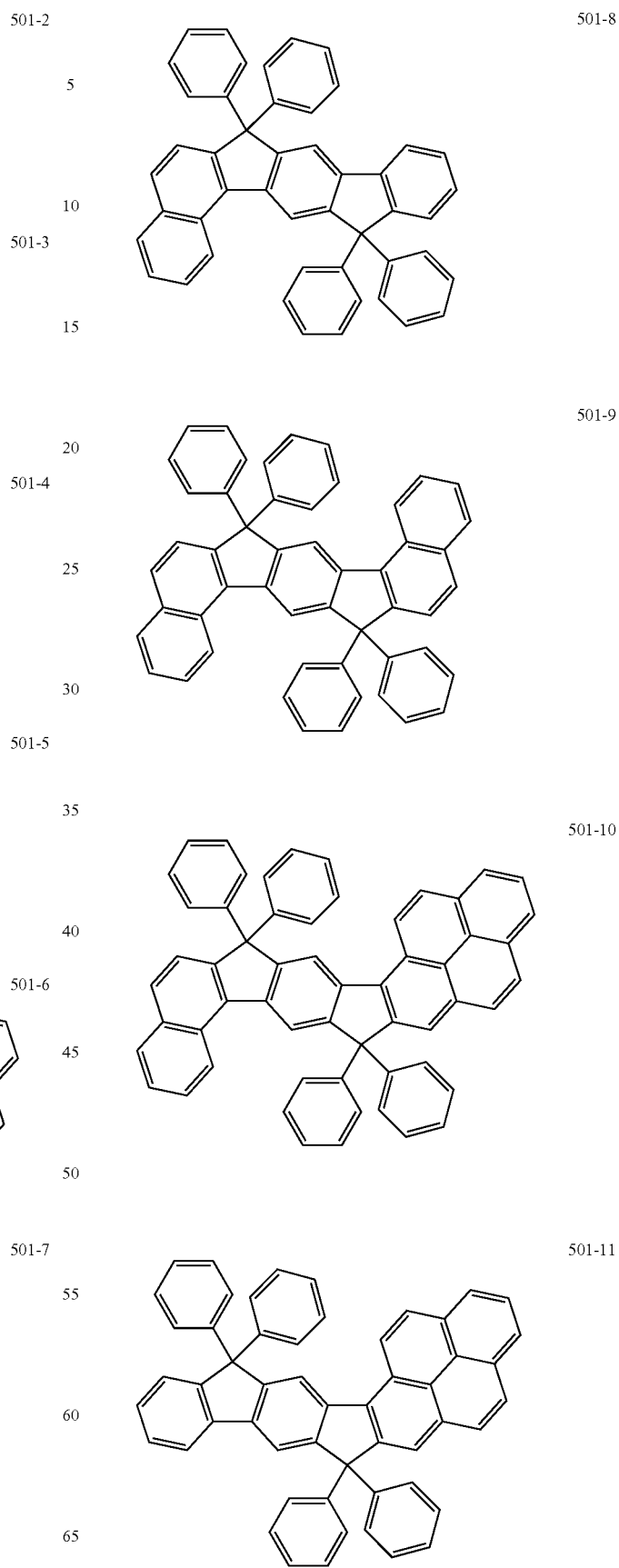
501-9
501-10
501-11

501-12
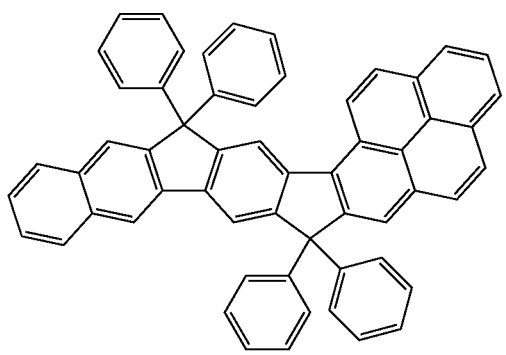
501-13
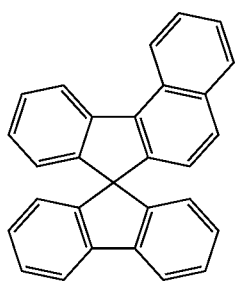
501-14
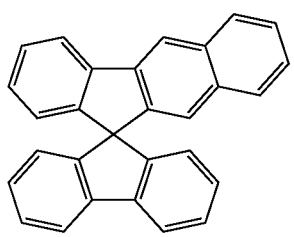
501-15
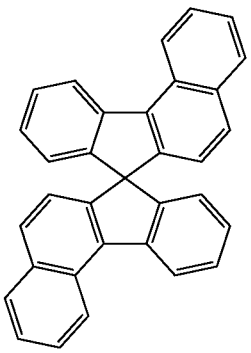
501-16
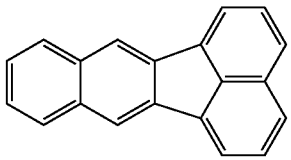
501-17
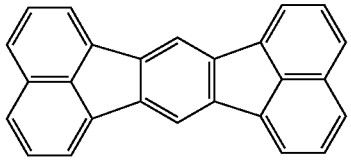
501-18
In an embodiment, the fluorescent dopant may be selected from a styryl-amine-based compound and a styryl-carbazole-based compound, but embodiments of the present disclosure are not limited thereto.
In one or more embodiments, the fluorescent dopant may include at least one compound selected from Compounds FD(1) to FD(16) and FD1 to FD13:
FD(1)
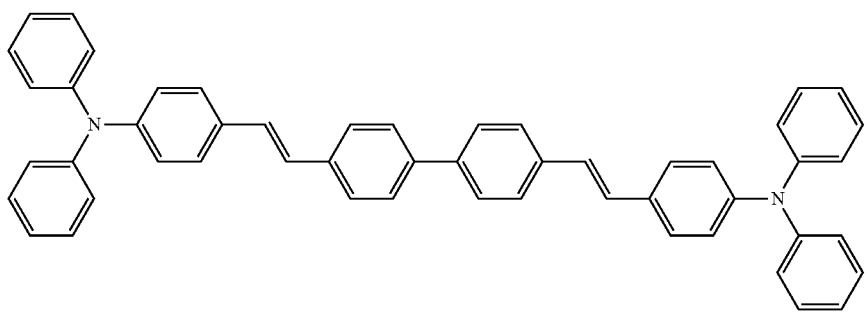

-continued
FD(2)
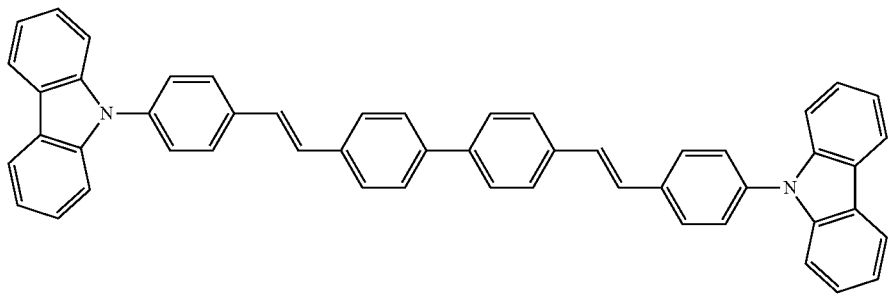
FD(3) FD(4)
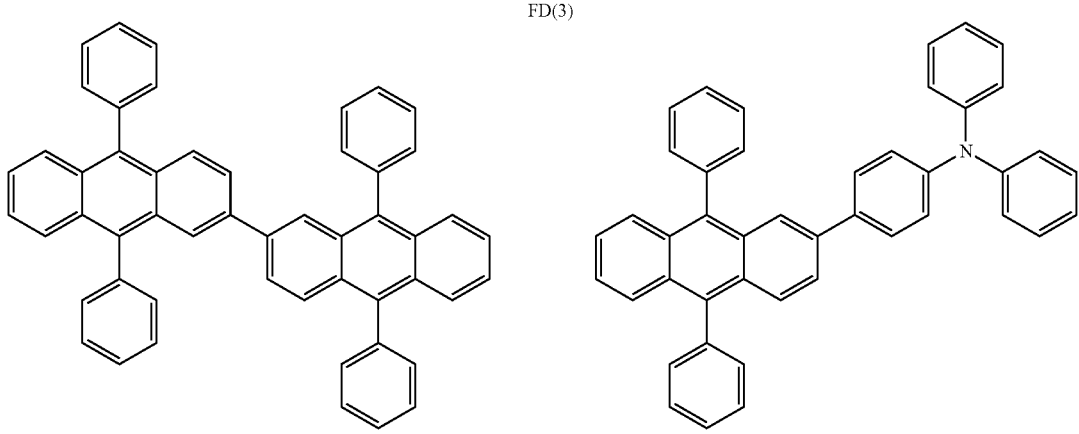
FD(5)
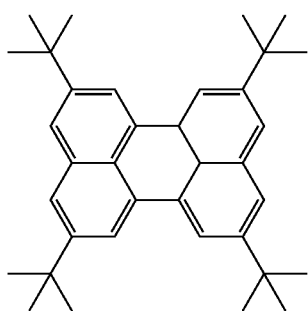
FD(6)
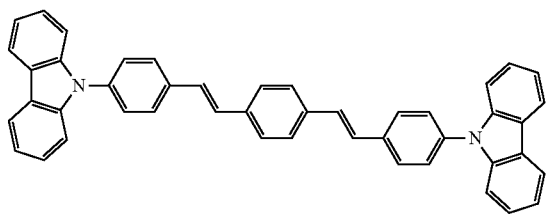
FD(7)
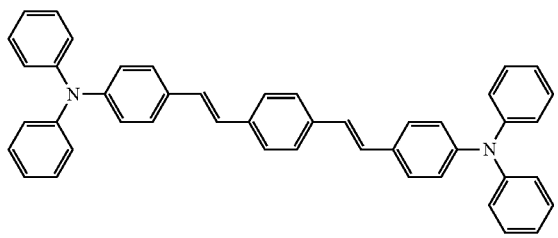
FD(8)
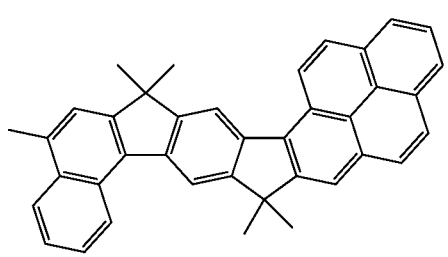

FD(9)
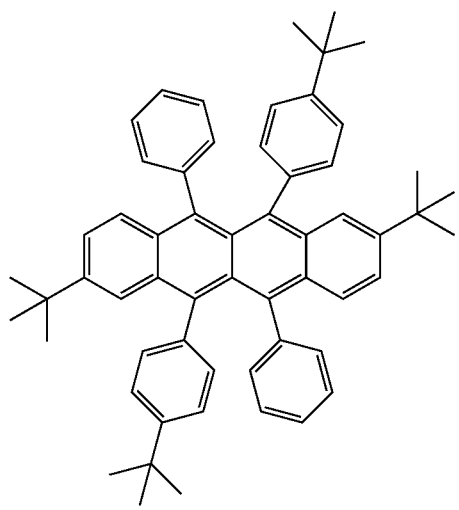
FD(10)
FD(11)
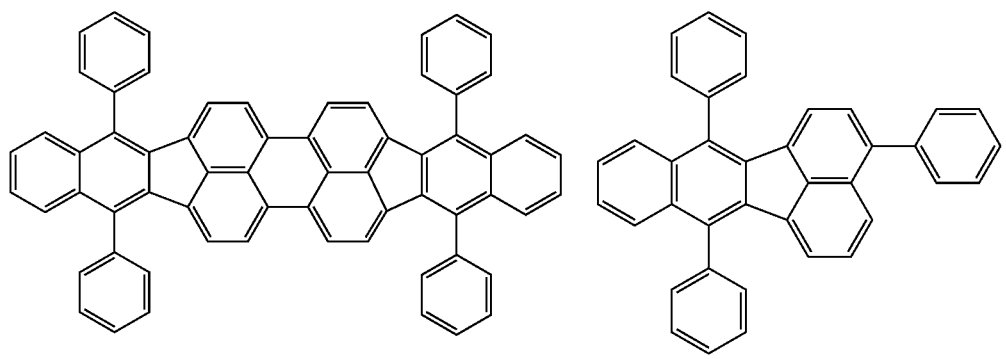
FD(12)
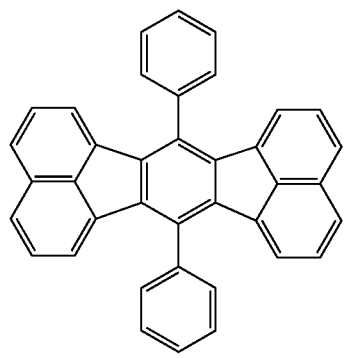
FD(13)
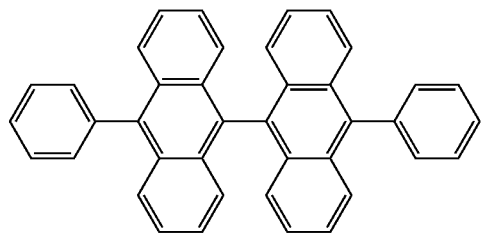
FD(14)
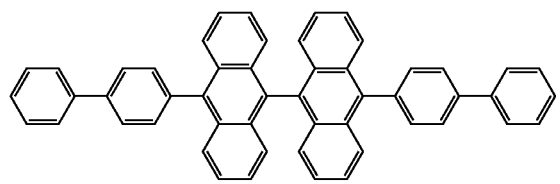
FD(15)
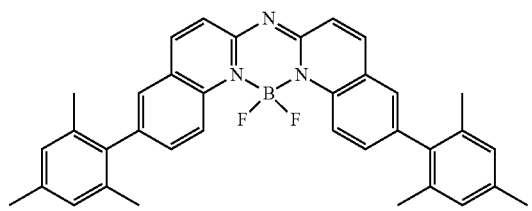

-continued
FD(16)
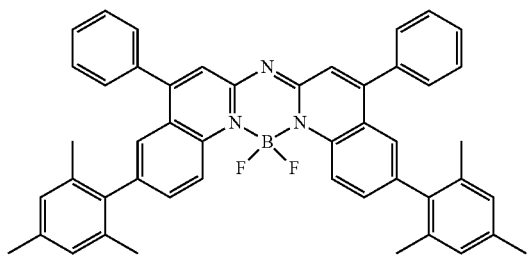
FD1
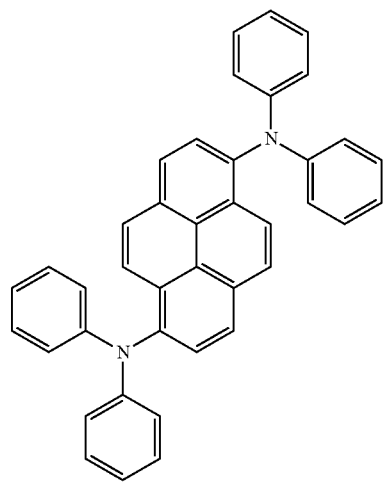
FD2
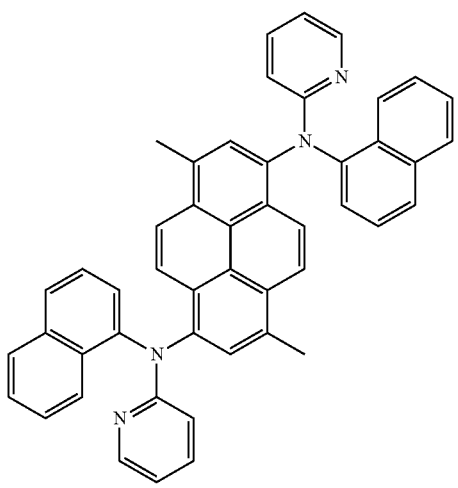
FD3
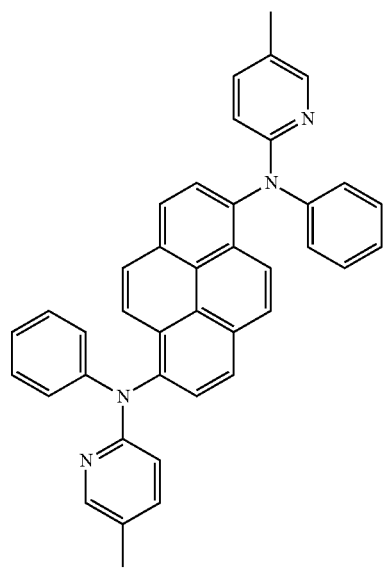

-continued
FD4
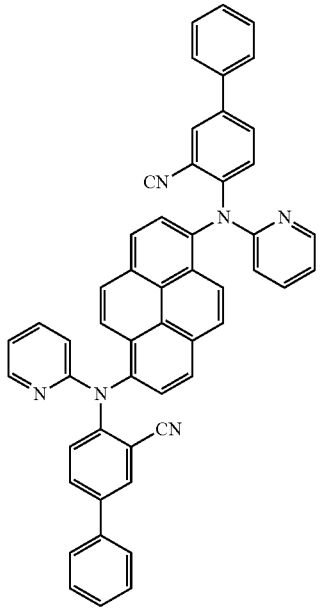
FD5
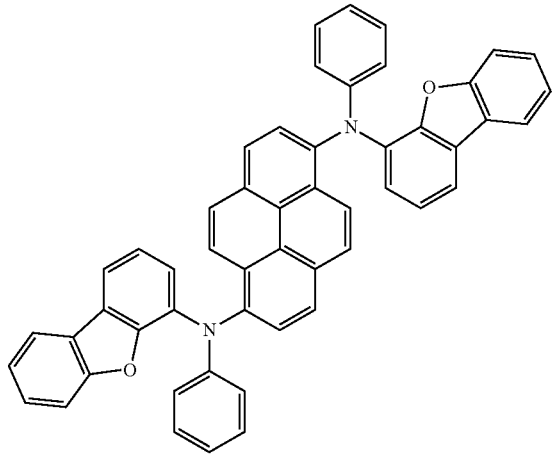
FD6
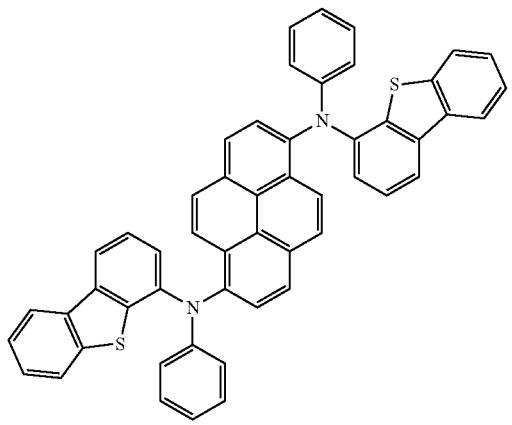
FD7
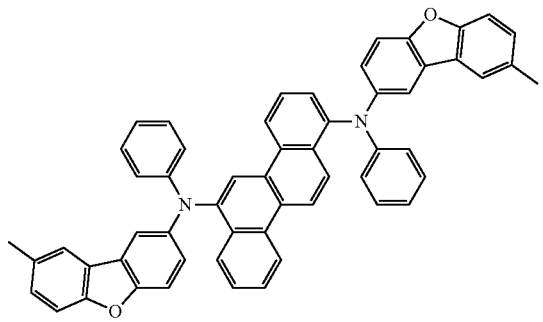
FD8
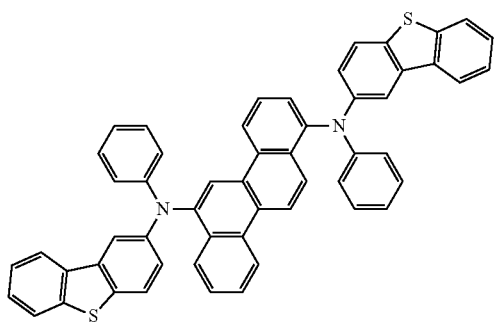
FD9
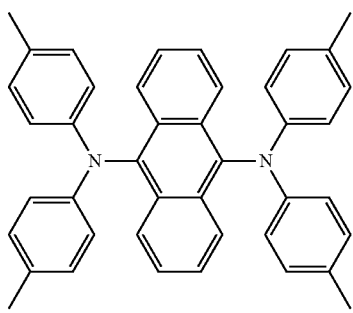

-continued

FD10
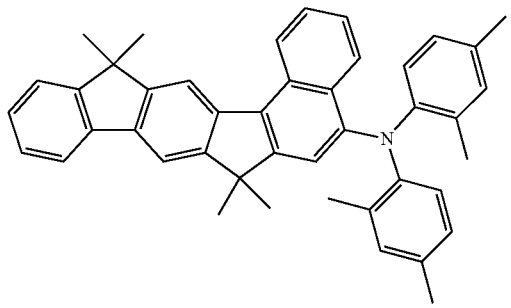

FD11
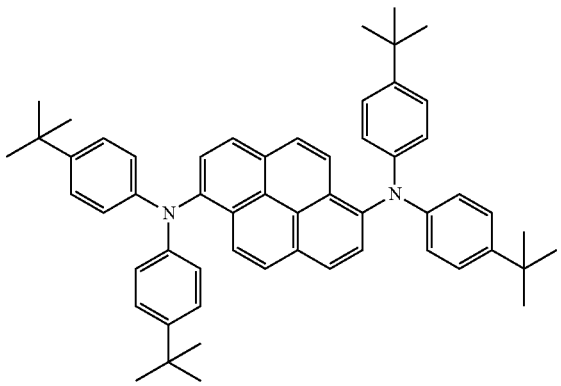

FD12
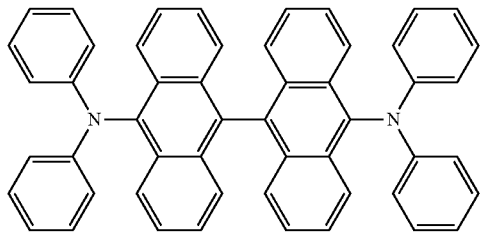

FD13
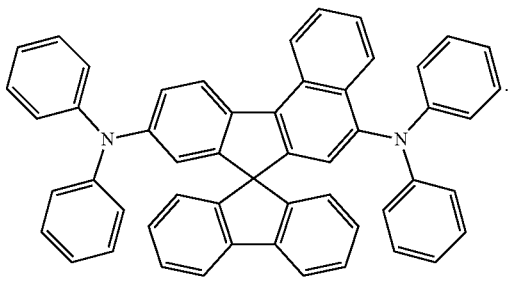

The term "organic layer" as used herein refers to a single layer and/or a plurality of layers disposed between the first electrode and the second electrode of the organic light-emitting device. The "organic layer" may include, in addition to an organic compound, an organometallic complex including metal.

The FIGURE is a schematic view of an organic light-emitting device 10 according to an embodiment. Hereinafter, the structure of an organic light-emitting device according to an embodiment and a method of manufacturing an organic light-emitting device according to an embodiment will be described in connection with the FIGURE. The organic light-emitting device 10 includes a first electrode 11, an organic layer 15, and a second electrode 19, which are sequentially stacked.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water resistance.

In one or more embodiments, the first electrode 11 may be formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode 11 may be indium tin oxide (ITO), indium zinc oxide (IZO), tin oxide ($SnO_2$), or zinc oxide (ZnO). In one or more embodiments, the material for forming the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layered structure or a multi-layered structure including two or more layers. For example, the first electrode 11 may have a three-layered structure of ITO/Ag/ITO, but the structure of the first electrode 110 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In one or more embodiments, the hole transport region may have a hole injection layer/hole transport layer structure or a hole injection layer/hole transport layer/electron blocking layer structure, which are sequentially stacked in this stated order from the first electrode 11.

When the hole transport region includes a hole injection layer (HIL), the hole injection layer may be formed on the first electrode 11 by using one or more suitable methods, for example, vacuum deposition, spin coating, casting, and/or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100 degrees Centigrade (° C.) to about 500° C., a vacuum pressure of about $10^{-8}$ torr to about $10^{-3}$ torr, and a deposition rate of about 0 Angstroms per second (Å/sec) to about 100 Å/sec. However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include at least one selected from m-MTDATA, TDATA, 2-TNATA, NPB, 8-NPB, TPD, Spiro-TPD, Spiro-NPB, METHYLATED-NPB, TAPC, HMTPD, 4,4',4''-tris(N-carbazolyl)triphenylamine (TCTA), polyaniline/dodecylbenzene sulfonic acid (PANI/DBSA), poly(3,4-ethylenedioxythiophene)/poly(4-styrene sulfonate) (PEDOT/PSS), polyaniline/camphor sulfonic acid (PANI/CSA), polyaniline/poly(4-styrene sulfonate) (PANI/PSS), a compound represented by Formula 201 below, and a compound represented by Formula 202 below:

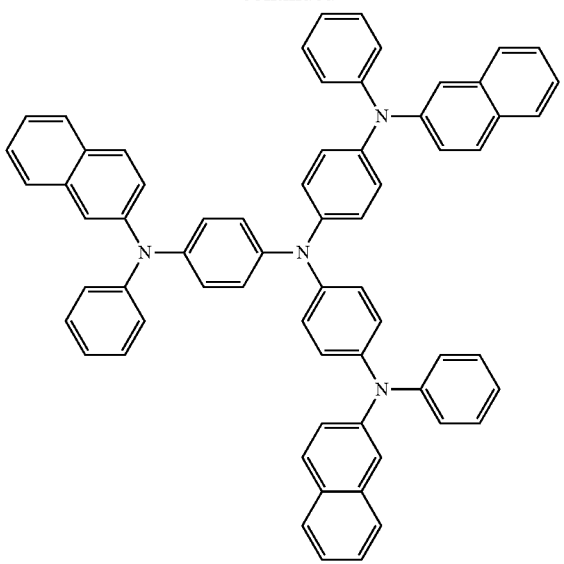

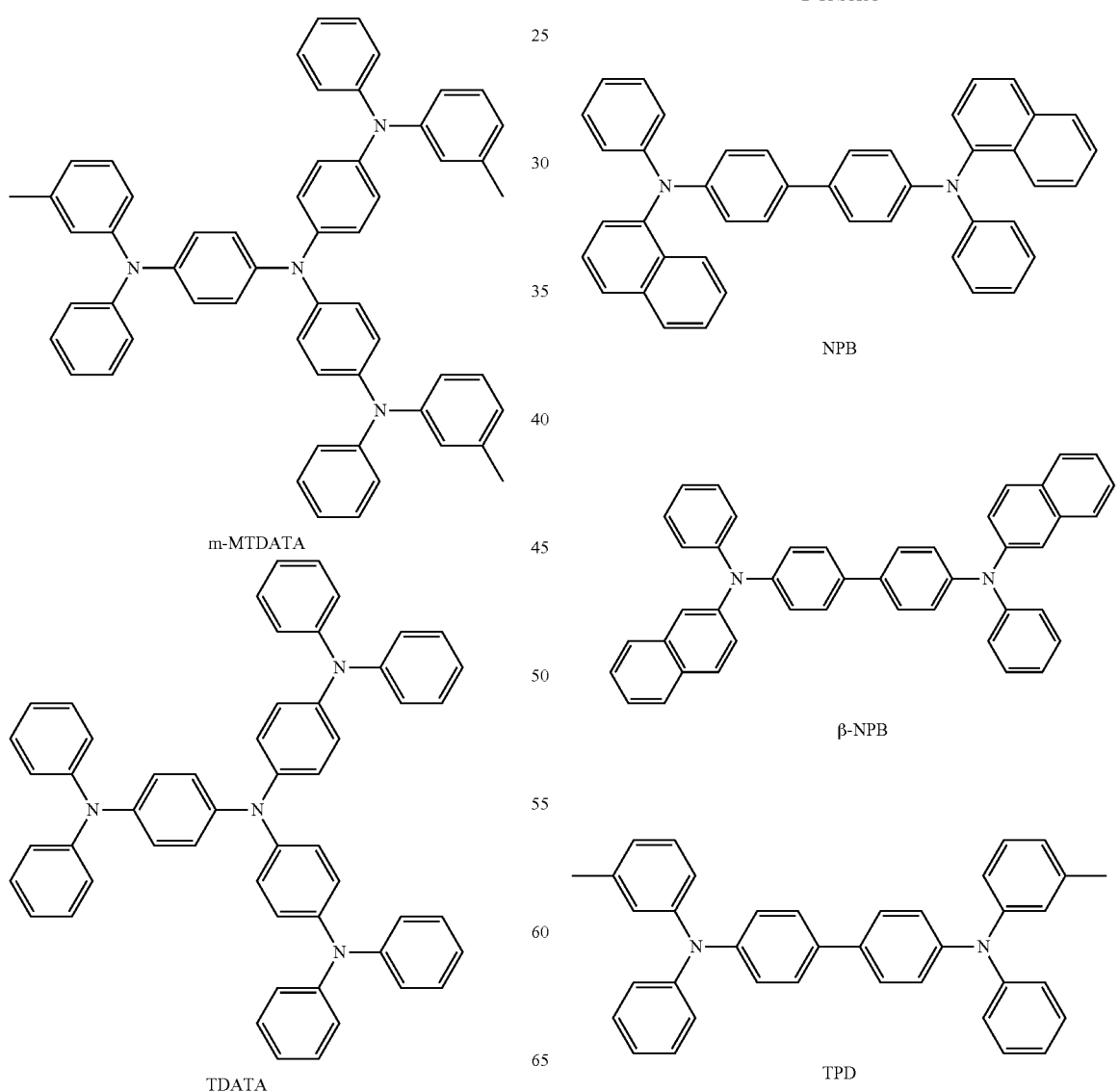

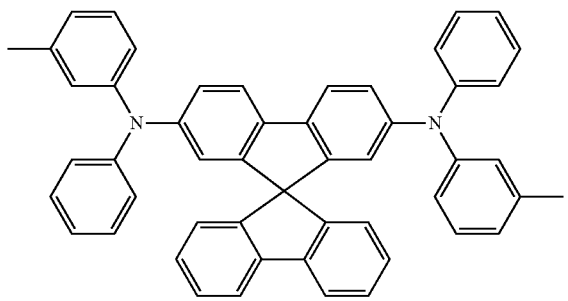

Spiro-TPD

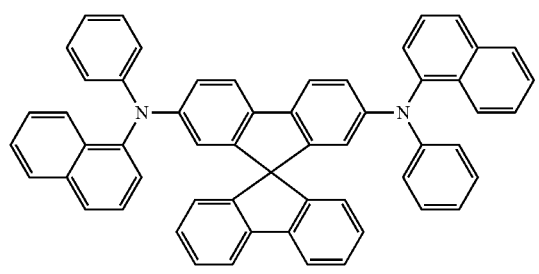

Spiro-NPB

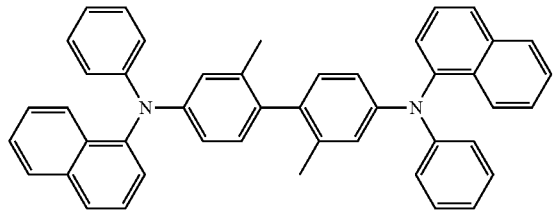

methylated NPB

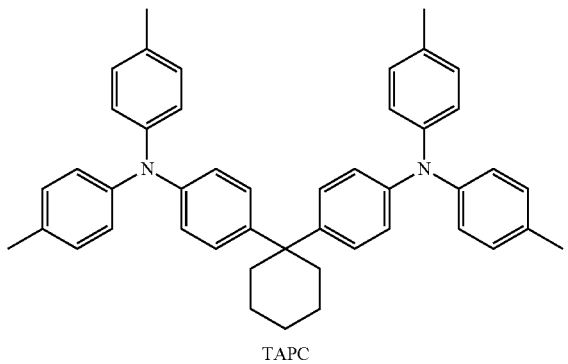

TAPC

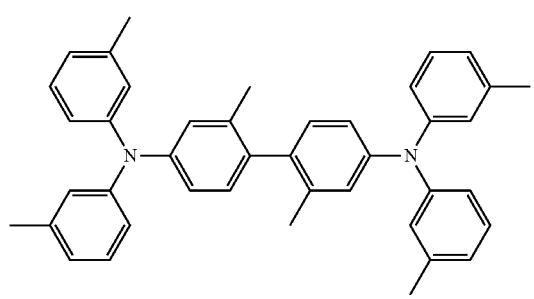

HMTPD

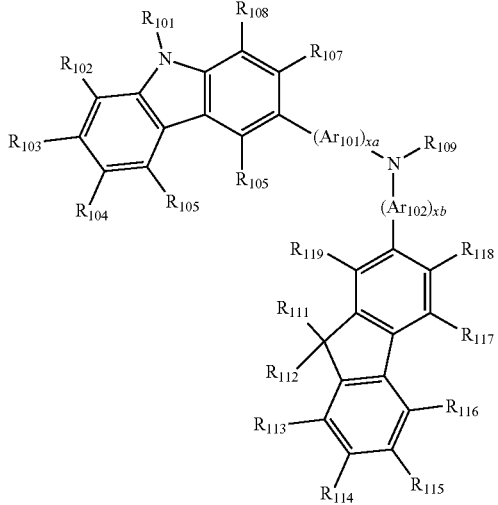

Formula 201

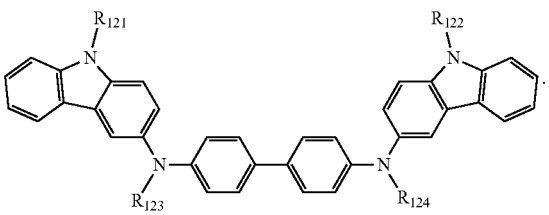

Formula 202

$Ar_{101}$ and $Ar_{102}$ in Formula 201 may each independently be selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may each independently be an integer from 0 to 5, or 0, 1 or 2. For example, xa may be 1 and xb may be 0, but xa and xb are not limited thereto.

In Formulae 201 and 202, $R_{101}$ to $R_{108}$, $R_{111}$ to $R_{119}$, and $R_{121}$ to $R_{124}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, pentyl group, and a hexyl group), and a $C_1$-$C_{10}$ alkoxy group (for example, a methoxy group, an ethoxy group, a propoxy group, a butoxy group, and a pentoxy group);

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, or a pyrenyl group; or a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

but embodiments of the present disclosure are not limited thereto.

$R_{109}$ in Formula 201 may be selected from:

a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

According to an embodiment, the compound represented by Formula 201 may be represented by Formula 201A below, but embodiments of the present disclosure are not limited thereto:

Formula 201A

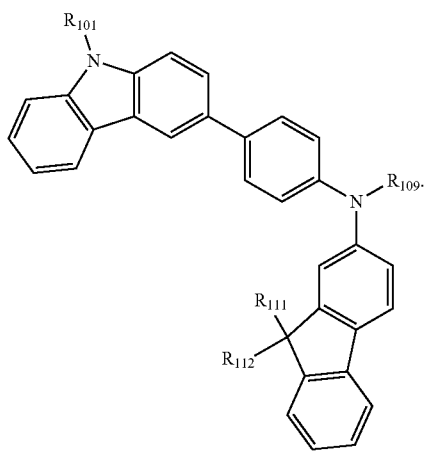

In Formula 201A, $R_{101}$, $R_{111}$, $R_{112}$, and $R_{109}$ may respectively be the same as described above.

For example, the compound represented by Formula 201, and the compound represented by Formula 202 may include compounds HT1 to HT20 illustrated below, but are not limited thereto.

HT1

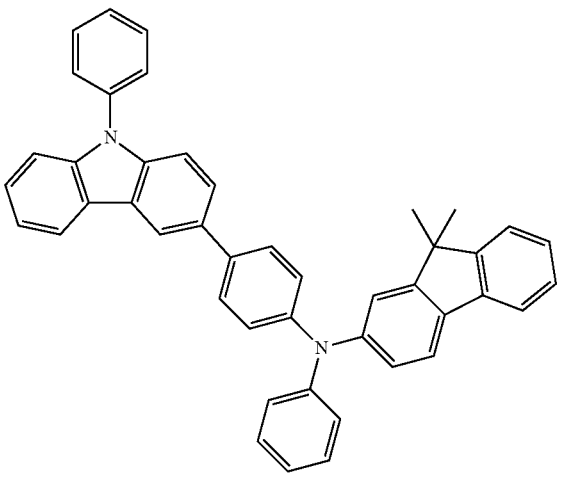

HT2

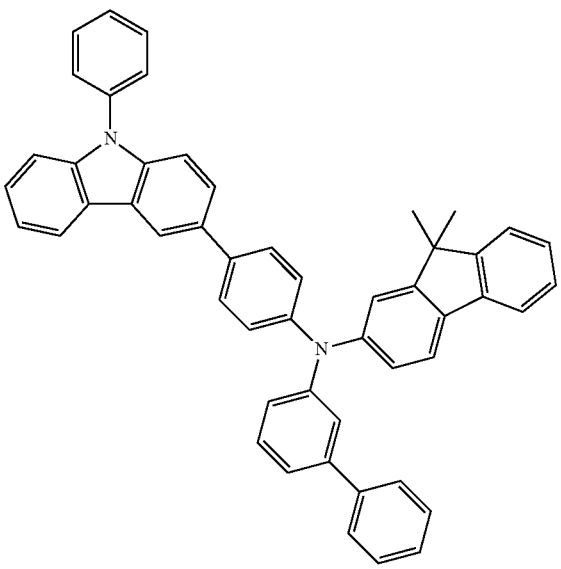

HT3
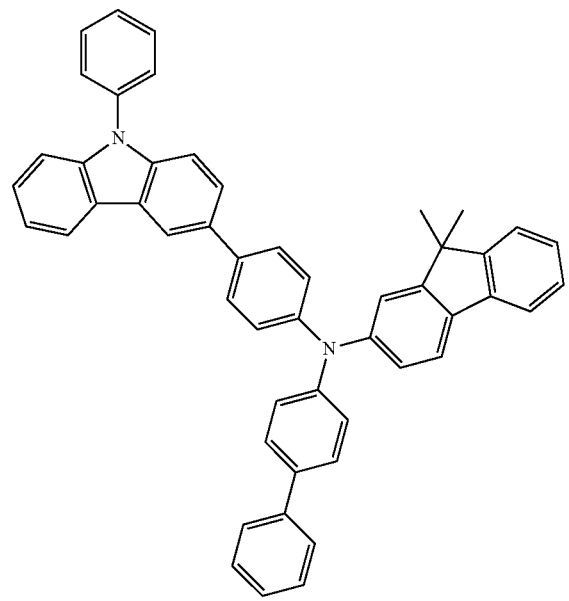
HT5
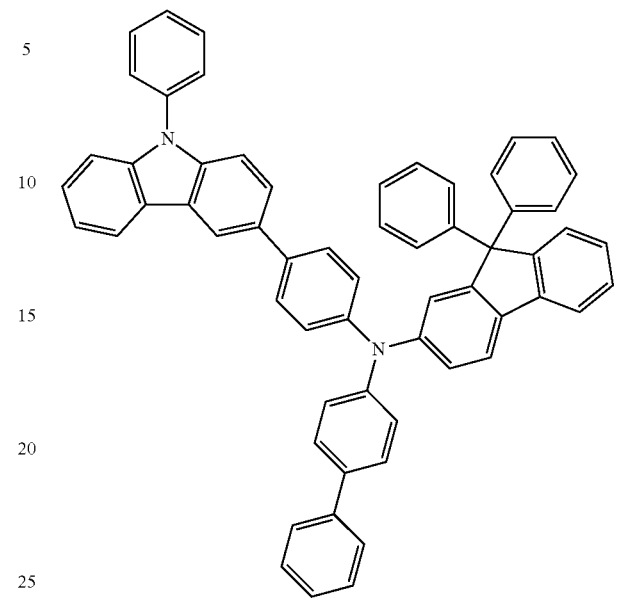
HT4
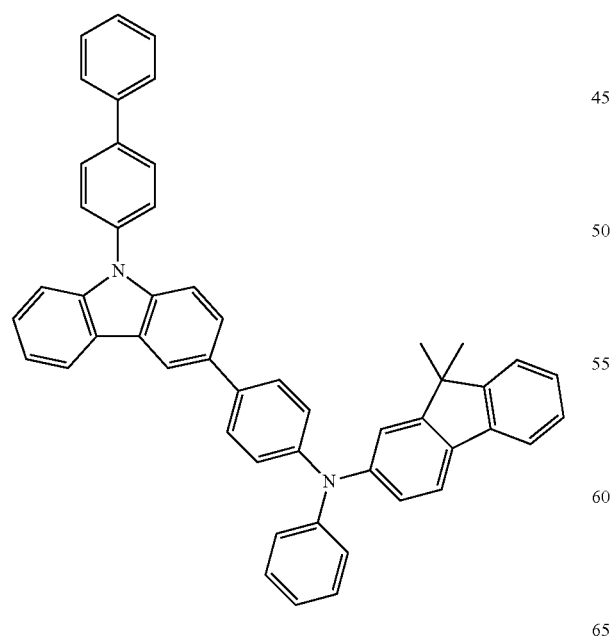
HT6
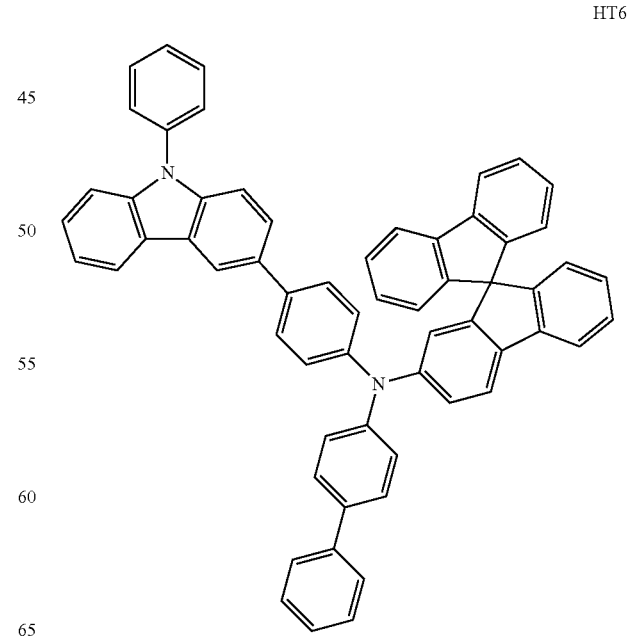

HT7
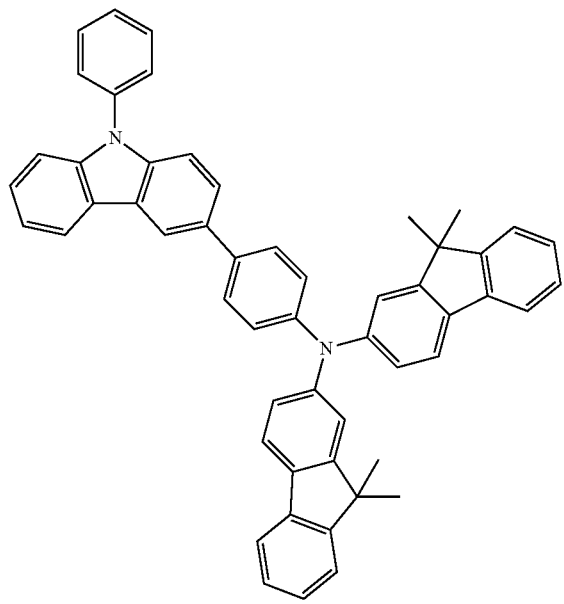
HT8
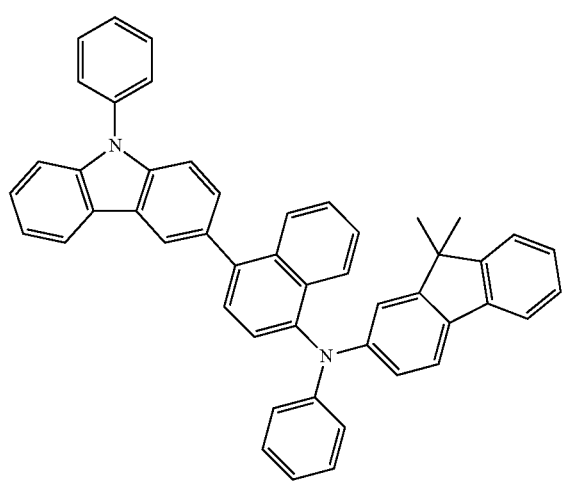
HT9
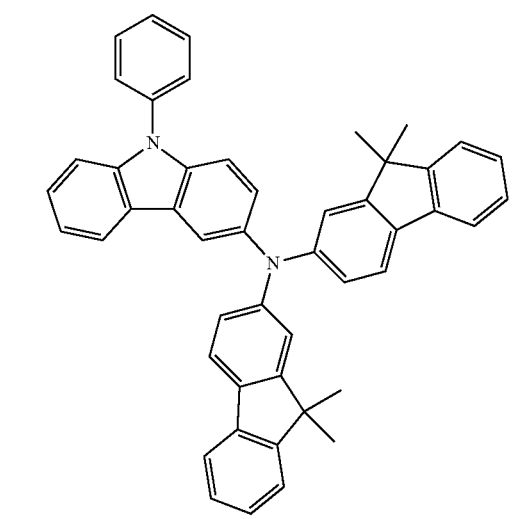
HT10
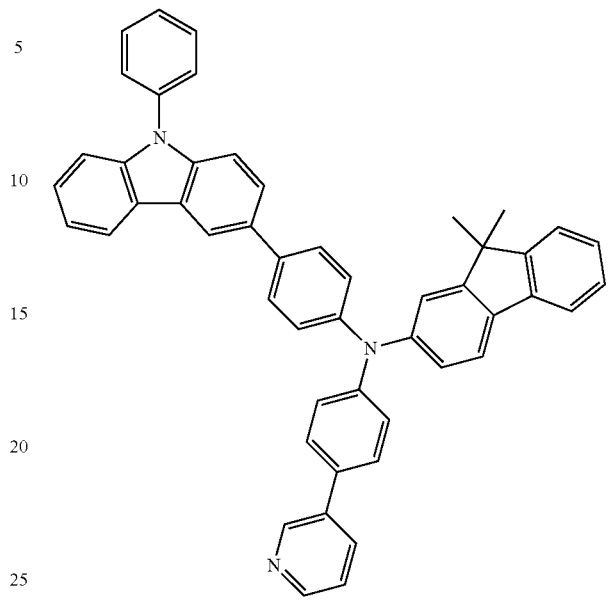
HT11
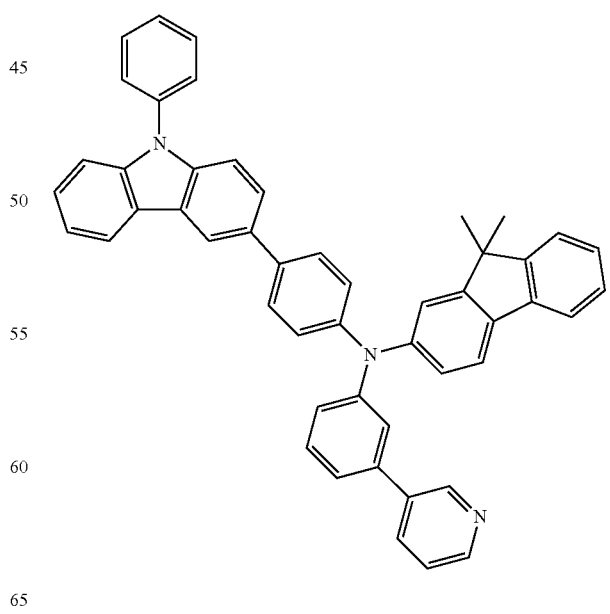

HT12
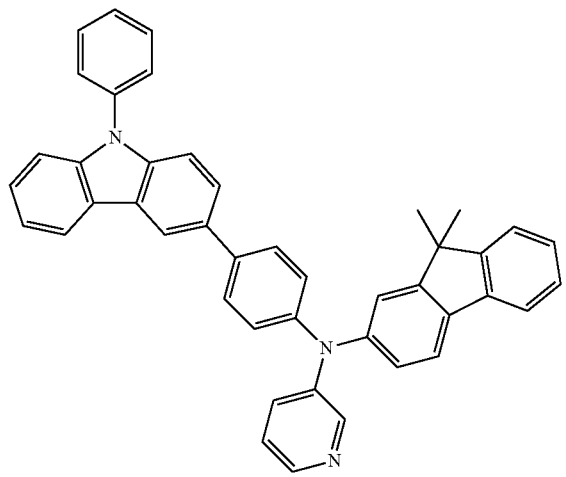
HT13
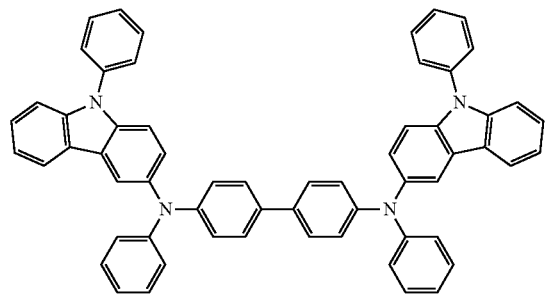
HT14
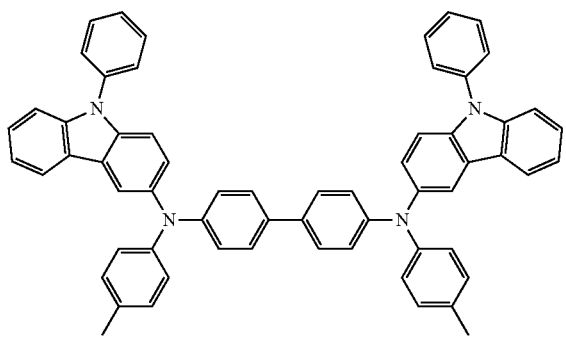
HT15
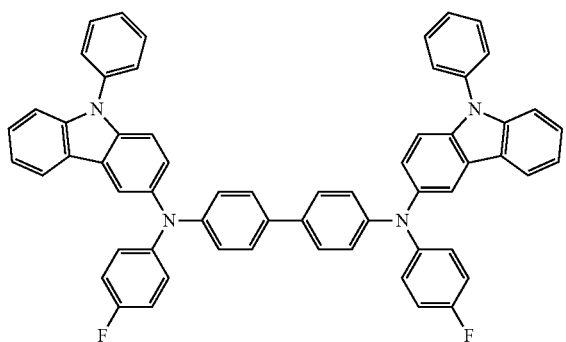
HT16
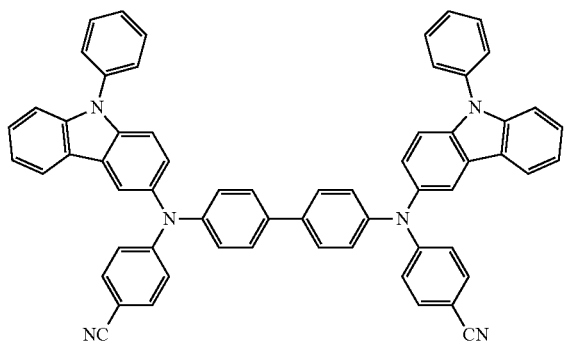
HT17
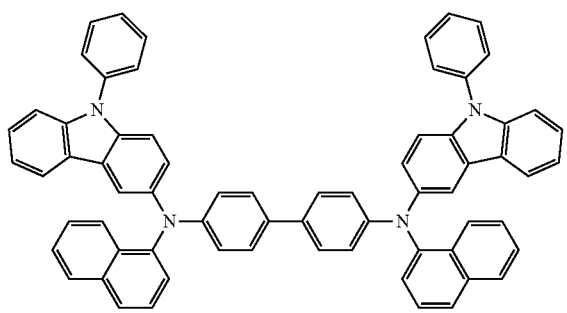
HT18
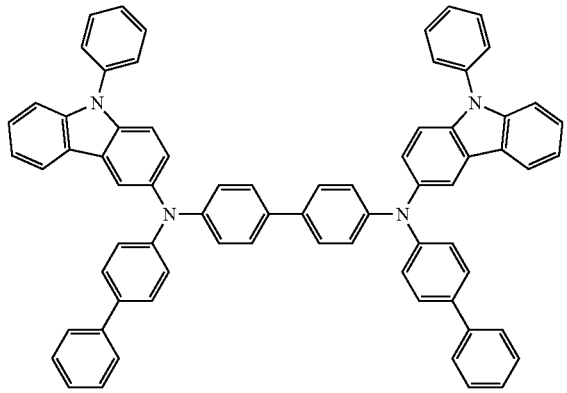
HT19
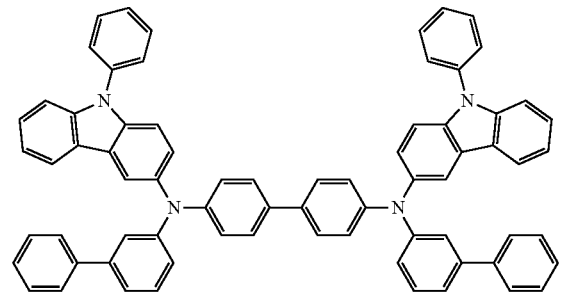

HT20

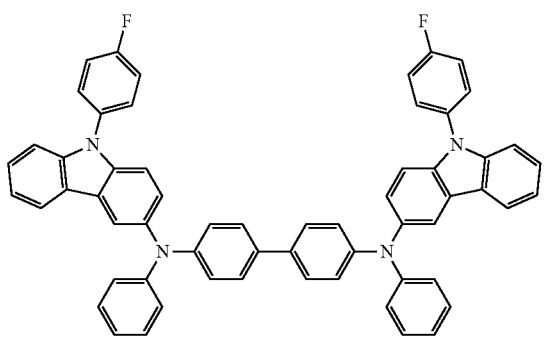

The hole transport layer may include the condensed cyclic compound represented by Formula 1.

A thickness of the hole transport region may be in a range of about 100 Angstroms (Å) to about 10,000 Å, for example, about 100 Å to about 1,000 Å. When the hole transport region includes at least one of a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example about 100 Å to about 1,500 Å. While not wishing to be bound by theory, it is understood that when the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments of the present disclosure are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a cyano group-containing compound, such as Compound HT-D1 or HP-1, but are not limited thereto.

Compound HT-D1

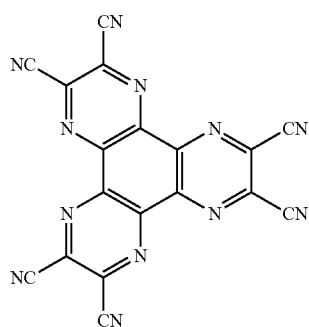

F4-TCNQ

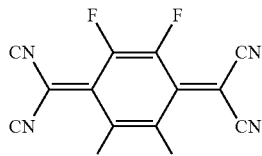

HP-1

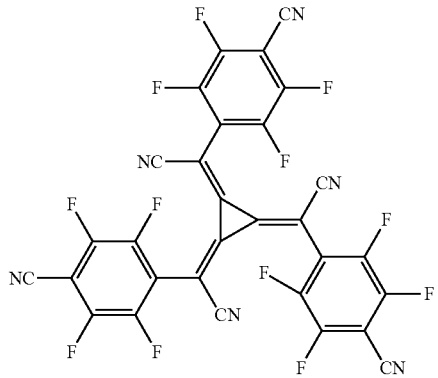

The hole transport region may include a buffer layer. Also, the buffer layer may compensate for an optical resonance distance according to a wavelength of light emitted from the emission layer, and thus, efficiency of a formed organic light-emitting device may be improved.

Then, an emission layer may be formed on the hole transport region by vacuum deposition, spin coating, casting, LB deposition, or the like. When the emission layer is formed by vacuum deposition or spin coating, the deposition or coating conditions may be similar to those applied in forming the hole injection layer although the deposition or coating conditions may vary according to a compound that is used to form the emission layer.

The electron transport region may further include an electron blocking layer. The electron blocking layer may include, for example, mCP, but a material therefor is not limited thereto.

mCP

For example, the hole transport region may include the electron blocking layer, wherein the electron blocking layer includes the condensed cyclic compound represented by Formula 1.

A thickness of the electron blocking layer may be in a range of about 50 Å to about 1,000 Å, for example, about 70 Å to about 500 Å. While not wishing to be bound by theory, it is understood that when the thickness of the electron blocking layer is within the range described above, the electron blocking layer may have satisfactory electron blocking characteristics without a substantial increase in driving voltage.

When the organic light-emitting device is a full-color organic light-emitting device, the emission layer may be patterned into a red emission layer, a green emission layer, and a blue emission layer. In one or more embodiments, due to a stacked structure including a red emission layer, a green emission layer, and/or a blue emission layer, the emission layer may emit white light.

The emission layer may include the condensed cyclic compound represented by Formula 1. For example, the emission layer may include the compound represented by Formula 1 alone. In one or more embodiment, the emission layer may include a host and a dopant, and the host may include the condensed cyclic compound represented by Formula 1. In one or more embodiment, the emission layer may include a host and a dopant, and the dopant may include the condensed cyclic compound represented by Formula 1.

In one or more embodiment, the dopant in the emission layer may be a phosphorescent dopant, and the phosphorescent dopant may include an organometallic compound represented by Formula 81 below:

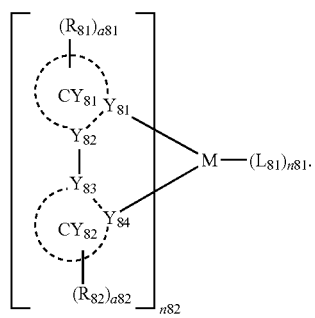

Formula 81

In Formula 81,

M may be selected from iridium (Ir), platinum (Pt), osmium (Os), titanium (Ti), zirconium (Zr), hafnium (Hf), europium (Eu), terbium (Tb), thulium (Tm), rhenium (Re), and rhodium (Rh), $Y_{81}$ to $Y_{84}$ may each independently be carbon (C) or nitrogen (N), $Y_{81}$ and $Y_{82}$ may be linked via a single bond or a double bond, and $Y_{83}$ and $Y_{84}$ may be linked via a single bond or a double bond, $CY_{81}$ and $CY_{82}$ may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group, $CY_{81}$ and $CY_{82}$ may further optionally be linked via an organic linking group, $R_{81}$ and $R_{82}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), and —B(Q$_6$)(Q$_7$), $a_{81}$ and $a_{82}$ may each independently be an integer of 1 to 5, $n_{81}$ may be an integer of 0 to 4, $n_{82}$ may be 1, 2, or 3, $L_{81}$ may be a monovalent organic ligand, a divalent organic ligand, or a trivalent organic ligand, and $Q_1$ to $Q_7$ may respectively be the same as described in connection with $Q_1$ to $Q_3$ of Si(Q$_1$)(Q$_2$)(Q$_3$) in Formula 1.

$R_{81}$ and $R_{82}$ may respectively be the same as described in connection with $R_{11}$.

The phosphorescent dopant may include at least one selected from Compounds PD1 to PD78 and FIr$_6$, but embodiments of the present disclosure are not limited thereto:

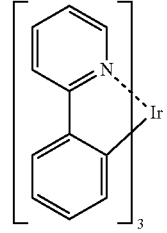

PD1

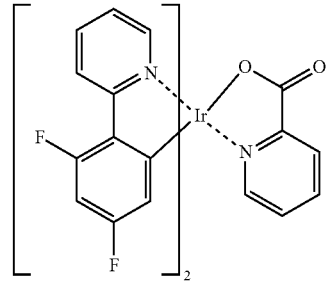

PD2

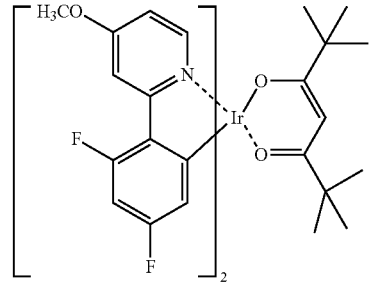

PD3

101
-continued
PD4
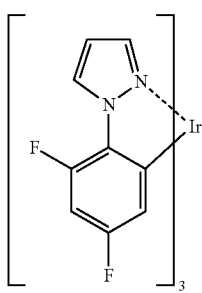
PD5
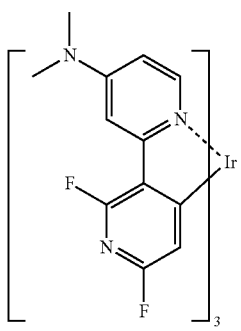
PD6
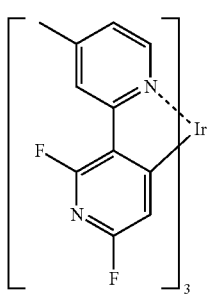
PD7
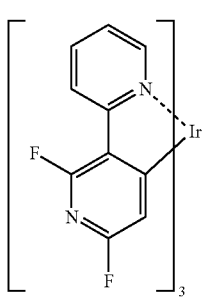
PD8
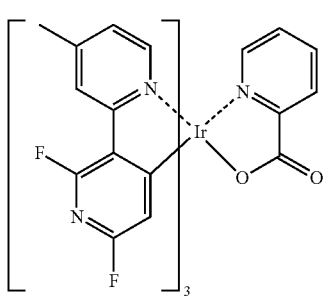
102
-continued
PD9
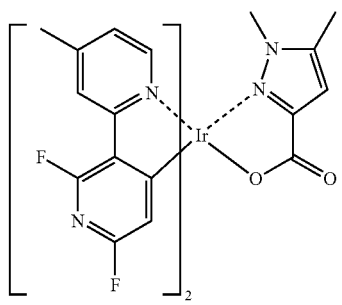
PD10
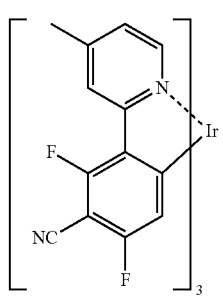
PD11
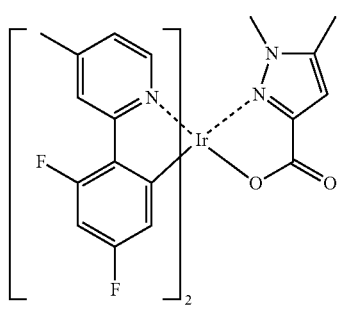
PD12
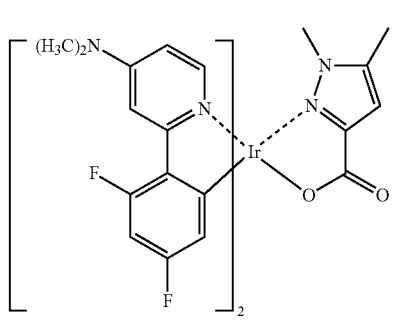
PD13
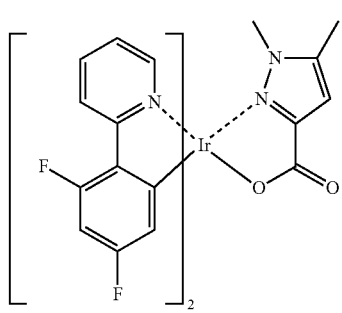

-continued
PD14
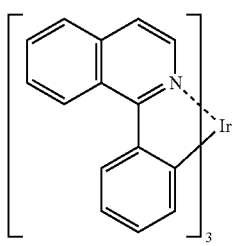
PD15
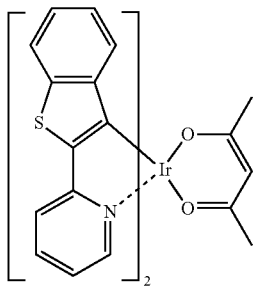
PD16
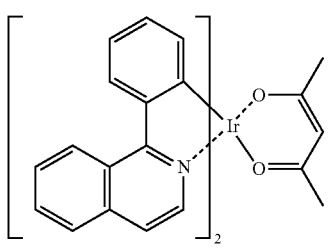
PD17
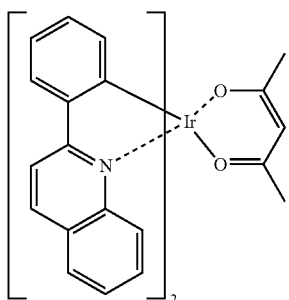
PD18
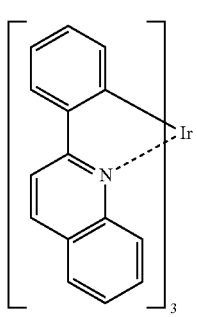
-continued
PD19
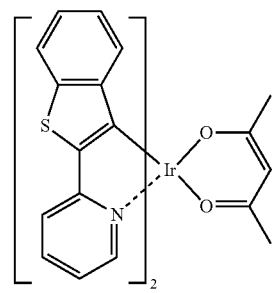
PD20
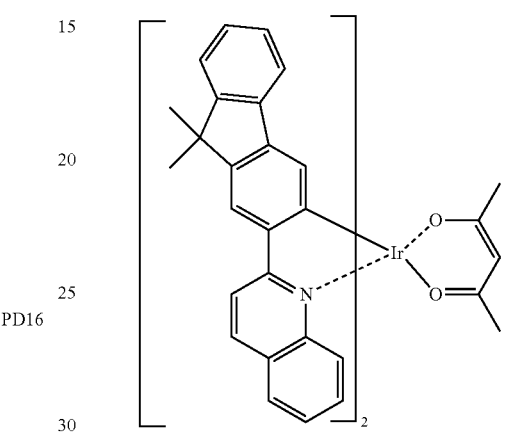
PD21
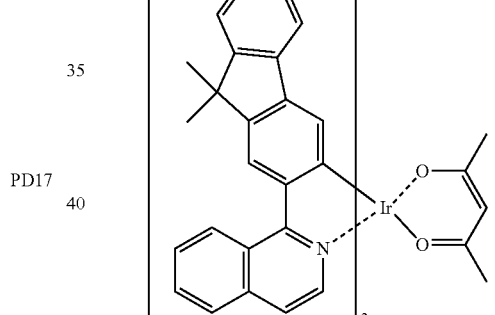
PD22
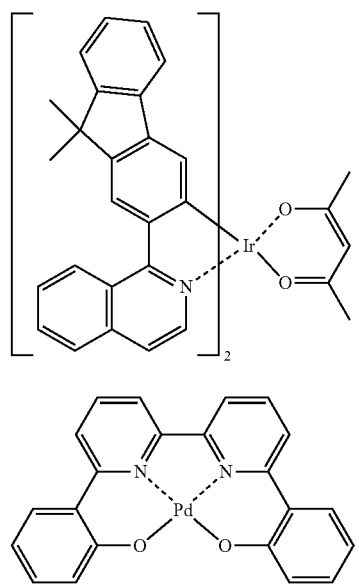
PD23
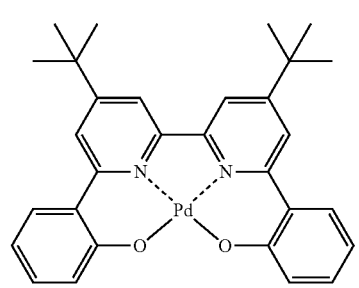

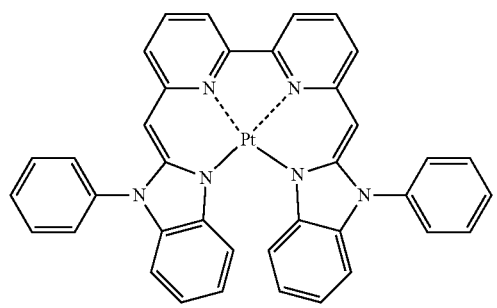
PD24
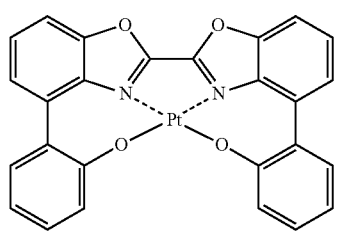
PD25
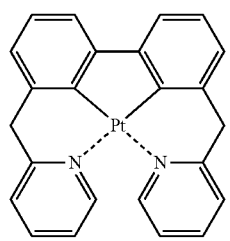
PD26
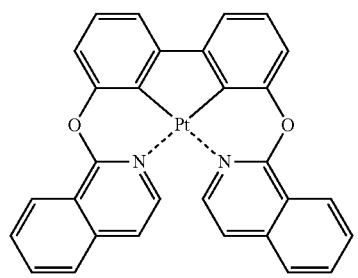
PD27
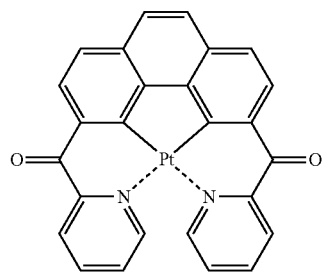
PD28
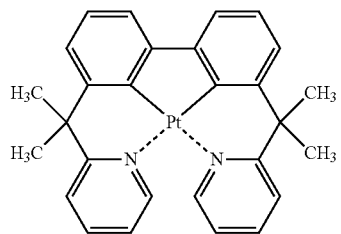
PD29
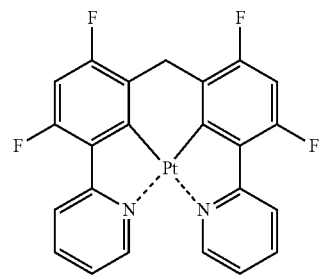
PD30
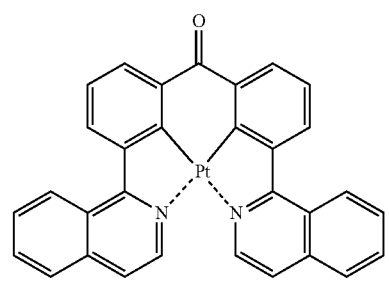
PD31
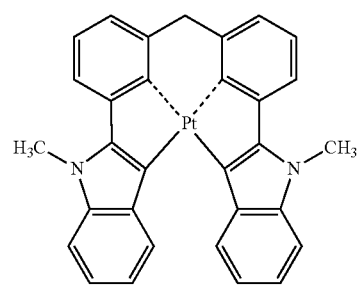
PD32
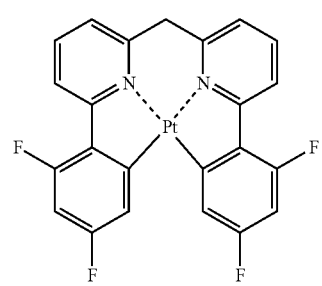
PD33
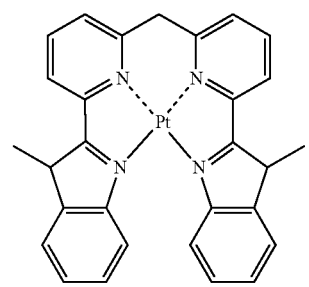
PD34

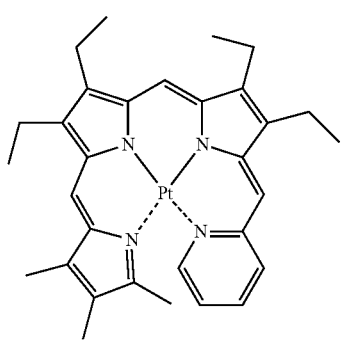
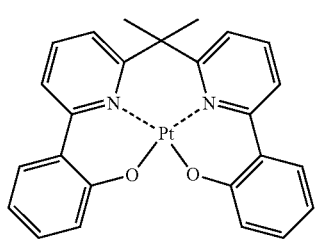
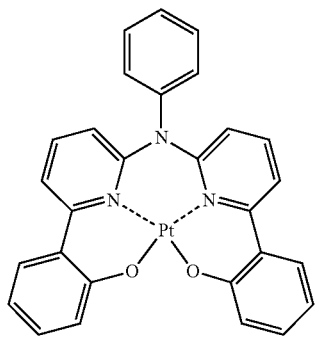
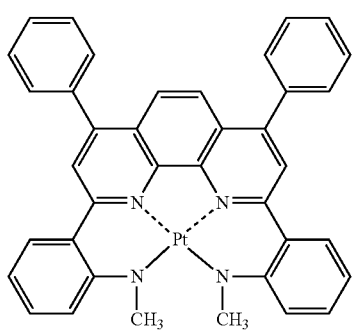
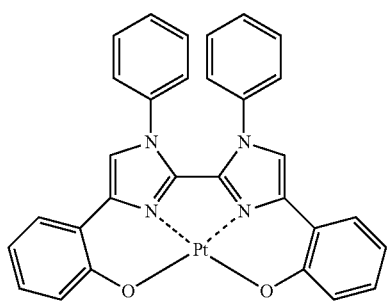
PD35
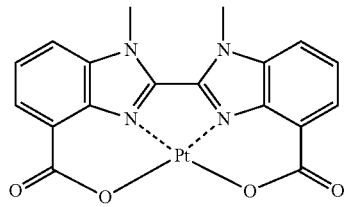
PD36
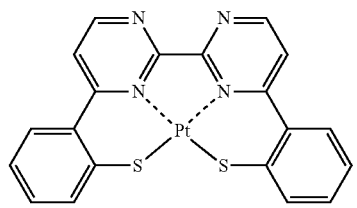
PD37
PD38
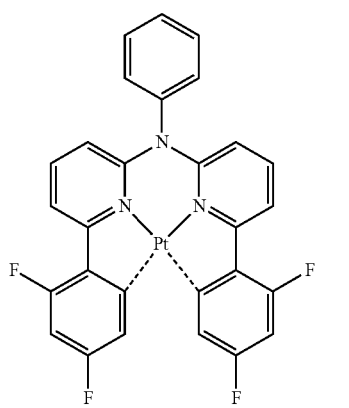
PD39
PD40
PD41
PD42
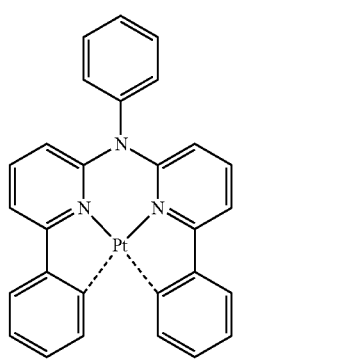
PD43
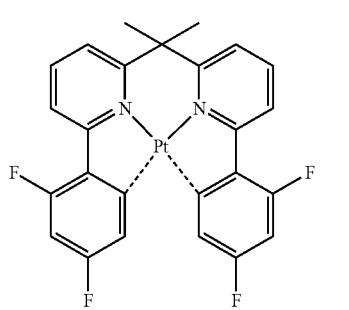
PD44

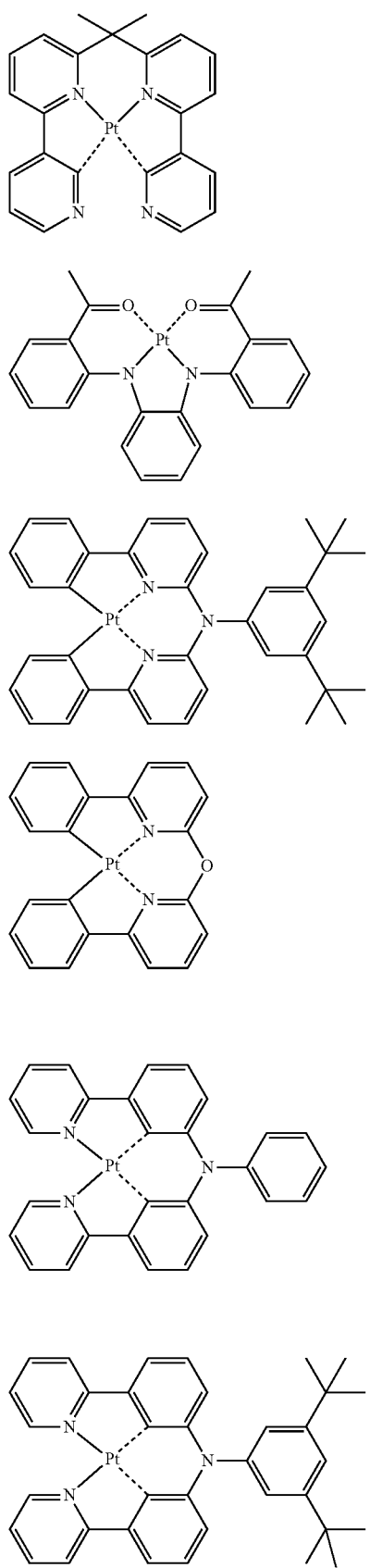
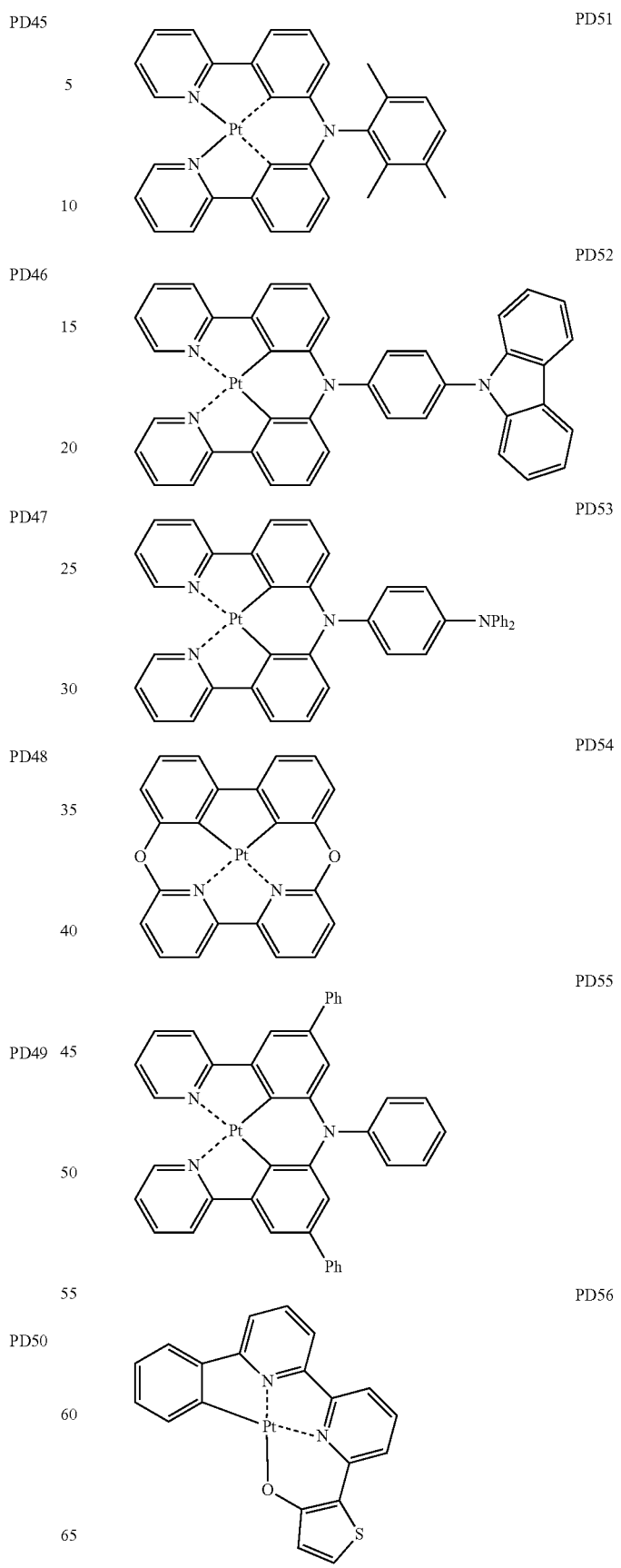

PD57 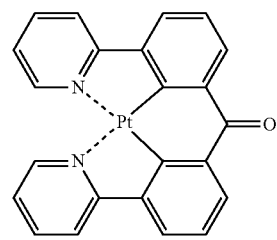
PD58 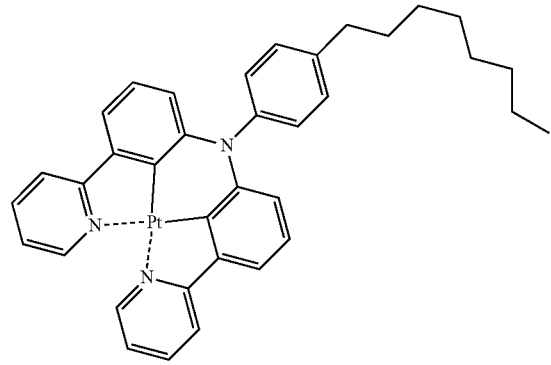
PD59 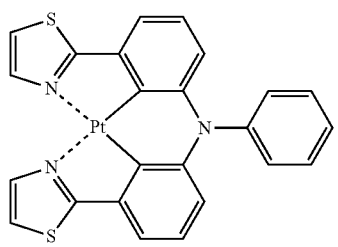
PD60 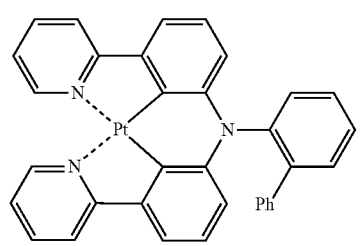
PD61 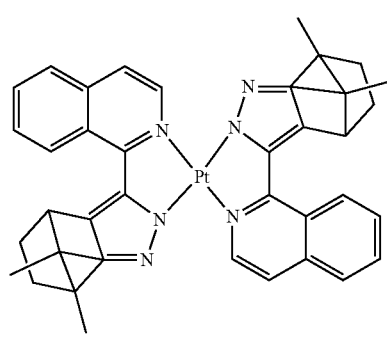
PD62 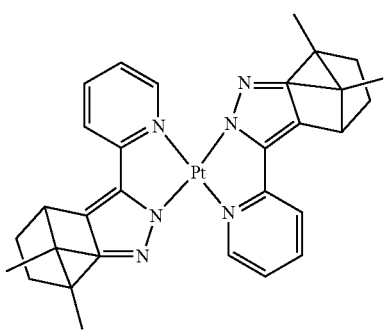
PD63 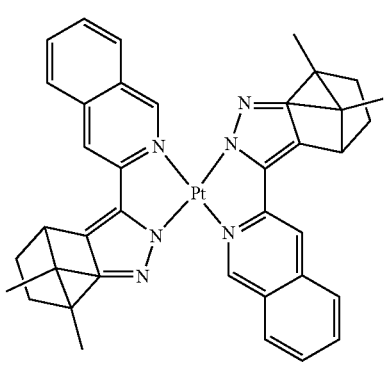
PD64 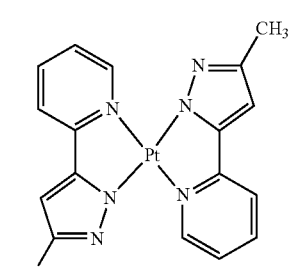
PD65 
PD66 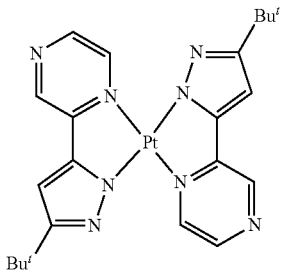

PD67 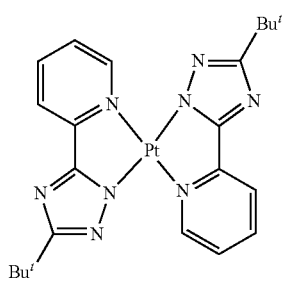
PD68 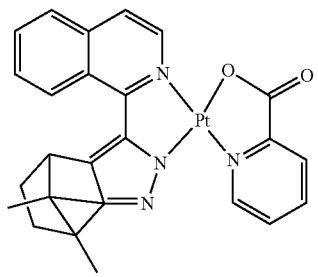
PD69 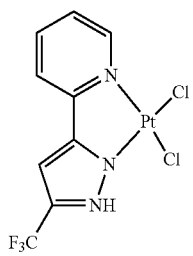
PD70 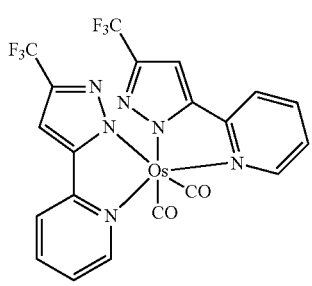
PD71 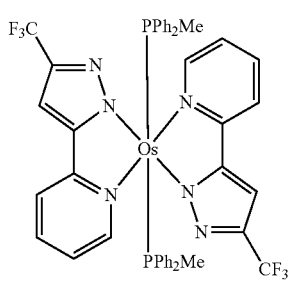
PD72 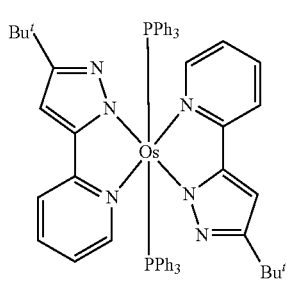
PD73 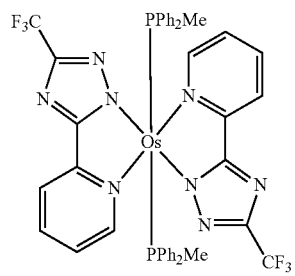
PD74 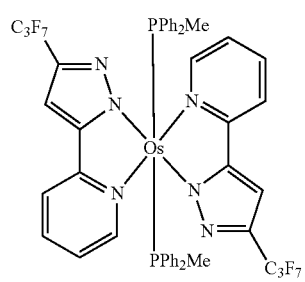
PD75 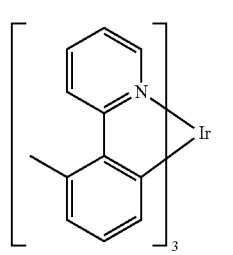
PD76 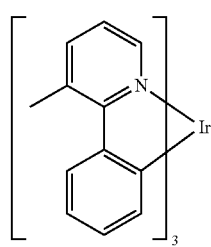
PD77 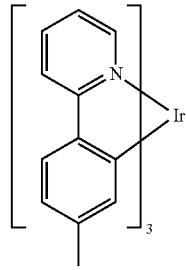
PD78 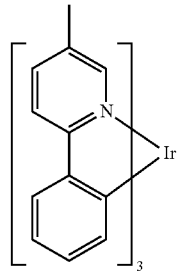

-continued

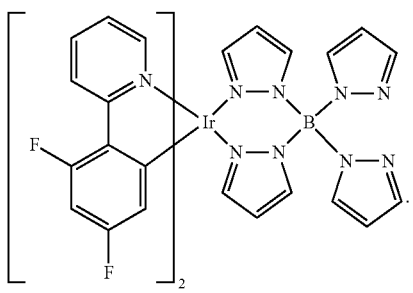

Flr6

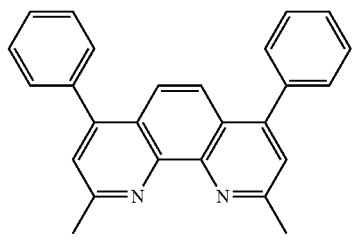

BCP

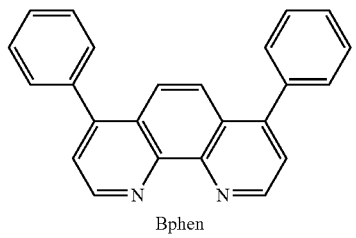

Bphen

In one or more embodiments, the phosphorescent dopant may include PtOEP:

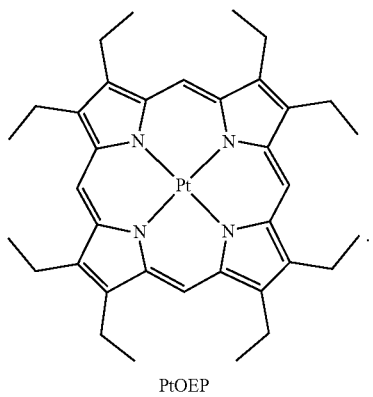

PtOEP

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, the hole blocking layer may have excellent hole blocking characteristics without a substantial increase in driving voltage.

The electron transport layer may further include, in addition to the organometallic compound represented by Formula 1, at least one selected from BCP, Bphen, Alq$_3$, BAlq, TAZ, and NTAZ.

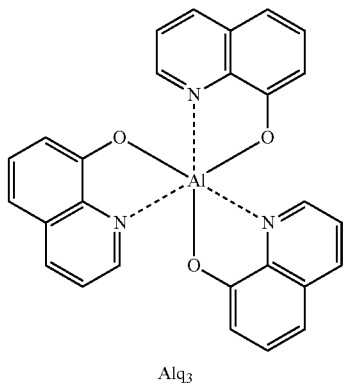

Alq$_3$

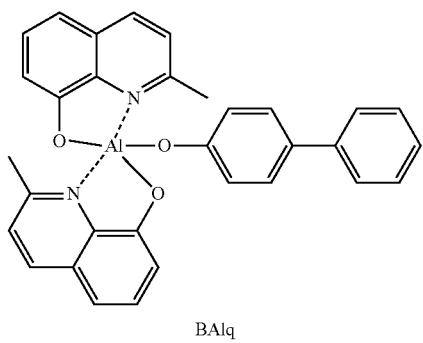

BAlq

When the emission layer includes a host and a dopant, an amount of the dopant may be in a range of about 0.01 parts by weight to about 20 parts by weight based on 100 parts by weight of the host, but embodiments of the present disclosure are not limited thereto.

A thickness of the emission layer may be in a range of about 100 Å to about 1,000 Å, for example, about 200 Å to about 600 Å. While not wishing to be bound by theory, it is understood that when the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a hole blocking layer/electron transport layer/electron injection layer structure or an electron transport layer/electron injection layer structure, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one of BCP and Bphen, but may also include other materials.

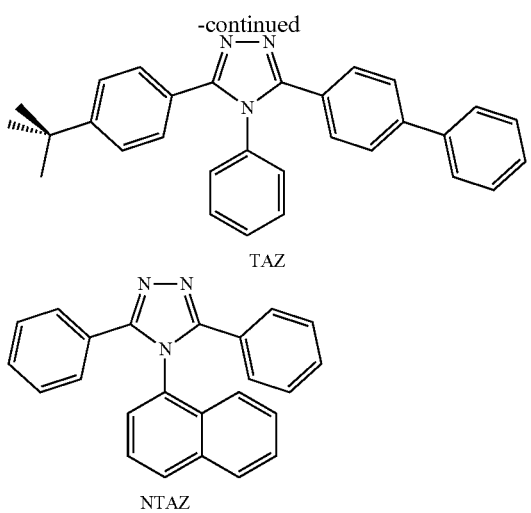

TAZ

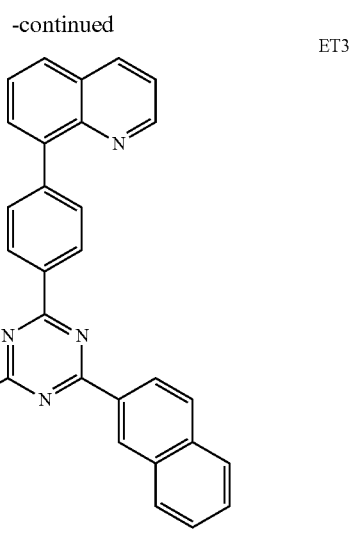

ET3

NTAZ

In one or more embodiments, the electron transport layer may include at least one selected from Compounds ET1, ET2, and ET3, but embodiments of the present disclosure are not limited thereto:

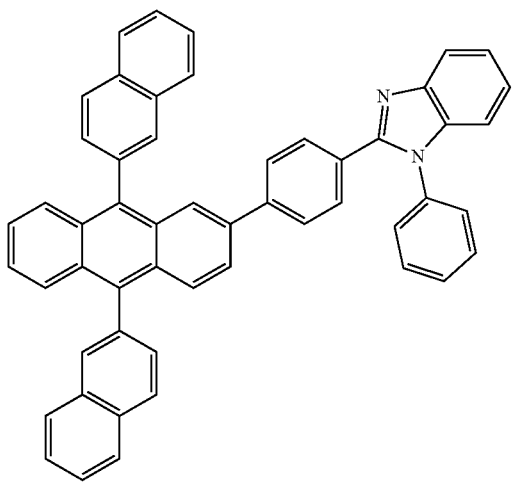

ET1

A thickness of the electron transport layer may be in a range of about 100 Å to about 1,000 Å, for example, about 150 Å to about 500 Å. While not wishing to be bound by theory, it is understood that when the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (8-hydroxylithium quinolate, LiQ) or ET-D2.

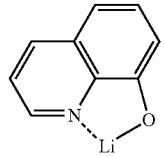

ET-D1

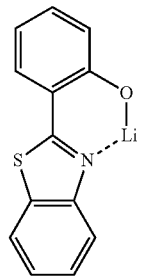

ET-D2

ET2

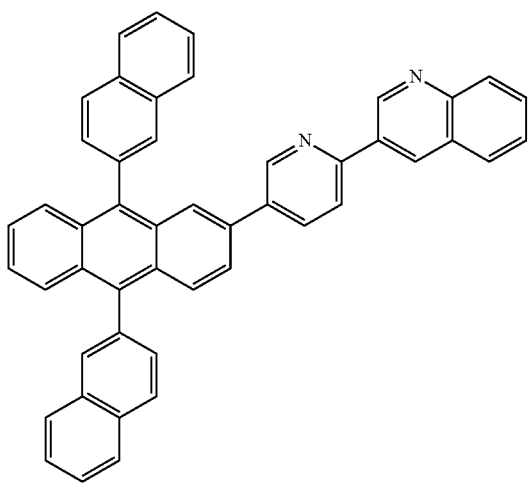

The electron transport region may include an electron injection layer (EIL) that promotes flow of electrons from the second electrode 19 thereinto.

The electron injection layer may include at least one selected from LiQ, LiF, NaCl, CsF, $Li_2O$, and BaO.

A thickness of the electron injection layer may be in a range of about 1 Å to about 100 Å, for example, about 3 Å to about 90 Å. While not wishing to be bound by theory, it is understood that when the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be metal, an alloy, an electrically conductive compound, or a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as the material for forming the second electrode 19. To manufacture a top-emission type light-emitting device, a transmissive electrode formed using ITO or IZO may be used as the second electrode 19.

In an embodiment, the organic layer 15 of the organic light-emitting device 10 may include a hole transport region and an emission layer. The hole transport region and the emission layer may include the condensed cyclic compound represented by Formula 1. The condensed cyclic compound represented by Formula 1 included in the hole transport region and the condensed cyclic compound represented by Formula 1 included in the emission layer may be identical to each other.

In one or more embodiments, the organic layer 15 of the organic light-emitting device 10 may include a hole transport region and an emission layer, and the hole transport region and the emission layer may include the condensed cyclic compound represented by Formula 1, wherein the condensed cyclic compound represented by Formula 1 included in the hole transport region may be different from the condensed cyclic compound represented by Formula 1 included in the emission layer.

Here, the hole transport region may include at least one selected from a hole transport layer and an electron blocking layer, and the condensed cyclic compound represented by Formula 1 may be included in i) the hole transport layer, ii) the electron blocking layer or iii) both the hole transport layer and the electron blocking layer. The electron blocking layer may directly contact the emission layer.

Hereinbefore, the organic light-emitting device has been described with reference to the FIGURE, but embodiments of the present disclosure are not limited thereto.

The term "$C_1$-$C_{60}$ alkyl group" as used herein refers to a linear or branched aliphatic saturated hydrocarbon monovalent group having 1 to 60 carbon atoms, and examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an iso-propyloxy group.

The term "$C_2$-$C_{60}$ alkenyl group" as used herein refers to a hydrocarbon group having at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group having at least one heteroatom selected from N, O, P, Si and S as a ring-forming atom and 1 to 10 carbon atoms, and non-limiting examples thereof include a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and no aromaticity, and non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, P, Si, and S as a ring-forming atom, 1 to 10 carbon atoms, and at least one carbon-carbon double bond in its ring. Non-limiting examples of the $C_2$-$C_{10}$ heterocycloalkenyl group include a 2,3-dihydrofuranyl group, and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a heterocyclic aromatic system that has at least one heteroatom selected from N, O, P, and S as a ring-forming atom, and 1 to 60 carbon atoms. The term $C_1$-$C_{60}$ heteroarylene group" as used herein refers to a divalent group having a heterocyclic aromatic system that has at least one heteroatom selected from N, O, P, and S as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group" as used herein refers to —$OA_{102}$ (wherein $A_{102}$ is the $C_6$-$C_{60}$ aryl group), and a $C_6$-$C_{60}$ arylthio group as used herein indicates —$SA_{103}$ (wherein $A_{103}$ is the $C_6$-$C_{60}$ aryl group).

The term "monovalent non-aromatic condensed polycyclic group" as used herein refers to a monovalent group having two or more rings condensed to each other, only carbon atoms (for example, the number of carbon atoms may be in a range of 8 to 60) as a ring-forming atom, and no aromaticity in its entire molecular structure. Non-limiting examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group having two or more rings condensed to each other, a heteroatom selected from N, O, P, Si, and S, other than carbon atoms (for example, the number of carbon atoms may be in a range of 2 to 60), as a ring-forming atom, and no aromaticity in its entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

In Formula 1 throughout the present specification, at least one substituent of the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —$CD_3$, —$CD_2H$, —$CDH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_{60}$ alkoxy group, each substituted with at least one selected from deuterium, —$CD_3$, —$CD_2H$, —$CDH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{14})(Q_{15})$, and —$B(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —$CD_3$, —$CD_2H$, —$CDH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{24})(Q_{25})$, and —$B(Q_{26})(Q_{27})$; and —$Si(Q_{31})(Q_{32})(Q_{33})$, —$N(Q_{34})(Q_{35})$, and —$B(Q_{36})(Q_{37})$, and $Q_1$ to $Q_7$, $Q_{11}$ to $Q_{17}$, $Q_{21}$ to $Q_{27}$, and $Q_{31}$ to $Q_{37}$ may each independently be selected from hydrogen, deuterium, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

The term "biphenyl group" refers to a monovalent group in which two benzene groups are linked via a single bond.

The term "terphenyl group" refers to a monovalent group in which three benzene groups are linked via a single bond.

Hereinafter, a compound and an organic light-emitting device according to embodiments are described in detail with reference to Synthesis Example and Examples. However, the organic light-emitting device is not limited thereto. The wording "'B' was used instead of 'A'" used in describing Synthesis Examples means that a molar equivalent of 'A' was identical to a molar equivalent of 'B'.

EXAMPLES

Synthesis Example 1: Synthesis of Compound 41

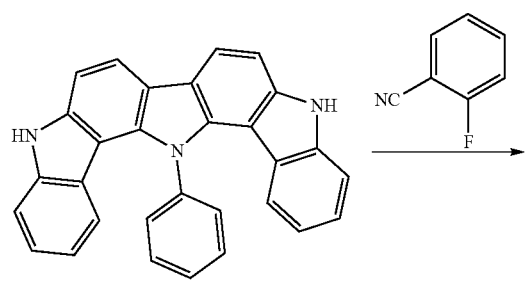
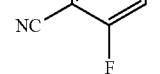

41

3.55 grams (g) of (8.42 moles, mol) of 15-phenyl-10,15-dihydro-5H-pyrrolo[3,2-c:4,5-c']dicarbazole was dissolved in 42 milliliters (mL) of DMF, and NaH was added to a flask. Then, the reaction mixture was stirred for 30 minutes. 2.45 g of (20.20 millimoles, mmol) of 2-fluorobenzonitrile was additionally added thereto and the reaction mixture underwent a reaction at a temperature of 80° C. for 8 hours. A product was obtained by filtering a precipitate by using methanol and column-purified by using CH₂Cl₂ and EA to obtain 3.9 g of Compound 41 (yield: 74%).
MALDI-MS Calcd: 623.21, Found: 624.2.

Synthesis Example 2: Synthesis of Compound 84

(1) Synthesis of Intermediate I-1

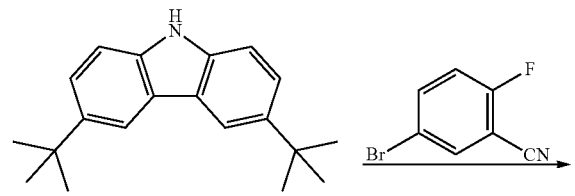
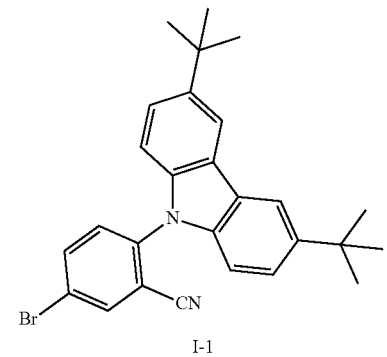

I-1

8.95 g of Intermediate I-1 (yield: 82%) was synthesized in the same manner as in Synthesis of Compound 41 in Synthesis Example 1, except that tert-butyl carbazole was used instead of 15-phenyl-10,15-dihydro-5H-pyrrolo[3,2-c:4,5-c']dicarbazole, and 5-bromo-2-fluorobenzonitrile was used instead of 2-fluorobenzonitrile.
MALDI-MS Calcd: 458.14, Found: 459.1.

(2) Synthesis of Compound 84

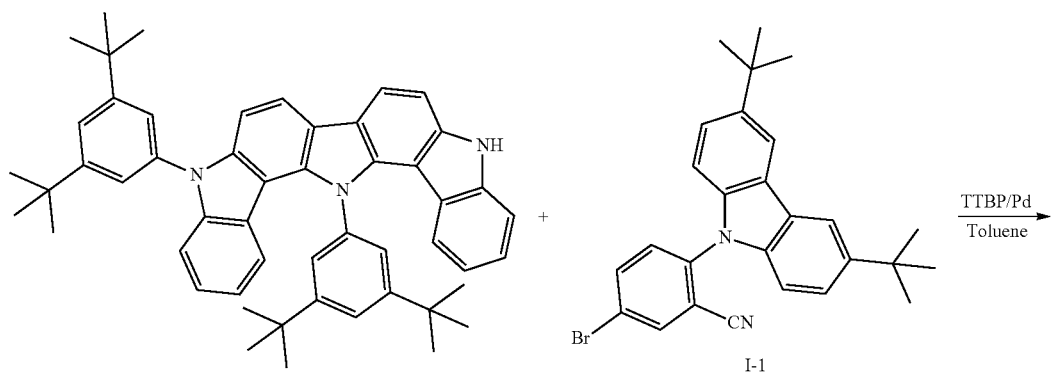

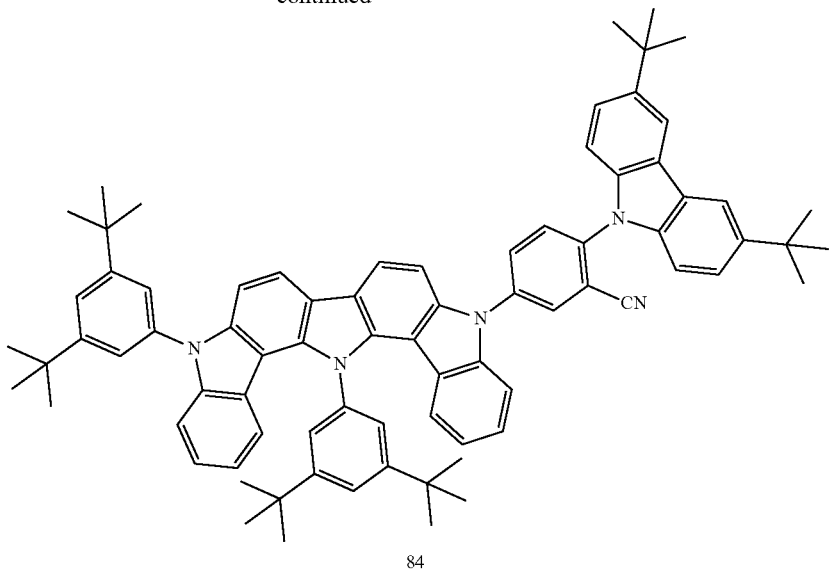

84

7 g (9.69 mmol) of 5,15-bis(3,5-di-tert-butylphenyl)-10,15-dihydro-5H-pyrrolo[3,2-c:4,5-c']dicarbazole, 5.35 g (11.63 mmol) of Intermediate 1, 1.863 g (19.39 mmol) of tert-sodium butoxide, 0.444 g (0.48 mmol) of Pd$_2$(dba)$_3$, and 0.392 g (1.94 mmol) of tri-tert-butyl phosphine were added to 50 mL of toluene, and the reaction mixture underwent a reaction at a temperature of 110° C. for 12 hours. Then, the reaction mixture was cooled to room temperature and precipitated by using methanol, and a solid compound was filtered. A product obtained therefrom was column-purified and vacuum-dried to obtain 3.73 g of (yield: 35%) of Compound 84.

MALDI-MS Calcd: 1099.65, Found: 1099.6.

Synthesis Example 3: Synthesis of Compound 80

(1) Synthesis of Intermediate I-4

After the reaction was completed, the reaction mixture was cooled to room temperature, and a solid precipitated by methanol was filtered and recovered. Then, a product was extracted therefrom by using CH$_2$Cl$_2$, dried by using MgSO$_4$, filtered by using a silica gel pad, concentrated, and recrystallized by using CH$_2$Cl$_2$:hexane to obtain Intermediate I-4 (yield: 64%).

(2) Synthesis of Compound 80

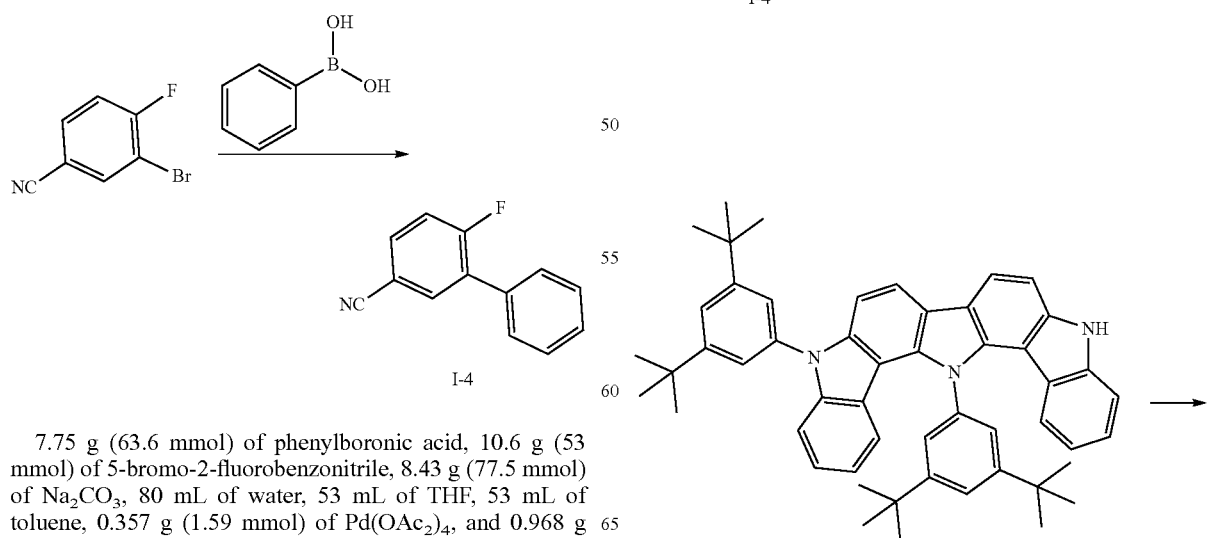

7.75 g (63.6 mmol) of phenylboronic acid, 10.6 g (53 mmol) of 5-bromo-2-fluorobenzonitrile, 8.43 g (77.5 mmol) of Na$_2$CO$_3$, 80 mL of water, 53 mL of THF, 53 mL of toluene, 0.357 g (1.59 mmol) of Pd(OAc$_2$)$_4$, and 0.968 g (3.18 mmol) of P(o-tolyl)$_3$ were added to the three-neck flask and refluxed in a nitrogen atmosphere for 2 hours.

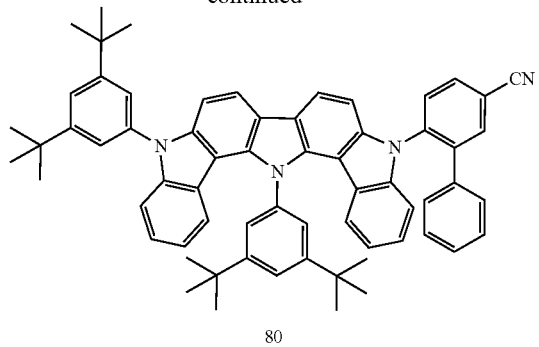

80

Compound 80 (yield: 77%) was synthesized in the same manner as in Synthesis of Compound 41 in Synthesis Example 1, except that 5,15-bis(3,5-di-tert-butylphenyl)-10,15-dihydro-5H-pyrrolo[3,2-c:4,5-c']dicarbazole was used instead of 15-phenyl-10,15-dihydro-5H-pyrrolo[3,2-c:4,5-c']dicarbazole, and Intermediate I-4 was used instead of 2-fluorobenzonitrile.

MALDI-MS Calcd: 898.5, Found: 899.5.

Synthesis Example 4: Synthesis of Compound 76

(1) Synthesis of Intermediate I-5

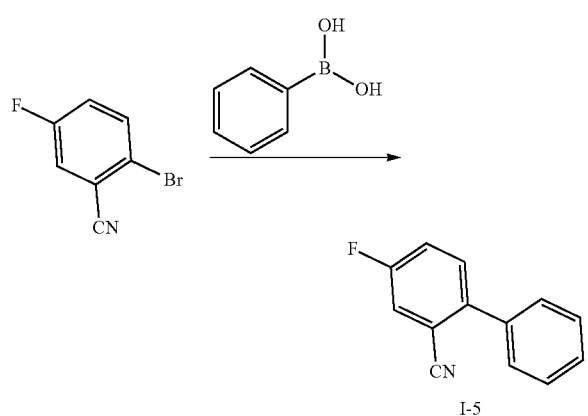

I-5

Intermediate I-5 (yield: 64%) was synthesized in the same manner as in Synthesis of Intermediate I-4, except that 2-bromo-5-fluorobenzonitrile was used instead of 5-bromo-2-fluorobenzonitrile.

(2) Synthesis of Compound 76

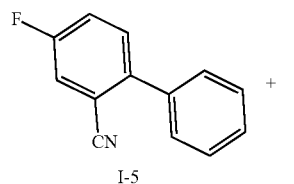

I-5

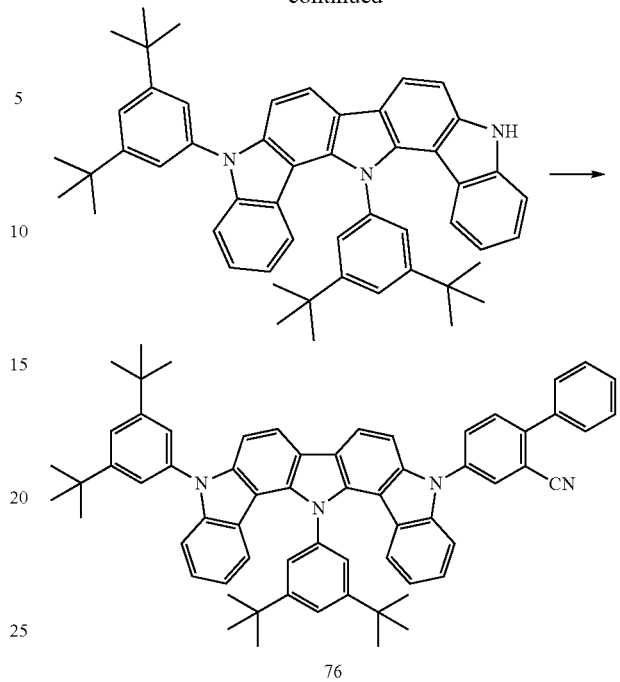

76

Compound 76 (yield: 72%) was synthesized in the same manner as in Synthesis of Compound 41 in Synthesis Example 1, except that 5,15-bis(3,5-di-tert-butylphenyl)-10,15-dihydro-5H-pyrrolo[3,2-c:4,5-c']dicarbazole was used instead of 15-phenyl-10,15-dihydro-5H-pyrrolo[3,2-c:4,5-c']dicarbazole, and Intermediate I-5 was used instead of 2-fluorobenzonitrile.

MALDI-MS Calcd: 898.5, Found: 899.5.

Synthesis Example 8: Synthesis of Compound 61

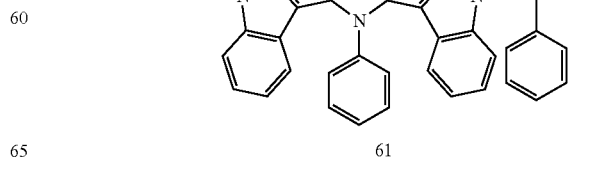

I-4

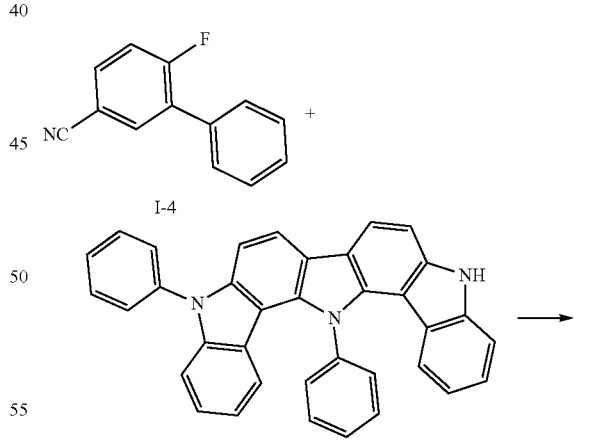

61

Compound 61 (41%) was synthesized in the same manner as in Synthesis of Compound 41 in Synthesis Example 1, except that 5,15-diphenyl-10,15-dihydro-5H-pyrrolo[3,2-c:4,5-c']dicarbazole was used instead of 15-phenyl-10,15-dihydro-5H-pyrrolo[3,2-c:4,5-c']dicarbazole, and Intermediate I-4 was used instead of 2-fluorobenzonitrile.

MALDI-MS Calcd: 674.25, Found: 675.2.

Evaluation Example 1: Evaluation on HOMO, LUMO, and Triplet ($T_1$) Energy Levels HOMO, LUMO, and T1 energy levels of Compounds 41, 61, 84, 80, and 76 and Compound A, B, C, D, E, and F were evaluated according to the methods shown in Table 1, and results thereof are shown in Table 3.

TABLE 2

| | |
|---|---|
| HOMO energy level evaluation method | A voltage-current (V-A) graph of each Compound was obtained by using a cyclic voltammetry (CV) (electrolyte: 0.1 molar (M) BU$_4$NClO$_4$/solvent: CH$_2$Cl$_2$/electrode: 3-electrode system (work electrode: GC, reference electrode: Ag/AgCl, auxiliary electrode: Pt)), and a HOMO energy level of each Compound was calculated from reduction onset of the graph. |
| LUMO energy level evaluation method | Each compound was diluted at a concentration of $1 \times 10^{-5}$M in CHCl$_3$, and an UV absorption spectrum thereof was measured at room temperature by using a Shimadzu UV-350 spectrometer, and a LUMO energy level thereof was calculated by using an optical band gap ($E_g$) from an edge of the absorption spectrum. |
| T1 energy level evaluation method | A mixture (each compound was dissolved in an amount of 1 milligram (mg) in 3 cubic centimeters (cc) of toluene) of toluene and each compound was loaded into a quartz cell, and then, the resultant quartz cell was loaded into liquid nitrogen (77 Kelvins, K) and a photoluminescence spectrum thereof was measured by using a device for measuring photoluminescence, and the obtained spectrum was compared with a photoluminescence spectrum measured at room temperature, and peaks observed only at low temperature were analyzed to calculate $T_1$ energy levels. |

TABLE 3

| Compound No. | HOMO (eV) (found) | LUMO (eV) (found) | T1 energy level (eV) |
|---|---|---|---|
| Compound 41 | −5.64 | −2.61 | 2.81 |
| Compound 61 | −5.55 | −2.57 | 2.81 |
| Compound 84 | −5.56 | −2.54 | 2.749 |
| Compound 80 | −5.36 | −2.358 | 2.812 |
| Compound 76 | −5.48 | −2.441 | 2.805 |
| Compound A | −5.14 | −1.80 | 2.91 |
| Compound B | −5.41 | −2.41 | 2.42 |
| Compound C | −5.14 | −2.34 | 2.42 |
| Compound D | −5.24 | −2.22 | 2.76 |
| Compound E | −5.14 | ND | 2.76 |
| Compound F | −5.16 | −2.11 | 2.81 |

TABLE 3-continued

| Compound No. | HOMO (eV) (found) | LUMO (eV) (found) | T1 energy level (eV) |
|---|---|---|---|

41

61

84

TABLE 3-continued
| Compound No. | HOMO (eV) (found) | LUMO (eV) (found) | T1 energy level (eV) |
|---|---|---|---|
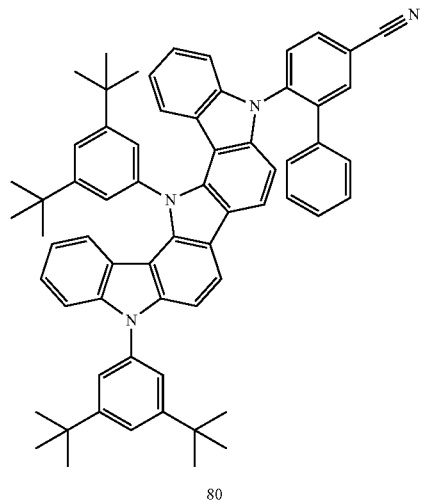 [SMILES: CC(C)(C)c1cc(-n2c3ccccc3c3c2ccc2c4ccc5c(c6ccccc6n5-c5ccc(C#N)cc5-c5ccccc5)c4n(-c4cc(C(C)(C)C)cc(C(C)(C)C)c4)c23)cc(C(C)(C)C)c1]
80
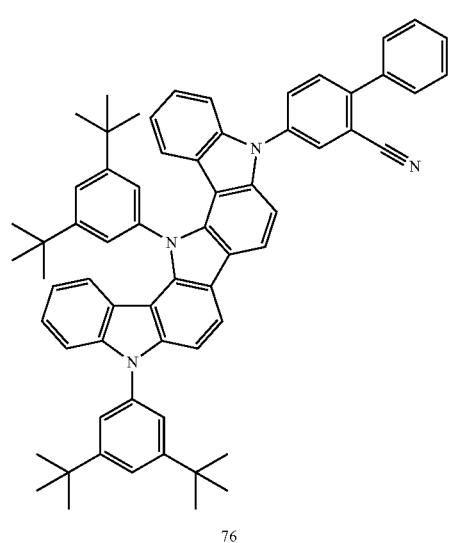 [SMILES: CC(C)(C)c1cc(-n2c3ccccc3c3c2ccc2c4ccc5c(c6ccccc6n5-c5ccc(-c6ccccc6)c(C#N)c5)c4n(-c4cc(C(C)(C)C)cc(C(C)(C)C)c4)c23)cc(C(C)(C)C)c1]
76
TABLE 3-continued
| Compound No. | HOMO (eV) (found) | LUMO (eV) (found) | T1 energy level (eV) |
|---|---|---|---|
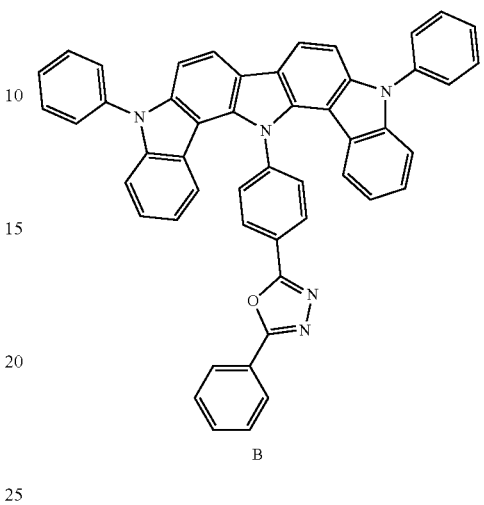
B
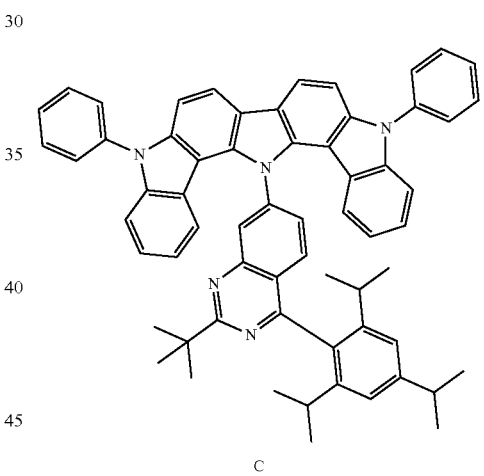
C
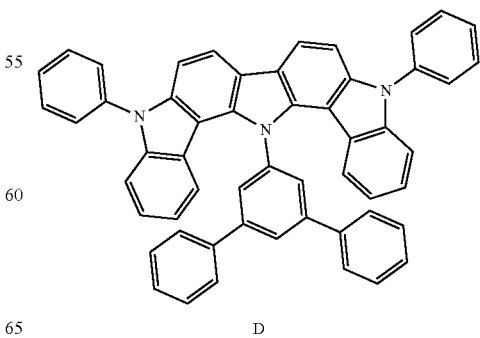
D
A

TABLE 3-continued

| Compound No. | HOMO (eV) (found) | LUMO (eV) (found) | T1 energy level (eV) |
|---|---|---|---|

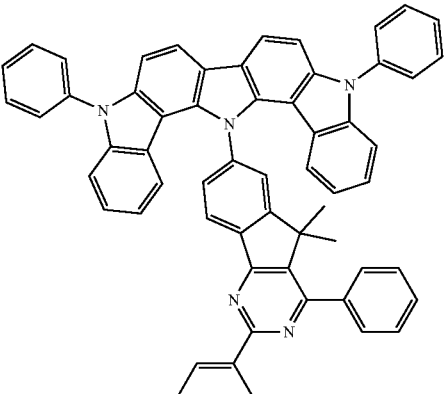

E

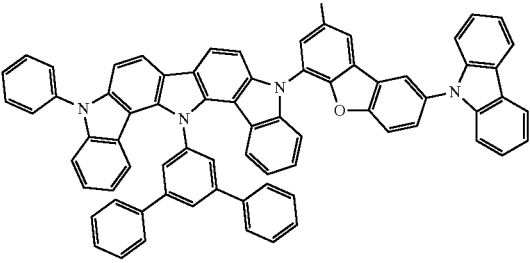

F

From Table 3, it is confirmed that the compounds above have electric characteristics that are suitable for use as a material for forming an organic light-emitting device.

Evaluation Example 2: Evaluation of Photoluminescence (PL) Quantum Yield, Emission Wavelength, and Delayed Fluorescence Characteristics Samples in which Compounds 1, 2, 3, A, B, C, D, E, and F were used as a dopant and H19 (host) and a dopant (15 weight %) were co-deposited in a quartz cell to a thickness of 100 Å was manufactured by using vacuum deposition. The samples were excited in a nitrogen atmosphere by excited light having a wavelength of 340 nm and PL quantum yields thereof were measured by using C9920-02 and PMA-11 manufactured by Hamamatsu photonics. Results thereof are shown in Table 4.

TABLE 4

| Dopant Compound | PL quantum yield (%) | Emission wavelength (nm) | Emission color | Presence or absence of delayed fluorescence |
|---|---|---|---|---|
| Compound 1 | 28 | 450 | Blue | ○ |
| Compound 2 | 48 | 455 | Blue | ○ |
| Compound 3 | 54 | 465 | Blue | ○ |
| Compound 4 | 66 | 458 | Blue | ○ |
| Compound 5 | 59 | 466 | Blue | ○ |

TABLE 4-continued

| Dopant Compound | PL quantum yield (%) | Emission wavelength (nm) | Emission color | Presence or absence of delayed fluorescence |
|---|---|---|---|---|
| Compound A | 3 | 380 | Violet | X |
| Compound B | 13 | 528 | Green | ○ |
| Compound C | 38 | 538 | Green | ○ |
| Compound D | 3 | 487 | Blue | ○ |
| Compound E | 53 | 500 | Green | ○ |
| Compound F | 30 | 438 | Blue | ○ |

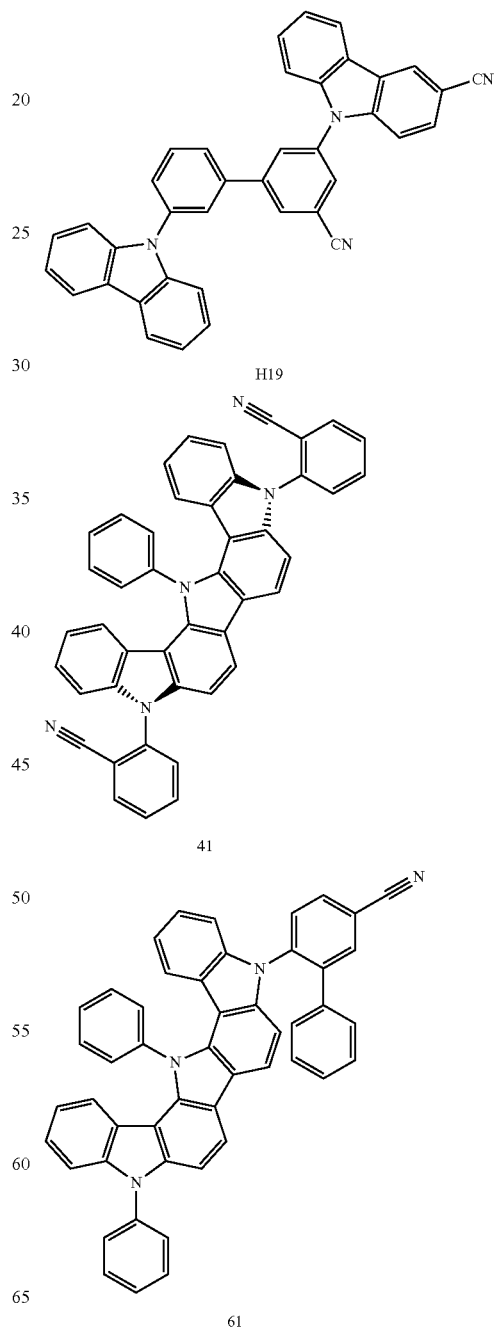

TABLE 4-continued
| Dopant Compound | PL quantum yield (%) | Emission wavelength (nm) | Emission color | Presence or absence of delayed fluorescence |
|---|---|---|---|---|
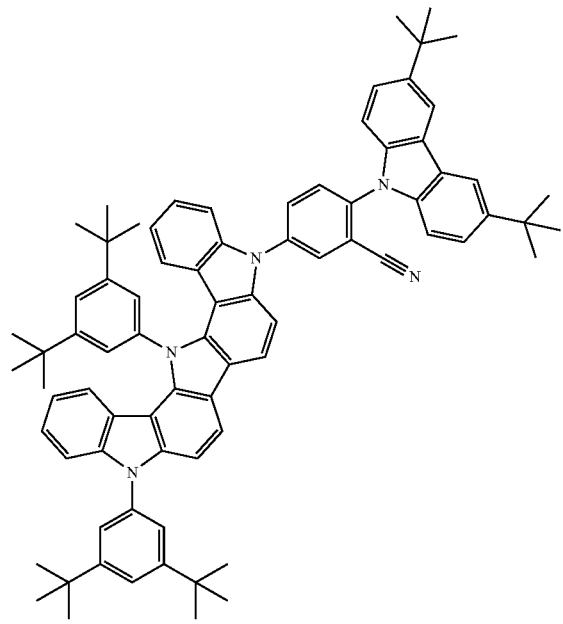
84
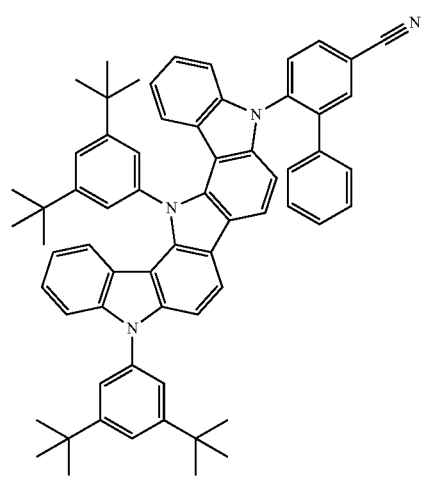
80
TABLE 4-continued
| Dopant Compound | PL quantum yield (%) | Emission wavelength (nm) | Emission color | Presence or absence of delayed fluorescence |
|---|---|---|---|---|
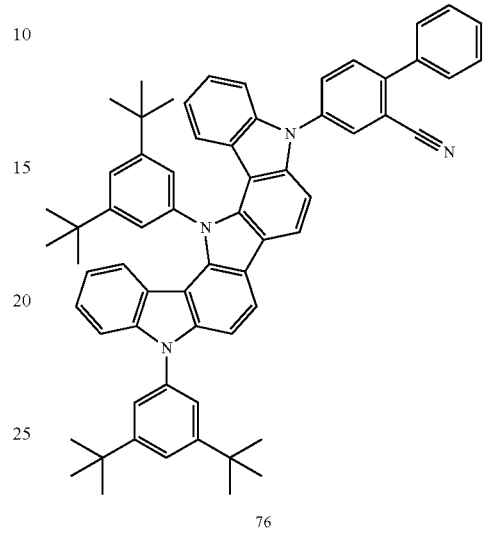
76
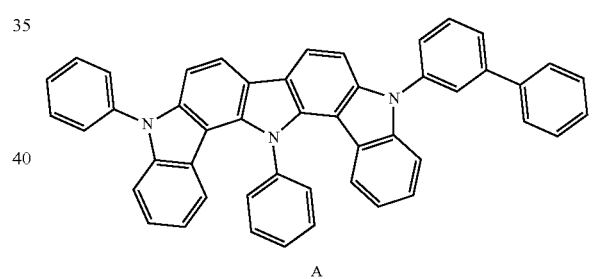
A
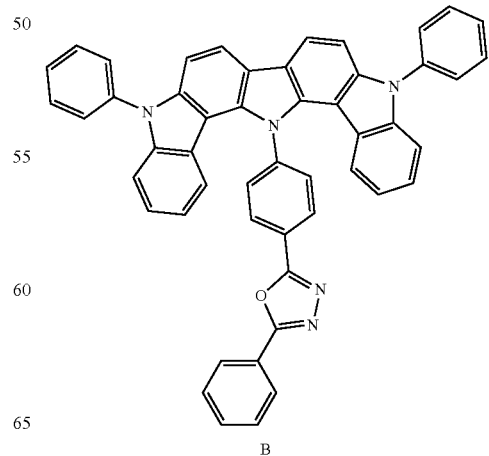
B TABLE 4-continued

| Dopant Compound | PL quantum yield (%) | Emission wavelength (nm) | Emission color | Presence or absence of delayed fluorescence |
|---|---|---|---|---|

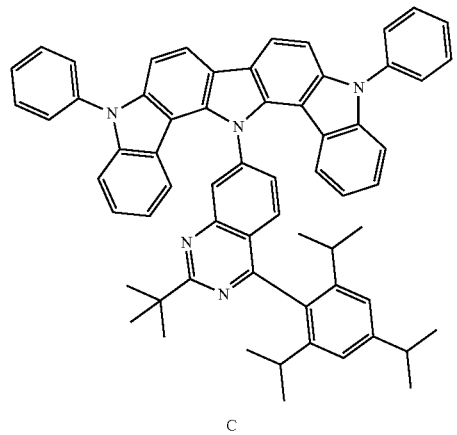

C

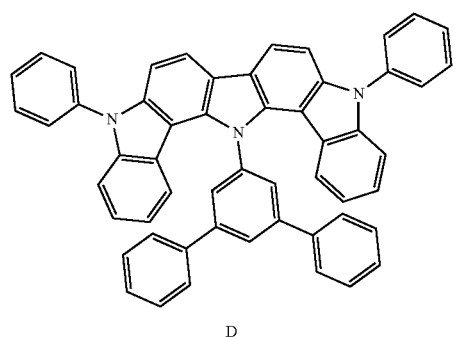

D

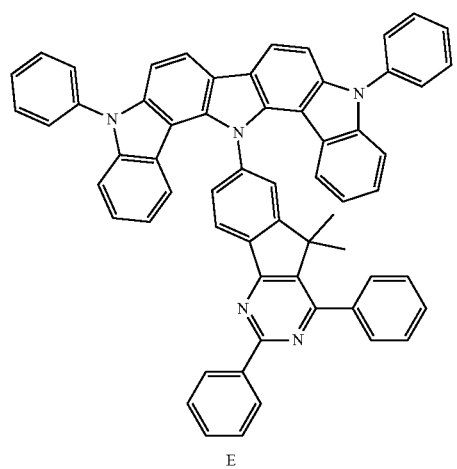

E

TABLE 4-continued

| Dopant Compound | PL quantum yield (%) | Emission wavelength (nm) | Emission color | Presence or absence of delayed fluorescence |
|---|---|---|---|---|

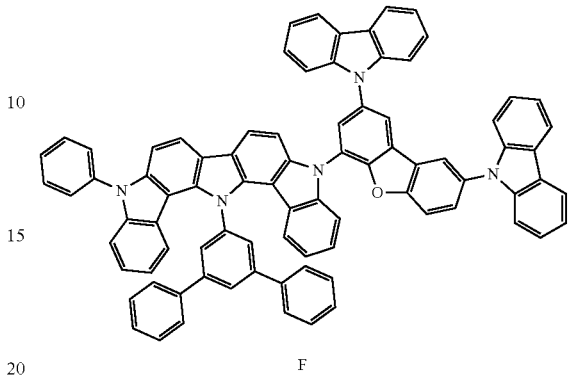

F

Referring to Table 4, it is confirmed that Compounds 1, 2, and 3 have higher PL quantum yields than those of Compounds A, B, and C. In addition, in the case of Compounds B, C, and E that emit blue light, the PL quantum yield was highly measured due to inherent characteristics of green light, but Compounds B, C, and E were shifted to a long wavelength and did not have characteristics suitable for a material of a blue organic light-emitting device. In addition, Compound A exhibited an emission wavelength of a violet-based short wavelength range. Since an energy difference between S1 and T1 regions is great, simple fluorescence instead of delayed fluorescence was exhibited, and thus, Compound A did not have characteristics suitable for use as a material for manufacturing a blue organic light-emitting device.

Example 1

A glass substrate with a 1,500 Å-thick Indium tin oxide (ITO) electrode (first electrode, anode) formed thereon was washed with distilled water and ultrasonic waves. When the washing with distilled water was completed, sonification washing was performed using a solvent, such as iso-propyl alcohol, acetone, or methanol. The result was dried and then transferred to a plasma washer, and the resultant substrate was washed with oxygen plasma for 5 minutes and then, transferred to a vacuum depositing device.

Compound HT3 was vacuum-deposited on the ITO electrode of the glass substrate to form a hole injection layer having a thickness of 100 Å, and Compound HT13 was deposited on the hole injection layer to form a hole transport layer having a thickness of 1,300 Å, thereby forming a hole transport region.

Compound H19 (host) and Compound 84 (dopant, 15 weight %) were deposited on the hole transport region to form an emission layer having a thickness of 300 Å.

ET3 and LiQ were vacuum-deposited on the emission layer to form an electron transport layer having a thickness of 250 Å, LiQ was deposited on the electron transport layer to form an electron injection layer having a thickness of 5 Å, and Al was deposited on the electron injection layer to form an Al second electrode (cathode) having a thickness of 1,000 Å, thereby completing the manufacture of an organic light-emitting device.

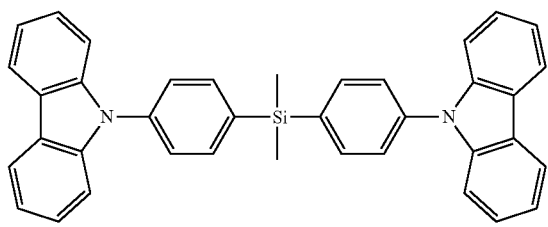

H3

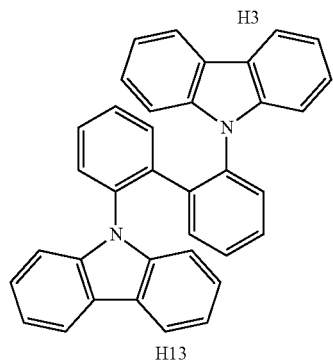

H13

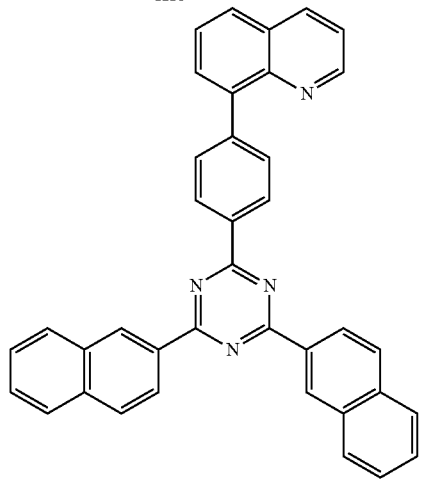

ET3

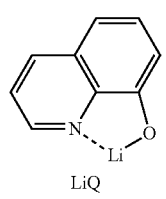

LiQ

Examples 2 and 3 and Comparative Examples 1 and 2

Organic light-emitting devices were manufactured in the same manner as in Example 1, except that Compounds shown in Table 5 were each used instead of Compound 84 as a dopant in forming an emission layer.

Evaluation Example 3: Evaluation of Characteristics of Organic Light-Emitting Devices The driving voltage, current efficiency, PL quantum yield, and EL spectrum of the organic light-emitting devices manufactured according to Examples 1 to 3 and Comparative Examples 1 and 2 were measured by using a current-voltage meter (Keithley 2400) and a luminance meter (Minolta Cs-1000A), and results are shown in Table 5.

TABLE 5

| | Dopant | Driving voltage (V) | Current efficiency (cd/A) | Quantum efficiency (%) | Emission wavelength (nm) |
|---|---|---|---|---|---|
| Example 1 | Compound 84 | 9.1 | 35.6 | 18.9 | 461 |
| Example 2 | Compound 80 | 7.8 | 25.4 | 14.9 | 460 |
| Example 3 | Compound 76 | 9.7 | 29.4 | 14.7 | 466 |
| Comparative Example 1 | Compound A | 9.8 | 9.2 | 5.1 | 440 |
| Comparative Example 2 | Compound B | 11.2 | 23.1 | 12.2 | 550 |

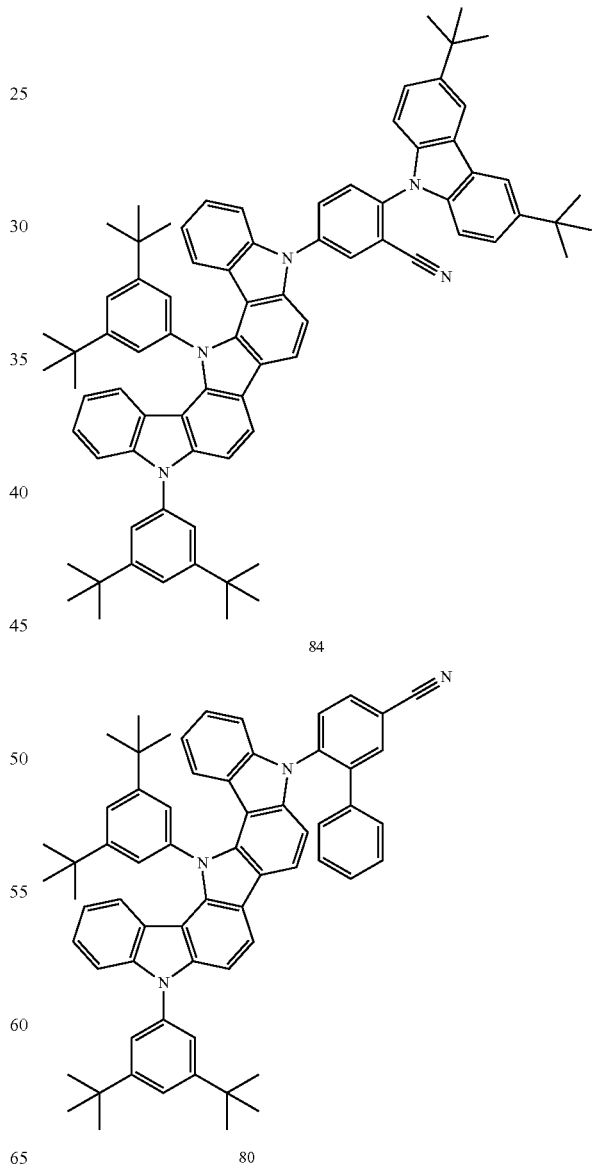

84

80

TABLE 5-continued

| Dopant | Driving voltage (V) | Current efficiency (cd/A) | Quantum efficiency (%) | Emission wavelength (nm) |
|---|---|---|---|---|

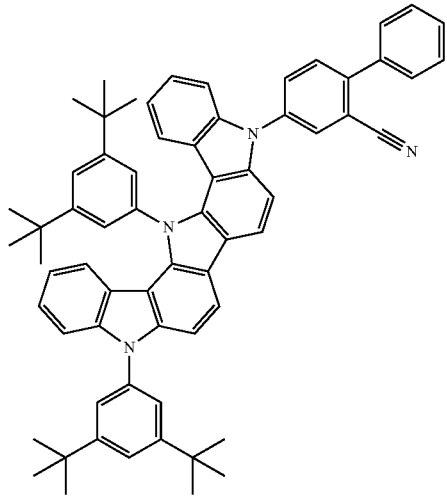

76

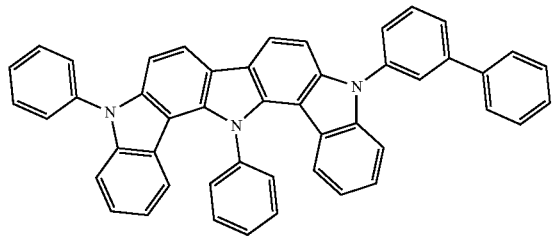

A

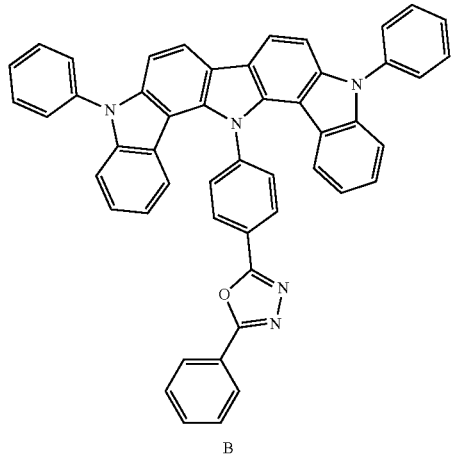

B

Referring to Table 5, it is confirmed that the organic light-emitting devices of Examples 1 to 3 using Compounds of the embodiments as a dopant have a low driving voltage, high current efficiency, and high PL quantum yield, as compared with those of the organic light-emitting devices of Comparative Examples 1 and 2. In addition, it is confirmed that the organic light-emitting devices of Examples 1 to 3 exhibit a blue light emission wavelength.

The condensed cyclic compounds according to embodiments have excellent electric characteristics and thermal stability. Accordingly, organic light-emitting devices including the condensed cyclic compounds may have a low driving voltage, high efficiency, high brightness, a long lifespan, and high color purity.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope as defined by the following claims.

What is claimed is:

1. A condensed cyclic compound represented by Formula 1:

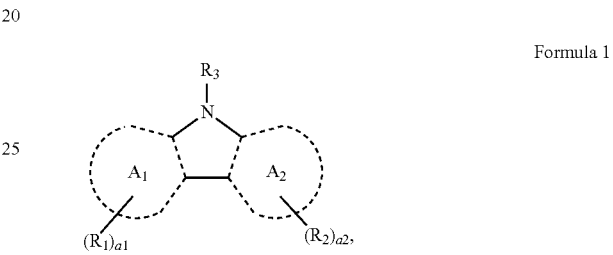

Formula 1 wherein, in Formula 1, $A_1$ and $A_2$ are each a carbazole group, $R_1$ to $R_3$ are each independently selected from hydrogen, deuterium, —F, —Cl, —Br, —I, a hydroxyl group, a cyano group, a cyano group-containing group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), wherein at least one of $R_1$ to $R_3$ is a cyano group or a cyano group-containing group, when at least two of $R_1$ to $R_3$ is a cyano group-containing group, $R_1$ to $R_3$ are identical to or different from each other, a1 and a2 are each independently an integer of 1 to 7, when a1 is two or more, two or more groups $R_1$ are identical to or different from each other, when a2 is two or more, two or more groups $R_2$ are identical to or different from each other, the number of cyano groups included in the condensed cyclic compound represented by Formula 1 is 1 to 10, at least one substituent of the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si$(Q_{11})(Q_{12})(Q_{13})$, —N$(Q_{14})(Q_{15})$, and —B$(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si$(Q_{21})(Q_{22})(Q_{23})$, —N$(Q_{24})(Q_{25})$, and —B$(Q_{26})(Q_{27})$; and —Si$(Q_{31})(Q_{32})(Q_{33})$, —N$(Q_{34})(Q_{35})$, and —B$(Q_{36})(Q_{37})$, and $Q_1$ to $Q_7$, $Q_{11}$ to $Q_{17}$, $Q_{21}$ to $Q_{27}$, and $Q_{31}$ to $Q_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group; and wherein the condensed cyclic compound represented by Formula 1 satisfies Equations 1 and 2:

$$2.5 \text{ eV} < E_{S1(TD)} < 3 \text{ eV} \qquad \text{Equation 1}$$

$$\Delta E_{ST} < 0.3 \text{ eV}, \qquad \text{Equation 2}$$

wherein $E_{S1(TD)}$ in Equation 1 is singlet energy expressed in electron volts (eV) of the condensed cyclic compound, and wherein $\Delta E_{ST}$ in Equation 2 is a difference between the singlet energy (eV) and triplet energy (eV) of the condensed cyclic compound.

2. The condensed cyclic compound of claim 1, wherein the cyano group-containing group is a group represented by Formula 2:

Formula 2 wherein $L_1$ is a $C_5$-$C_{30}$ carbocyclic group or a $C_1$-$C_{30}$ heterocyclic group, m1 is an integer of 1 to 5, when m1 is two or more, two or more groups $L_1$ are identical to or different from each other, $Ar_1$ is selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si$(Q_1)(Q_2)(Q_3)$, —N$(Q_4)(Q_5)$, and —B$(Q_6)(Q_7)$, n1 is an integer of 1 to 4, when n1 is two or more, two or more groups $Ar_1$ are identical to or different from each other, and

* indicates a binding site to a neighboring atom.

3. The condensed cyclic compound of claim 2, wherein $L_1$ is selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

4. The condensed cyclic compound of claim 2, wherein the group represented by Formula 2 is selected from Formulae 3-1 to 3-9:

3-1
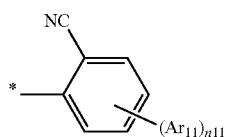

3-2
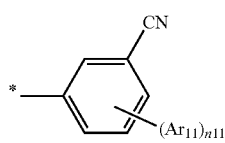

3-3
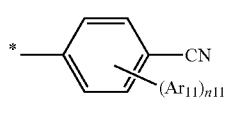

3-4
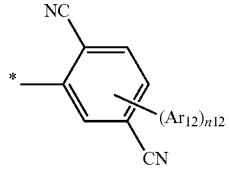

3-5
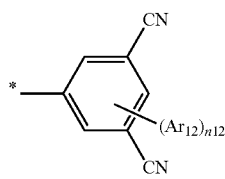

3-6
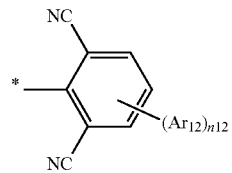

3-7
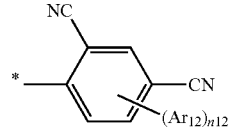

3-8
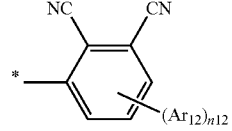

3-9
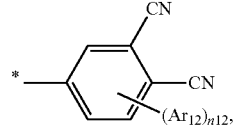

wherein, in Formulae 3-1 to 3-9, $Ar_{11}$ and $Ar_{12}$ are respectively the same as $Ar_1$ in claim 2, n11 is an integer of 1 to 4, n12 is an integer of 1 to 3, and

* indicates a binding site to a neighboring atom.

5. The condensed cyclic compound of claim 2, wherein $Ar_1$ is selected from:

hydrogen, deuterium, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, a cyano group, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group; and a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group, each substituted with at least one selected from deuterium, a $C_1$-$C_{20}$ alkyl group, a $C_1$-$C_{20}$ alkoxy group, a phenyl group, a biphenyl group, a terphenyl group, and a naphthyl group.

6. The condensed cyclic compound of claim 1, wherein $R_1$ to $R_3$ are each independently selected from:

a cyano group-containing group, hydrogen, deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, a pyrimidinyl group, a pyrazinyl group, a pyridazinyl group, and a triazinyl group;

a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyridimidinyl group, and an imidazopyridinyl group; and a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyridimidinyl group, and an imidazopyridinyl group, each substituted with at least one selected from deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

7. The condensed cyclic compound of claim 1, wherein the number of cyano groups included in the condensed cyclic compound represented by Formula 1 is 1 or 2.

8. The condensed cyclic compound of claim 1, wherein the condensed cyclic compound represented by Formula 1 is a compound represented by one selected from Formulae 1-1 to 1-21:

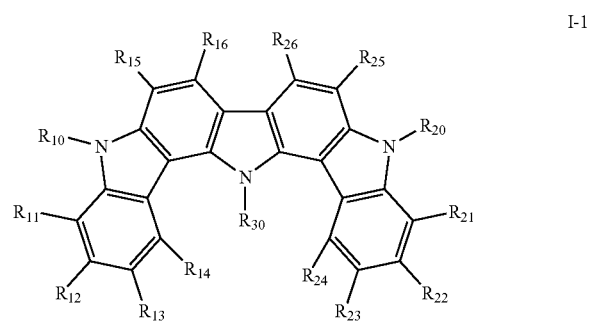

I-1

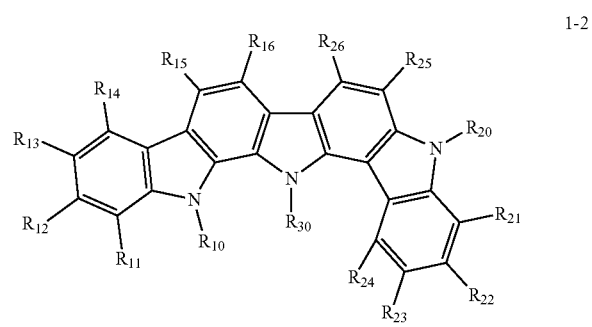

I-2

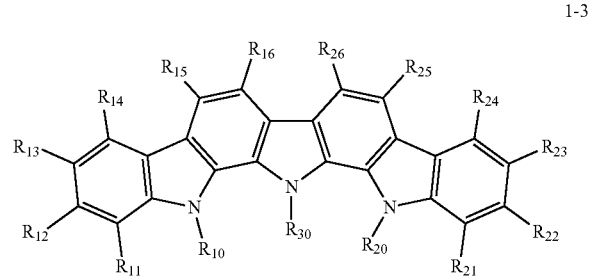

I-3

-continued
1-4
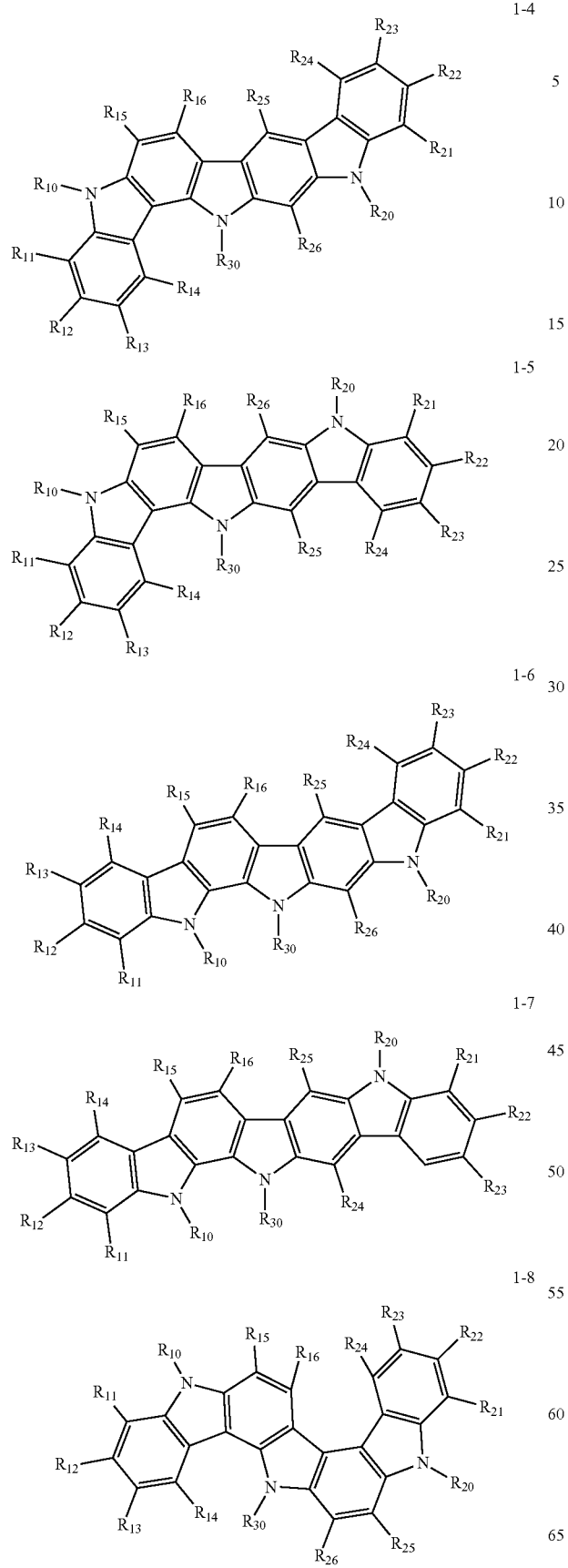
1-5
1-6
1-7
1-8
-continued
1-9
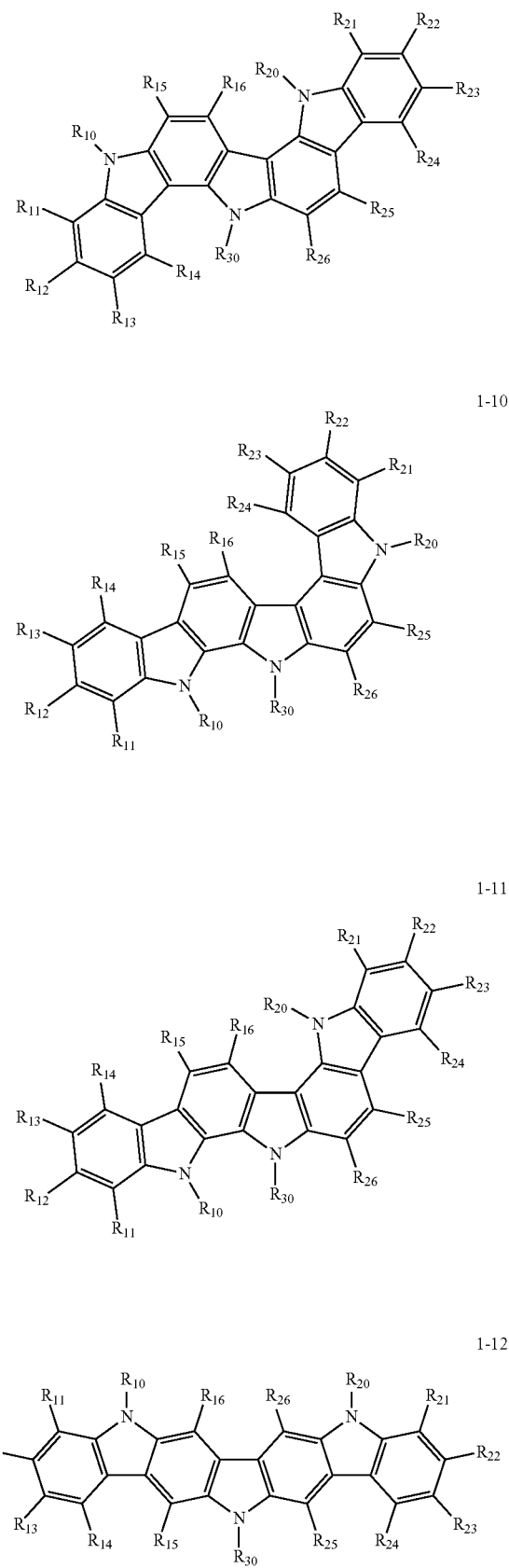
1-10
1-11
1-12

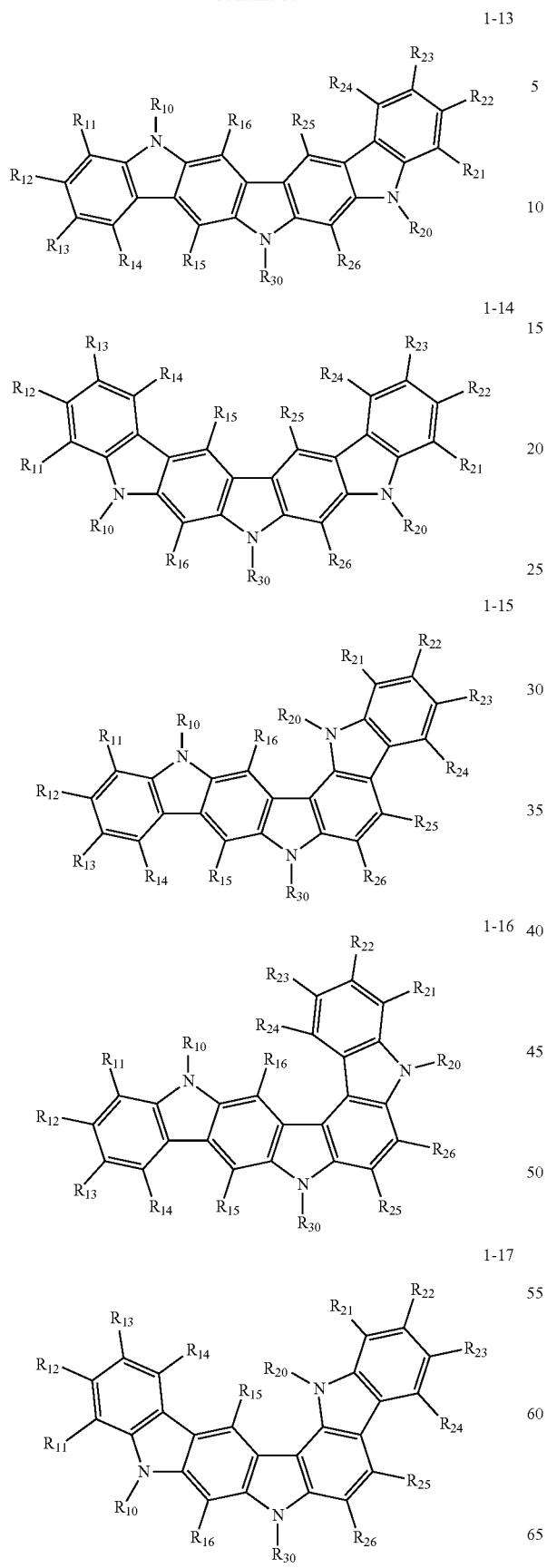
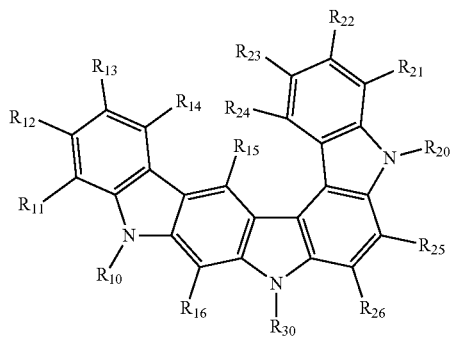
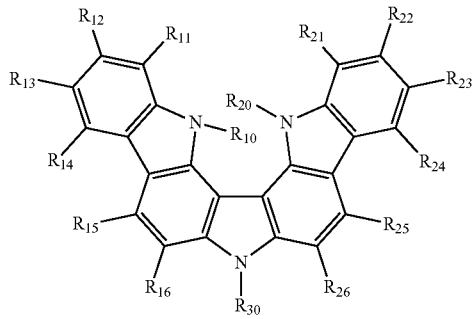
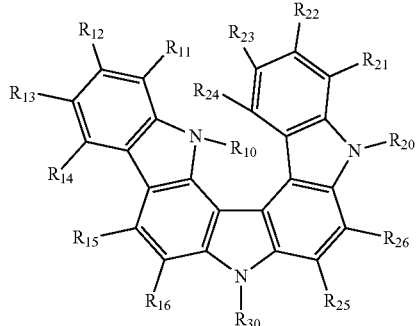
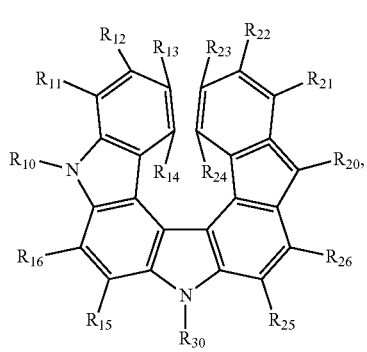

wherein, in Formulae 1-1 to 1-21, $R_{10}$ to $R_{16}$ are respectively the same as $R_1$ in claim 1, $R_{20}$ to $R_{26}$ are respectively the same as $R_2$ in claim 1, $R_{30}$ is the same as $R_3$ in claim 1, and at least one of $R_{10}$ to $R_{16}$, $R_{20}$ to $R_{26}$, and $R_{30}$ is a cyano group or a cyano group-containing group.

9. The condensed cyclic compound of claim 8, wherein at least one of $R_{10}$, $R_{20}$, and $R_{30}$ is a cyano group-containing group, or at least one of $R_{11}$ to $R_{16}$ and $R_{21}$ to $R_{26}$ is a cyano group.

10. The condensed cyclic compound of claim 8, wherein one of $R_{10}$, $R_{20}$, and $R_{30}$ is a cyano group-containing group.

11. A condensed cyclic compound represented by Formula 1:

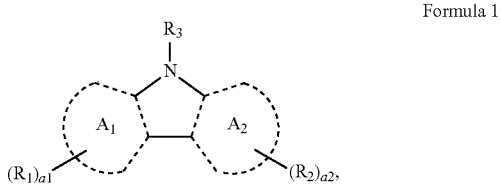

Formula 1 wherein, in Formula 1, $A_1$ and $A_2$ are each a carbazole group, $R_1$ to $R_3$ are each independently selected from hydrogen, deuterium, —F, —Cl, —Br, —I, a hydroxyl group, a cyano group, a cyano group-containing group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), wherein at least one of $R_1$ to $R_3$ is a cyano group or a cyano group-containing group, when at least two of $R_1$ to $R_3$ is a cyano group-containing group, $R_1$ to $R_3$ are identical to or different from each other, a1 and a2 are each independently an integer of 1 to 7, when a1 is two or more, two or more groups $R_1$ are identical to or different from each other, when a2 is two or more, two or more groups $R_2$ are identical to or different from each other, the number of cyano groups included in the condensed cyclic compound represented by Formula 1 is 1 to 10, at least one substituent of the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group:

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), and —B($Q_{26}$)($Q_{27}$); and —Si($Q_{31}$)($Q_{32}$)($Q_{33}$), —N($Q_{34}$)($Q_{35}$), and —B($Q_{36}$)($Q_{37}$), and $Q_1$ to $Q_7$, $Q_{11}$ to $Q_{17}$, $Q_{21}$ to $Q_{27}$ and $Q_{31}$ to $Q_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group; and wherein the condensed cyclic compound represented by Formula 1 satisfies Equations 1 and 2:

$$2.5 \text{ eV} < E_{S1(TD)} < 3 \text{ eV} \quad \text{Equation 1}$$

$$\Delta E_{ST} < 0.3 \text{ eV}, \quad \text{Equation 2}$$

wherein $E_{S1(TD)}$ in Equation 1 is singlet energy expressed in electron volts (eV) of the condensed cyclic compound, and wherein $\Delta E_{ST}$ in Equation 2 is a difference between the singlet energy (eV) and triplet energy (eV) of the condensed cyclic compound, wherein the condensed cyclic compound represented by Formula 1 is a compound represented by one selected from Formulae 1-1 to 1-21:

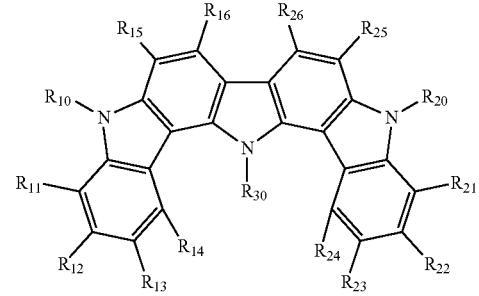
1-1

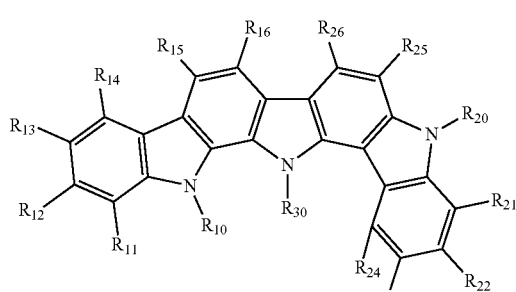
1-2

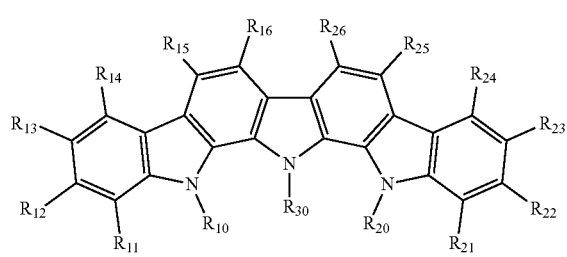
1-3

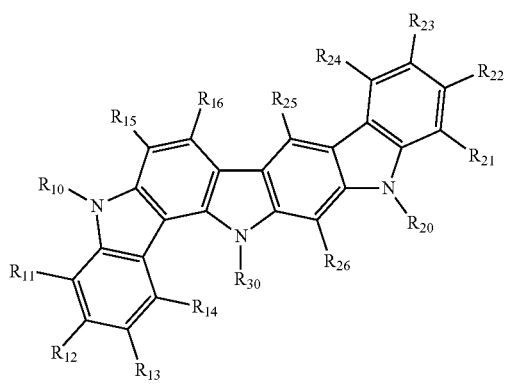
1-4

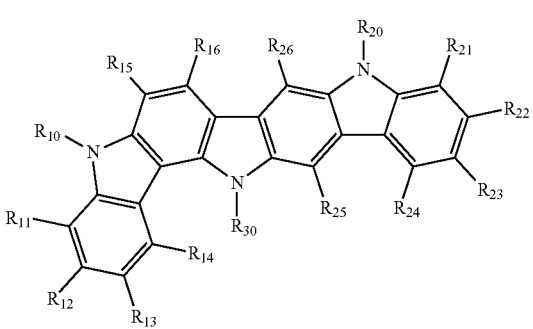
1-5

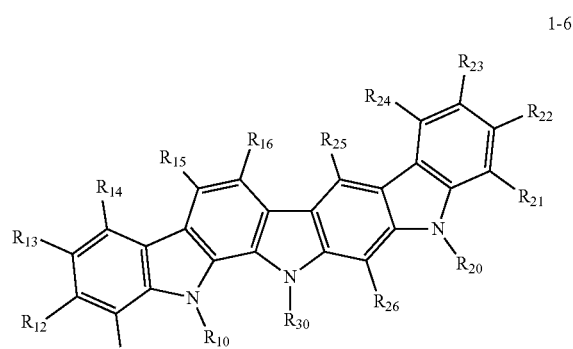
1-6

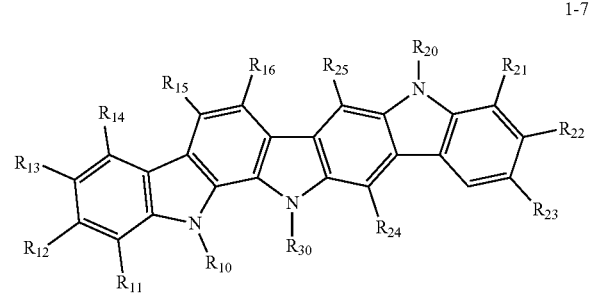
1-7

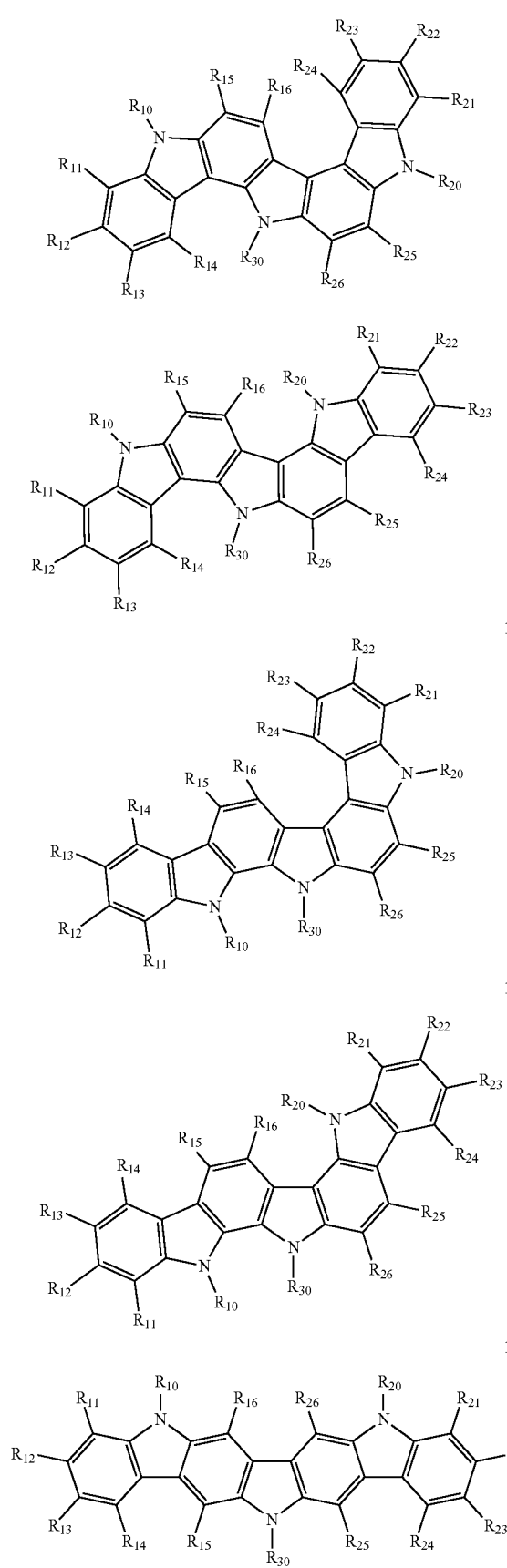
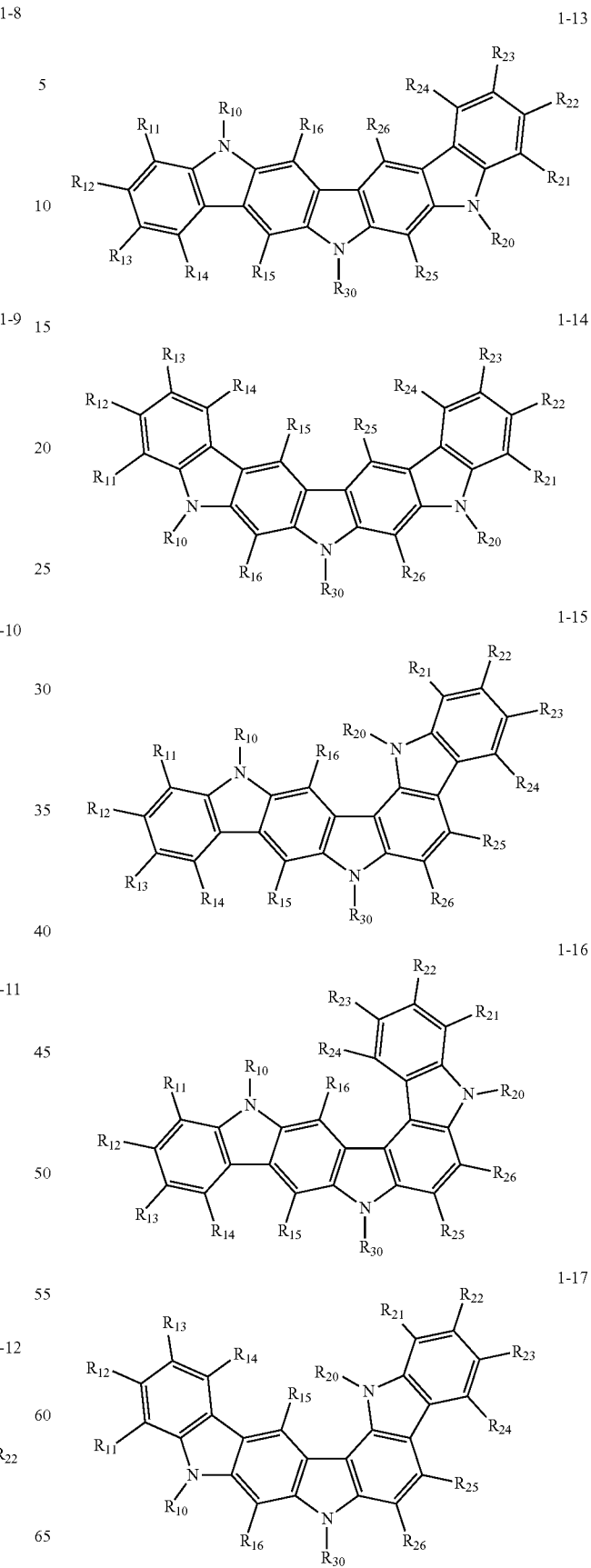

-continued 1-18
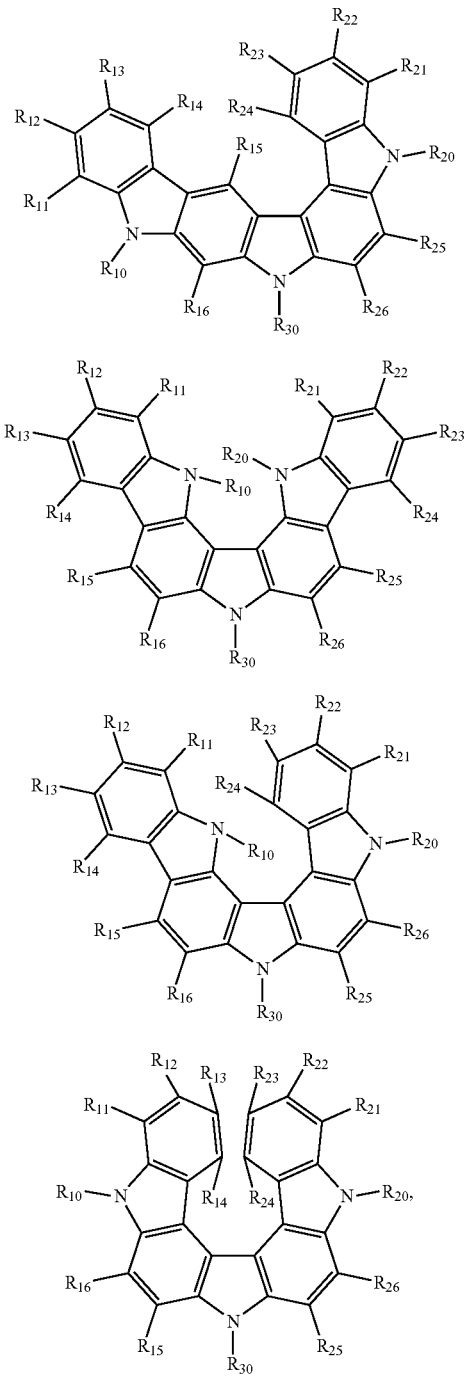

1-19

1-20

1-21 wherein, in Formulae 1-1 to 1-21,
$R_{10}$ to $R_{16}$ are respectively the same as $R_1$ in claim 1,
$R_{20}$ to $R_{26}$ are respectively the same as $R_2$ in claim 1,
$R_{30}$ is the same as $R_3$ in claim 1, and
at least one of $R_{10}$ to $R_{16}$, $R_{20}$ to $R_{26}$, and $R_{30}$ is a cyano group or a cyano group-containing group, and provided that, in the condensed cyclic compound represented by one selected from Formulae 1-1 to 1-21:

(i) $R_{10}$ and $R_{20}$ are each independently a cyano group-containing group, (ii) $R_{10}$ and $R_{30}$ are each independently a cyano group-containing group, (iii) one of $R_{11}$ to $R_{14}$ and $R_{21}$ to $R_{24}$ is a cyano group, and one of $R_{10}$ to $R_{30}$ is a cyano group-containing group, or (iv) one of $R_{15}$, $R_{16}$, $R_{25}$, and $R_{26}$ is a cyano group, and one of $R_{10}$ to $R_{30}$ is a cyano group-containing group.

12. A condensed cyclic compound represented by one of Compounds 1 to 112:

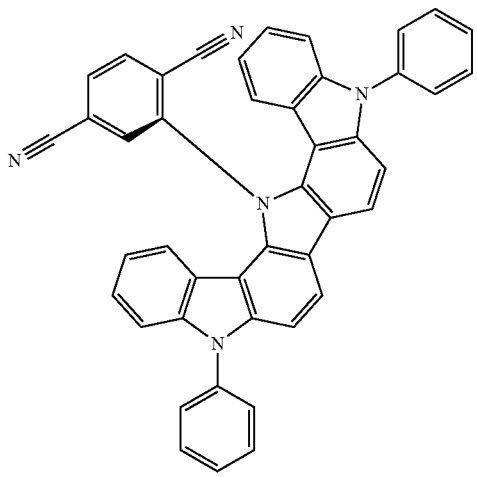

1

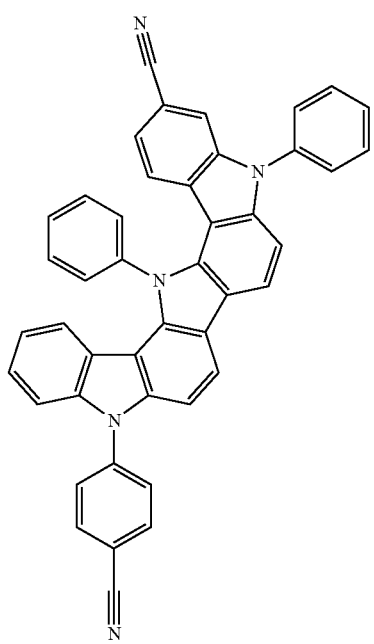

2

3
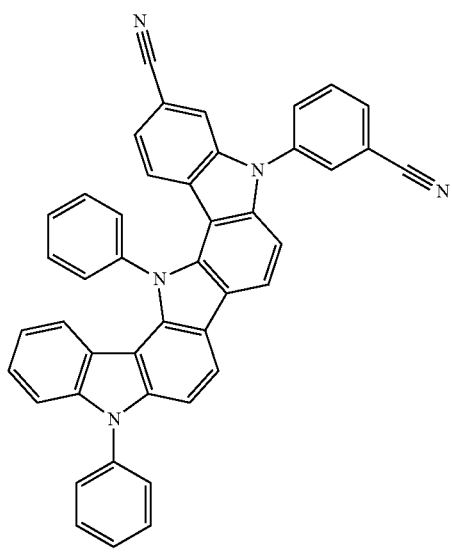
4
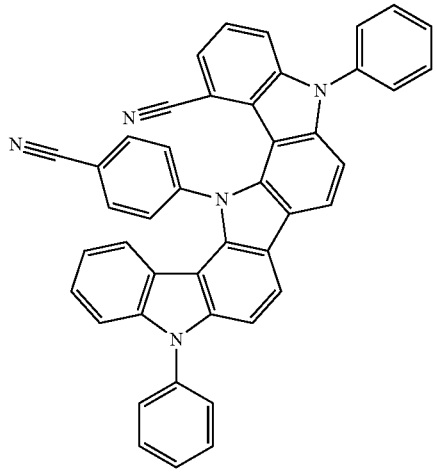
5
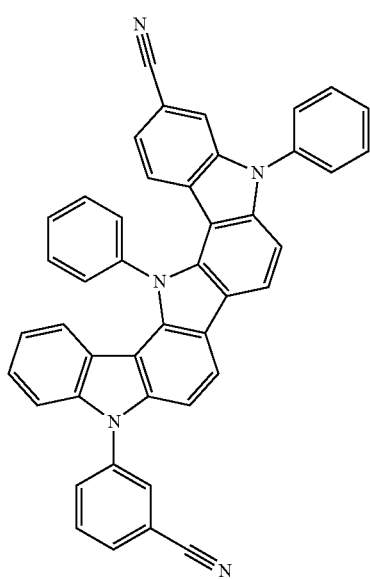
6
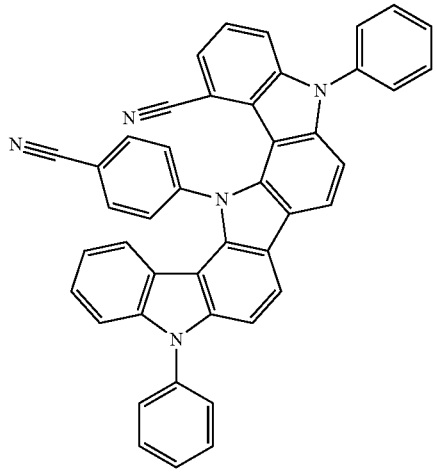
7
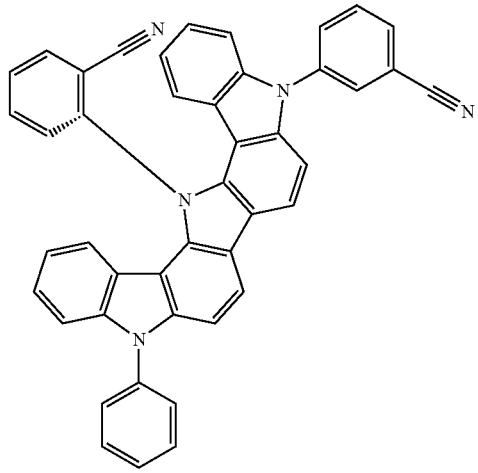
8
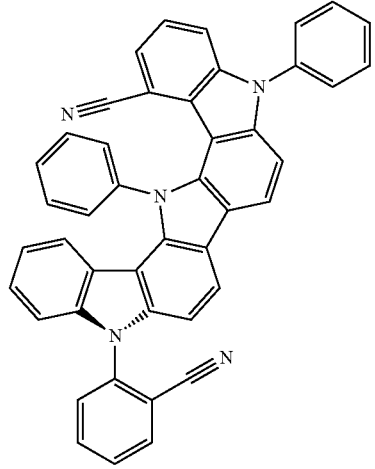

163
-continued
9
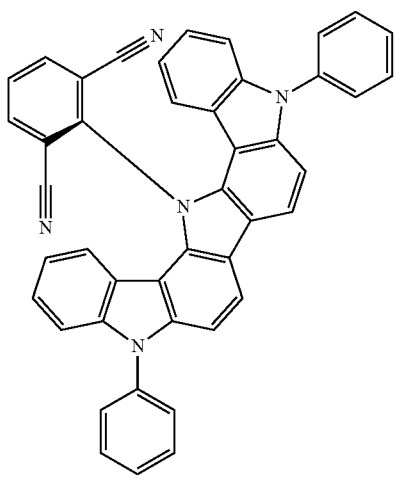
10
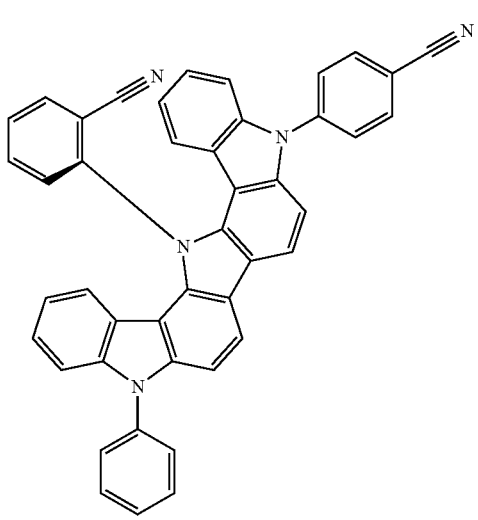
11
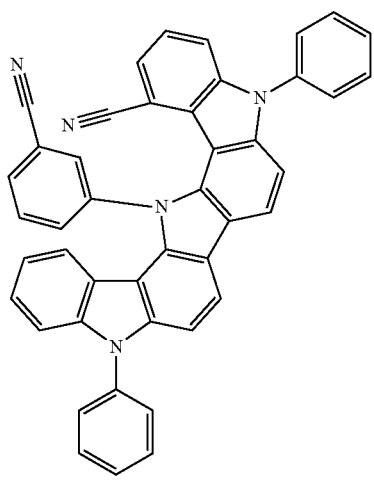
164
-continued
12
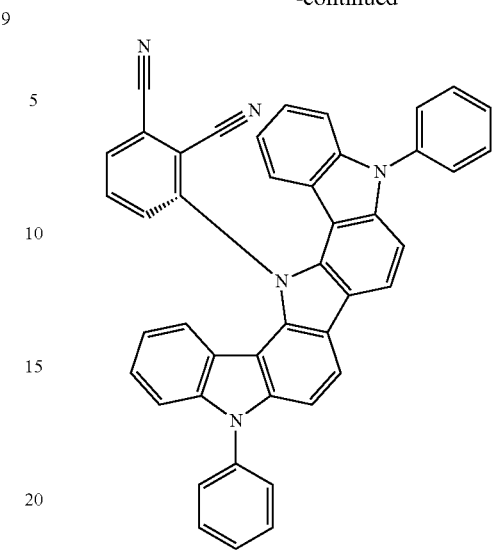
13
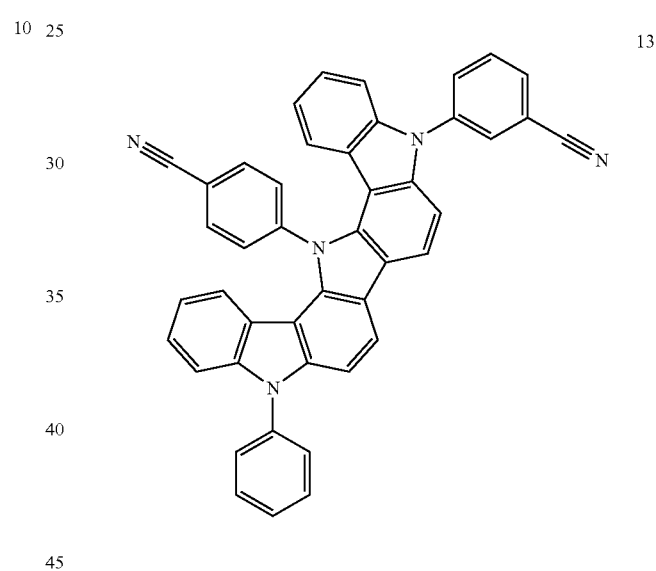
14
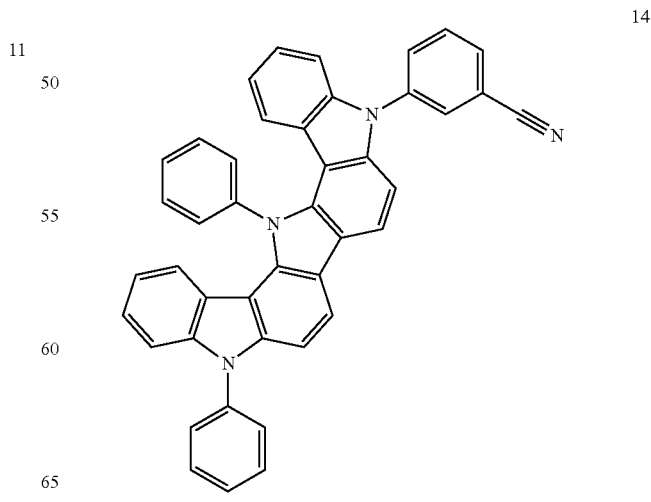

| 15 | 18 |
|---|---|
| 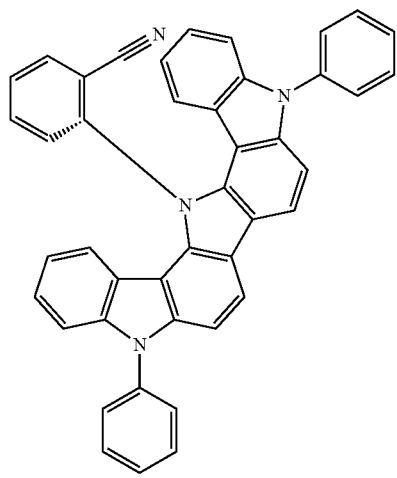 | 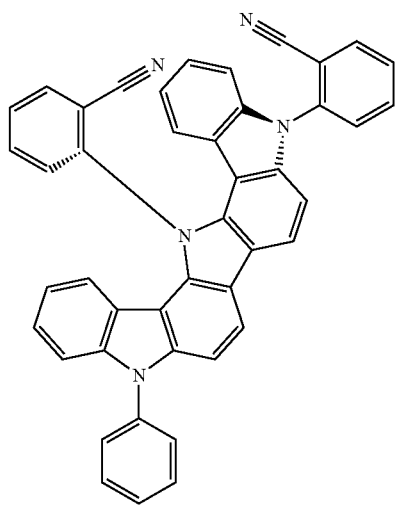 |
| 16 | 19 |
| 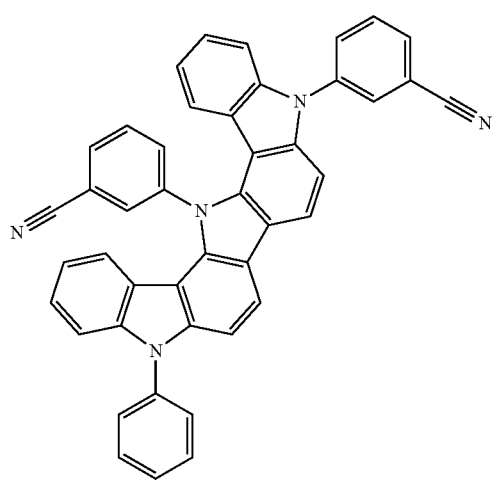 | 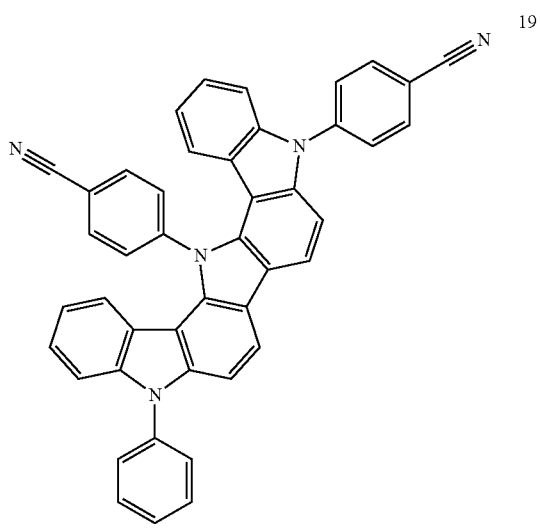 |
| 17 | 20 |
| 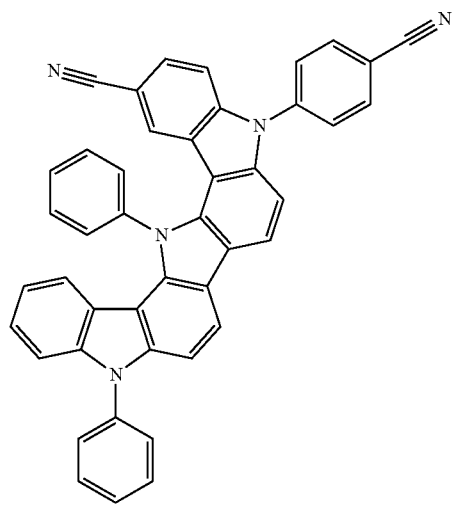 | 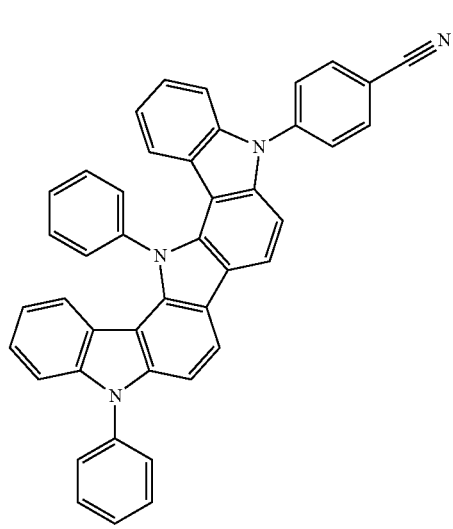 |

167 -continued
21
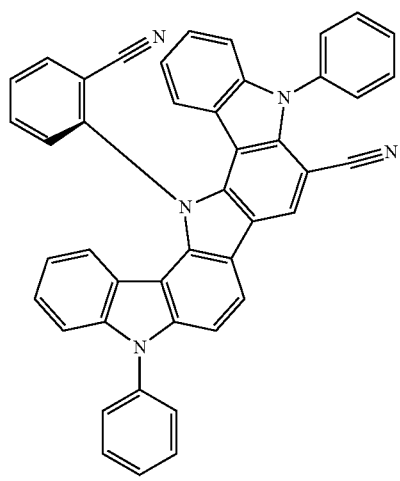
22
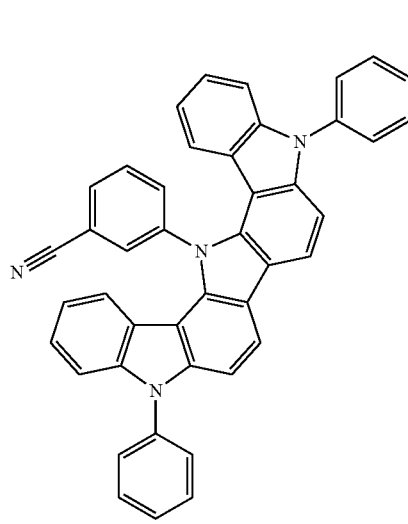
23
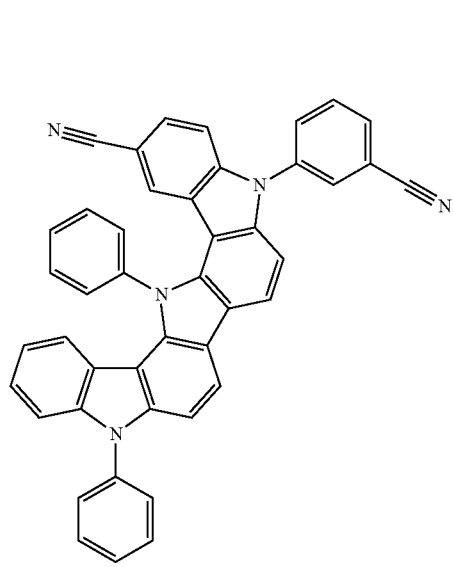
168 -continued
24
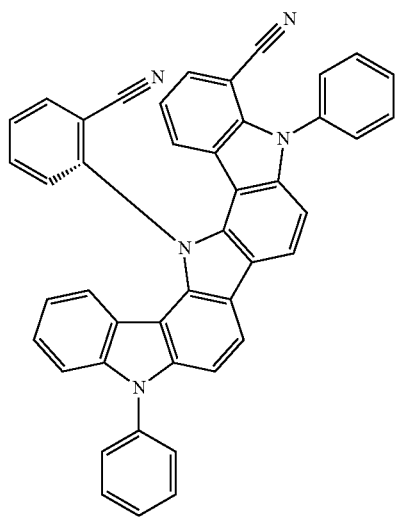
25
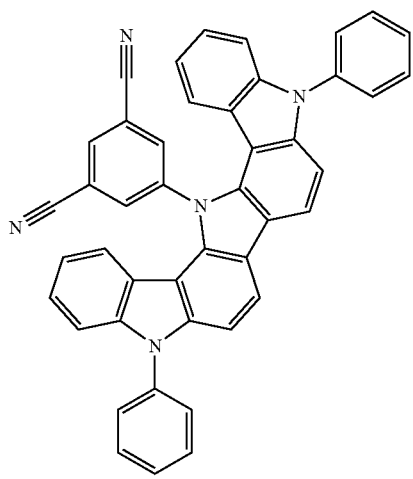
26
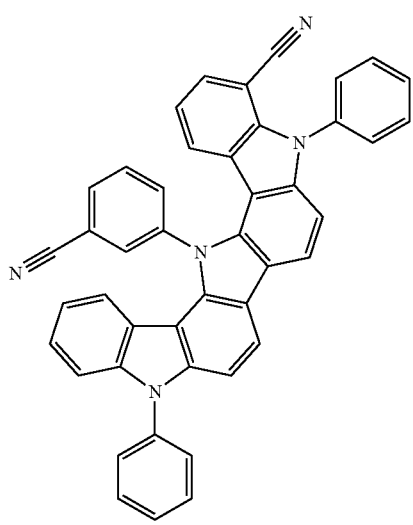

27
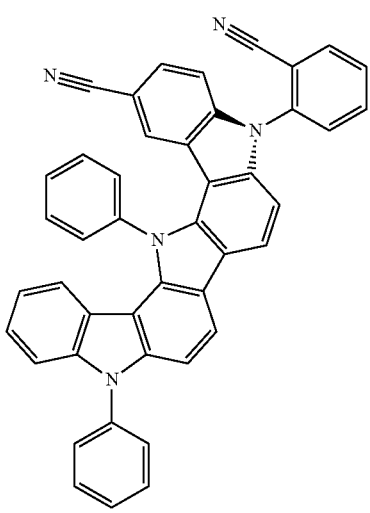
28
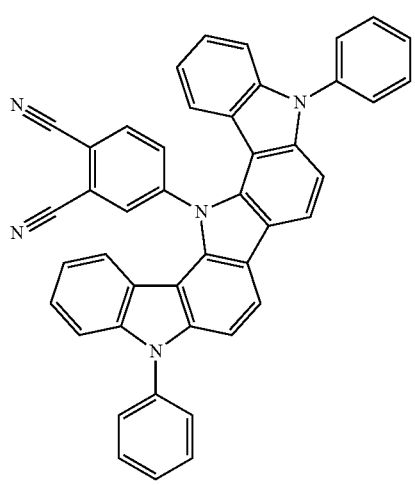
29
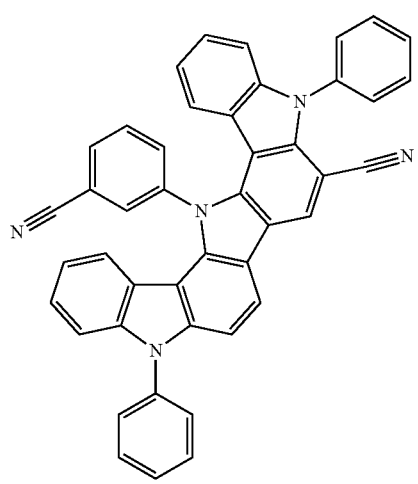
30
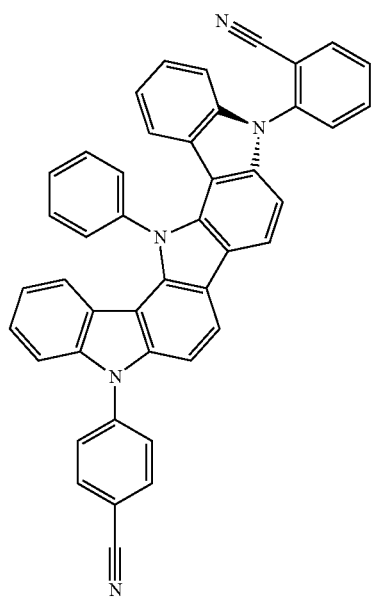
31
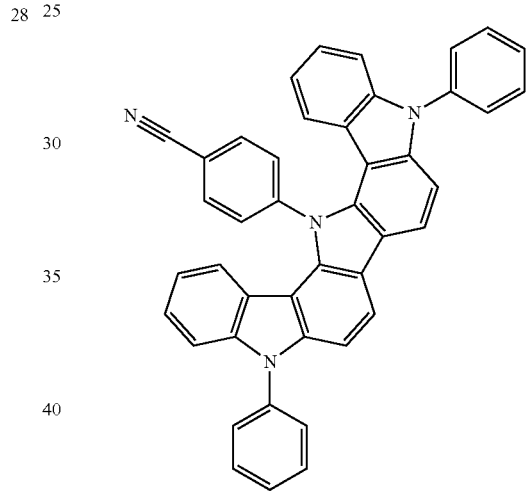
32
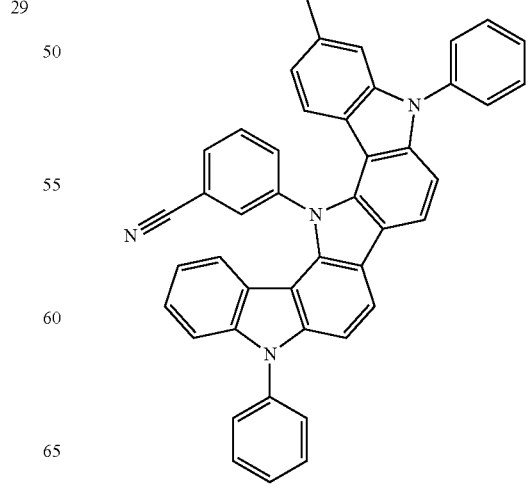

33
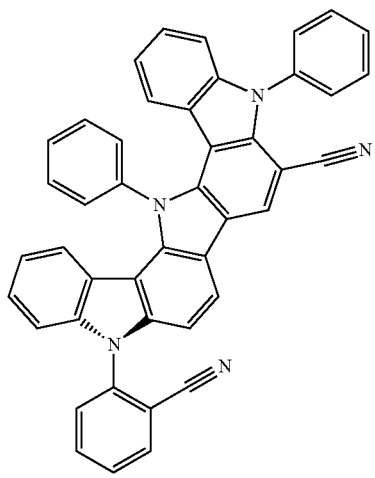
34
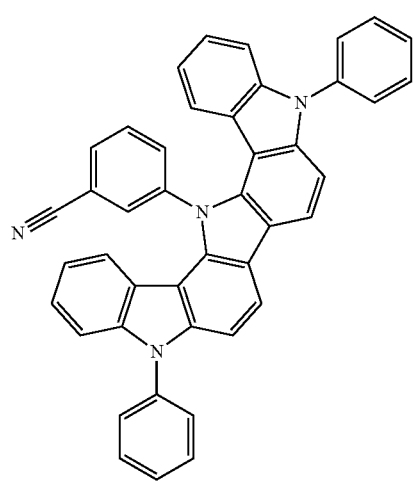
35
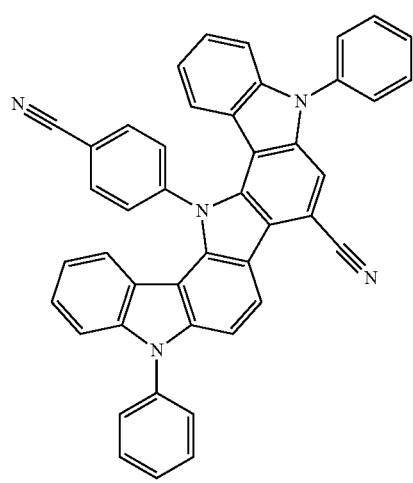
36
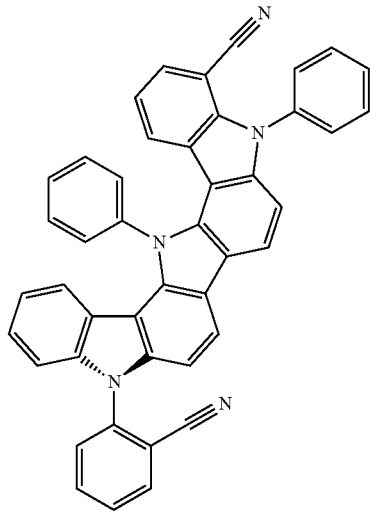
37
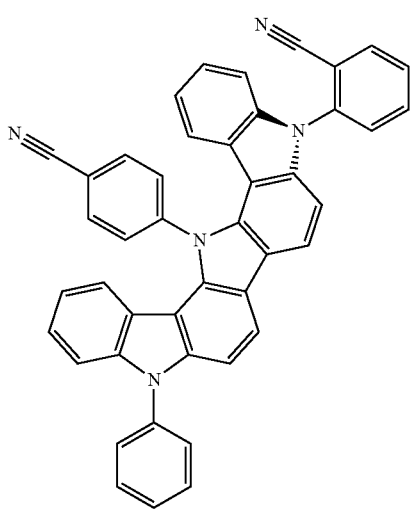
38
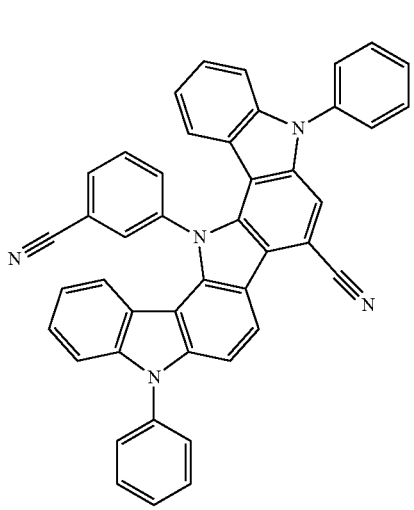

39
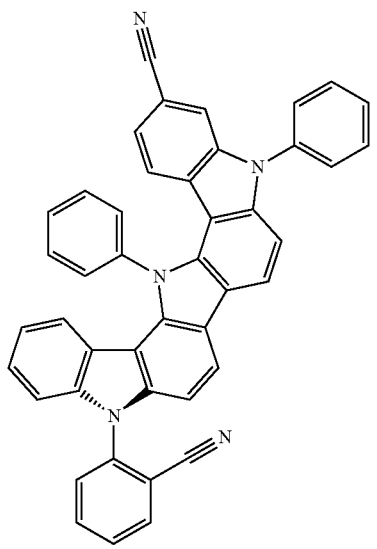
40
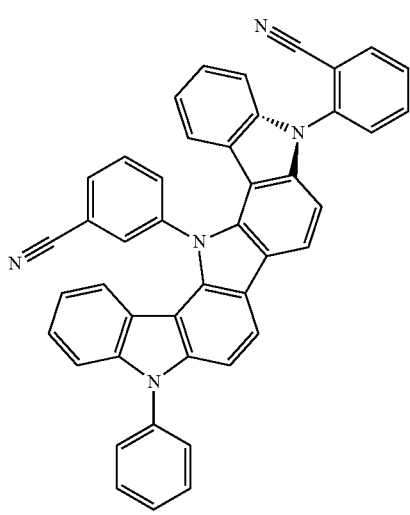
41
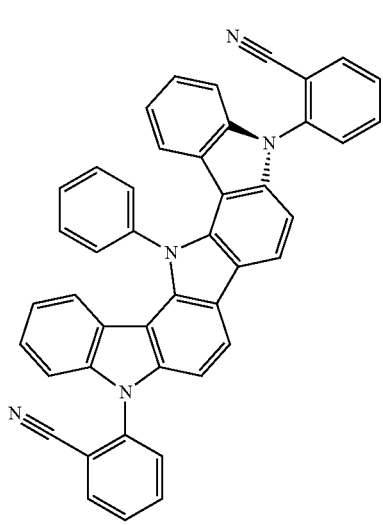
42
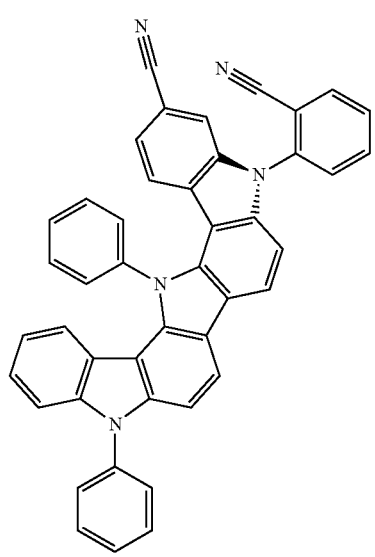
43
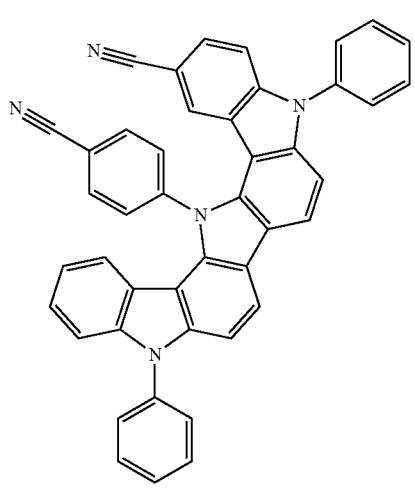
44
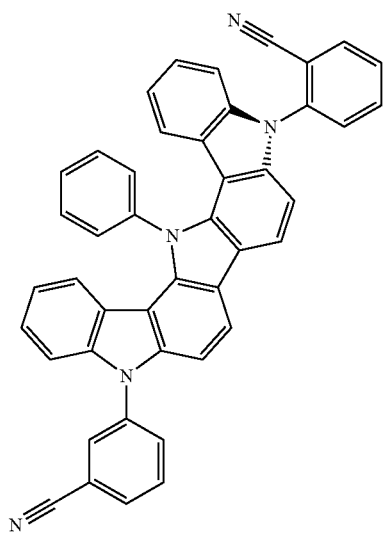

| 45 | 48 |
|---|---|
| 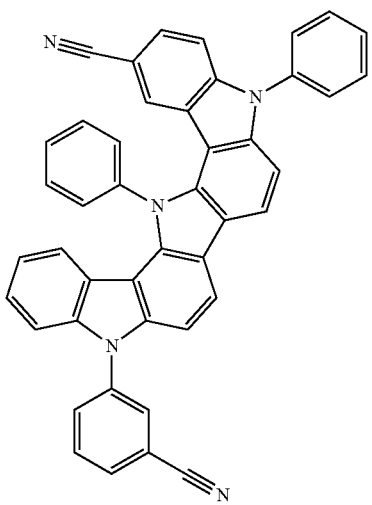 | 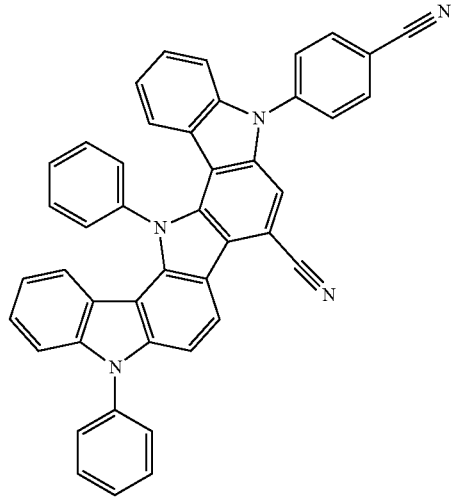 |
| 46 | 49 |
| 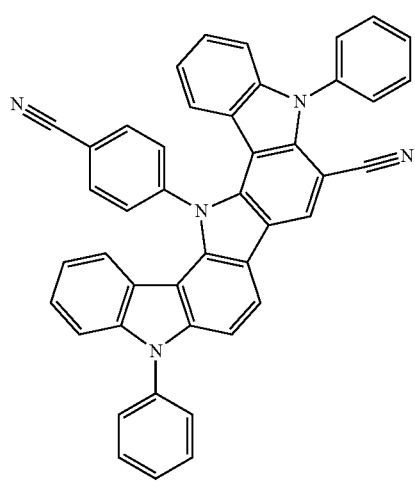 | 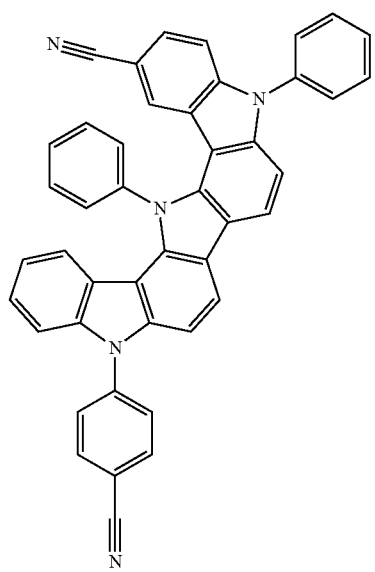 |
| 47 | 50 |
| 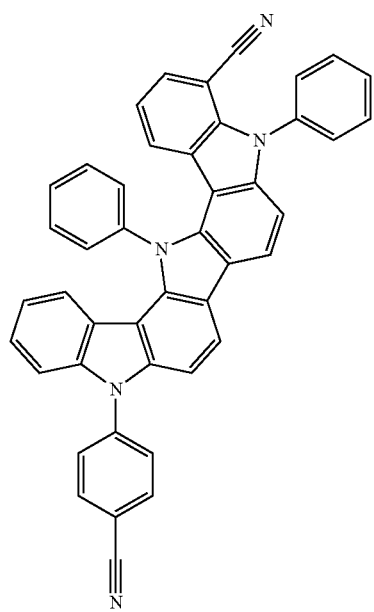 | 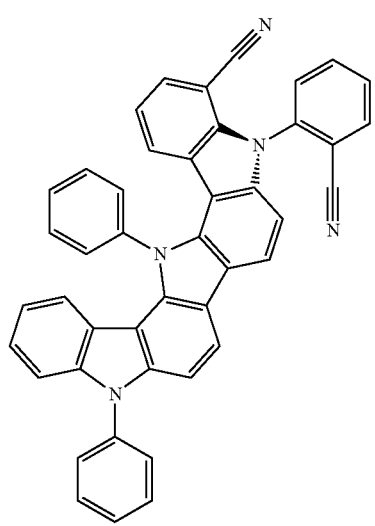 |

-continued
51
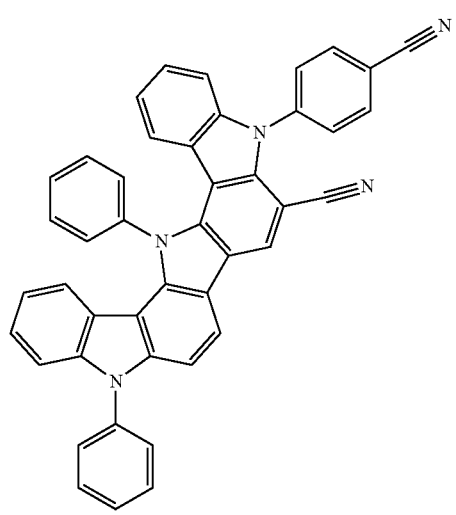
52
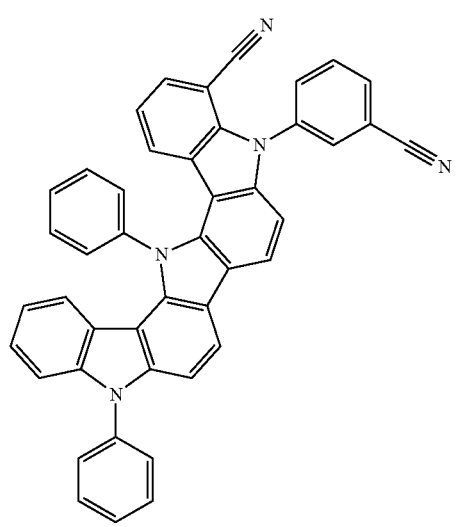
53
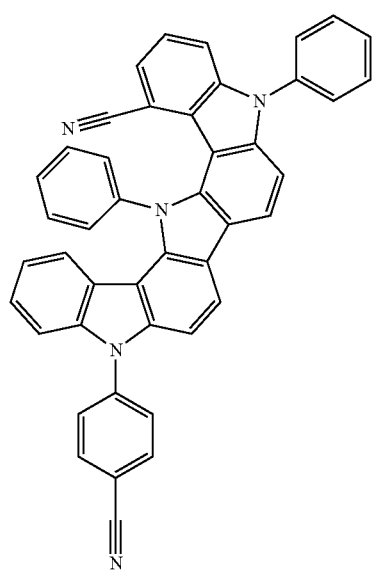
-continued
54
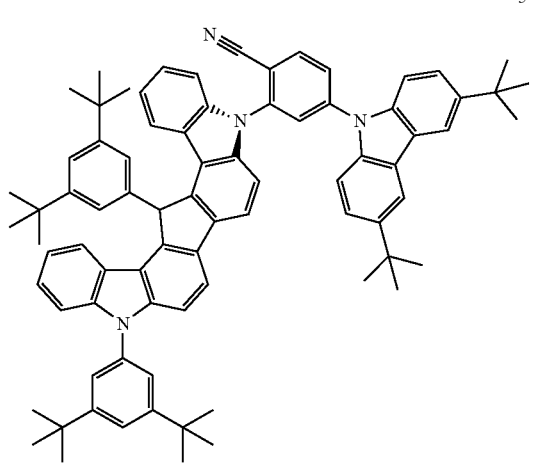
55
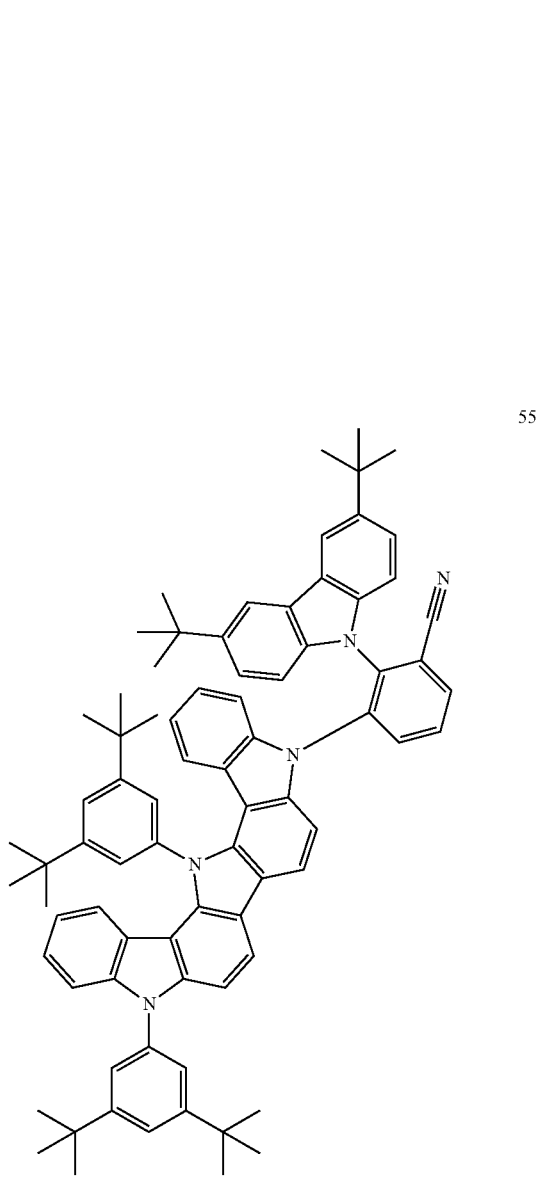

56
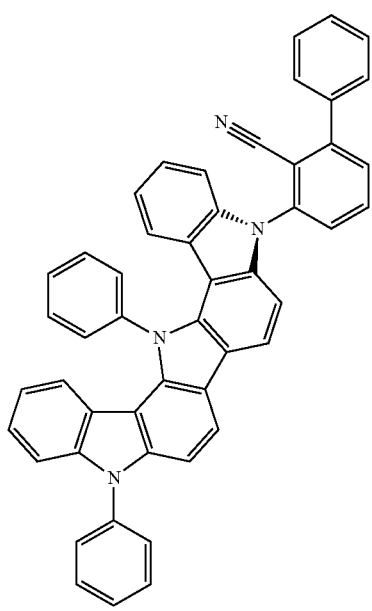
57
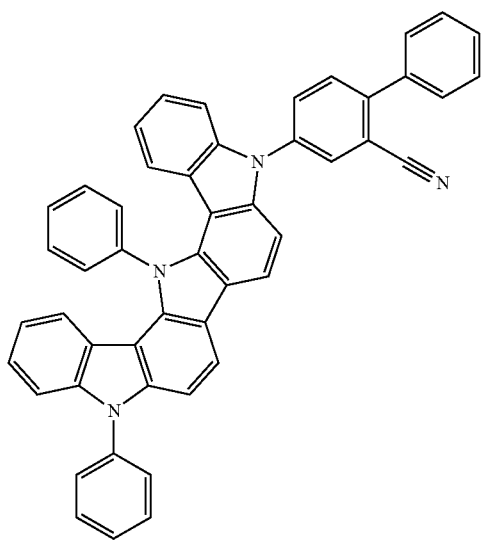
58
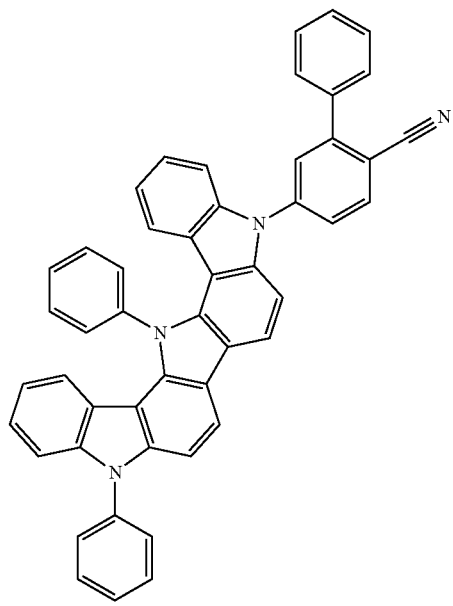
59
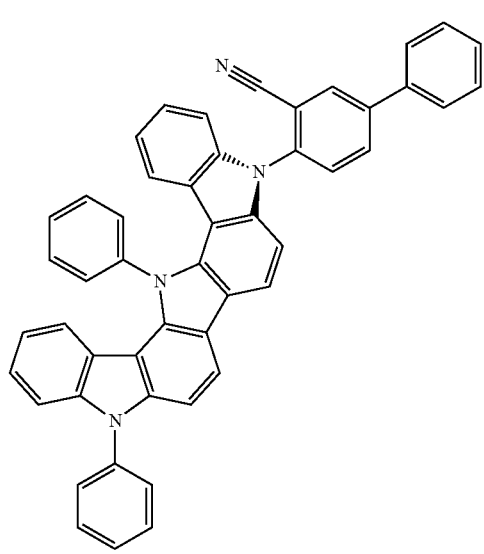

60
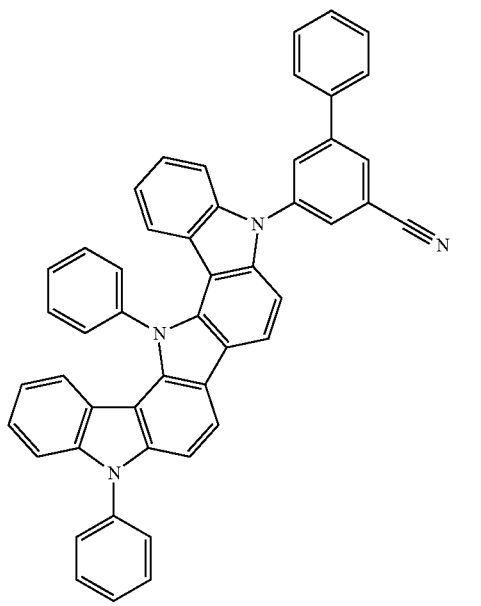
61
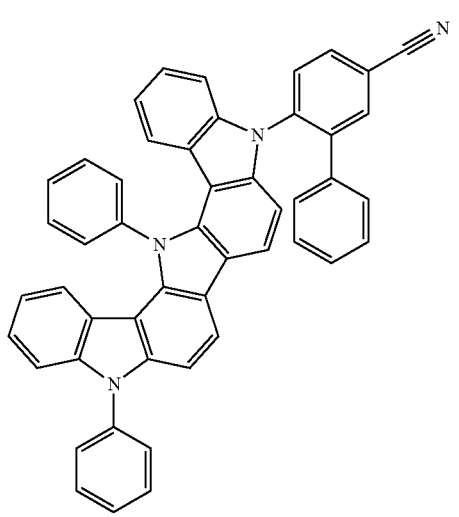
62
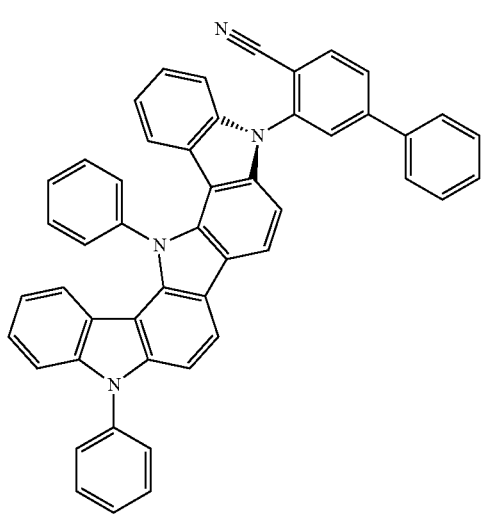
63
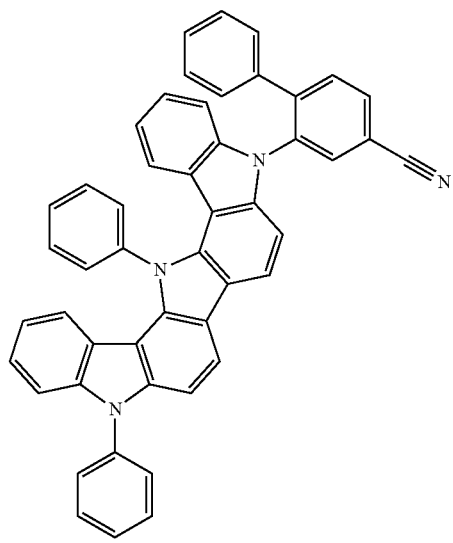
64
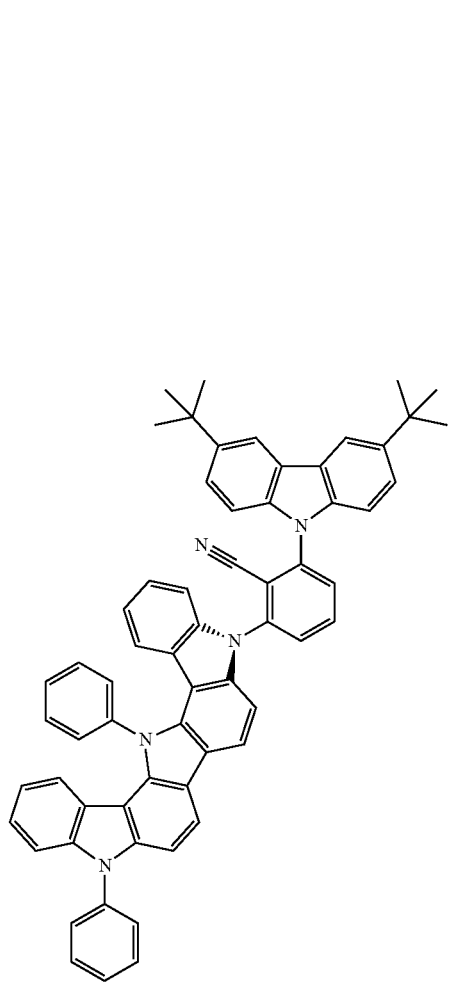

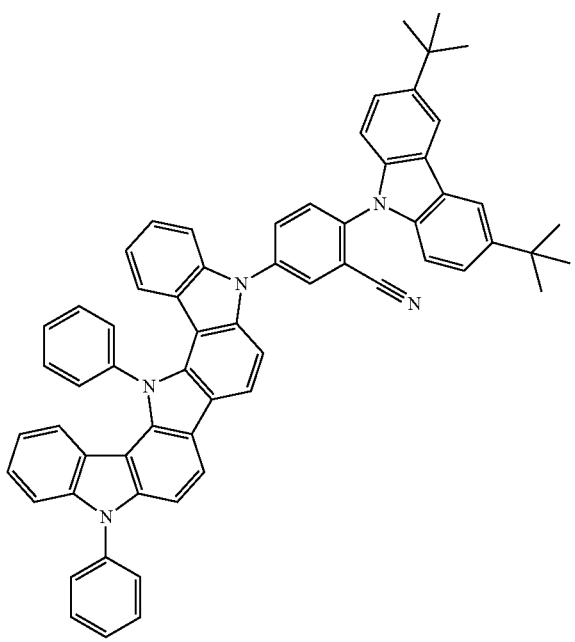
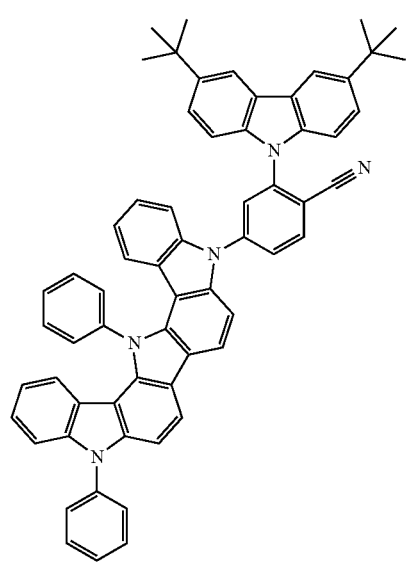
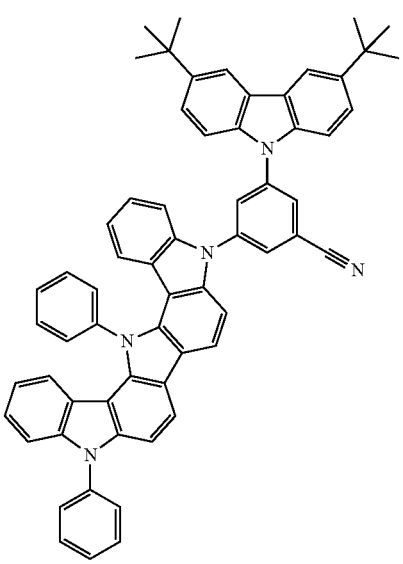

69
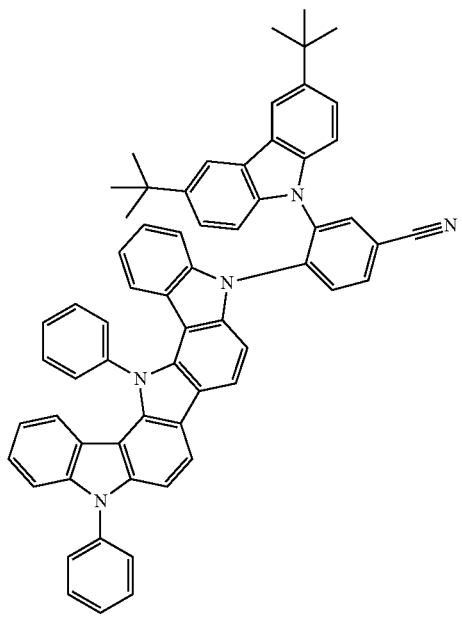
70
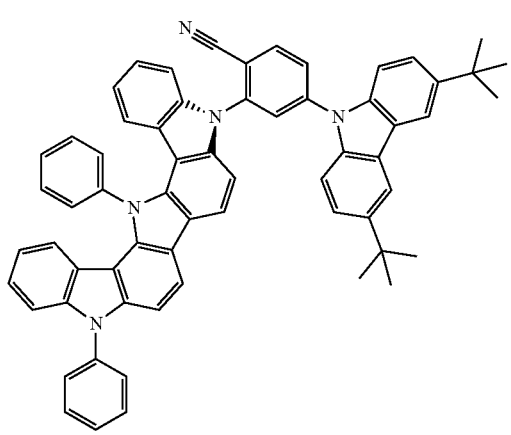
71
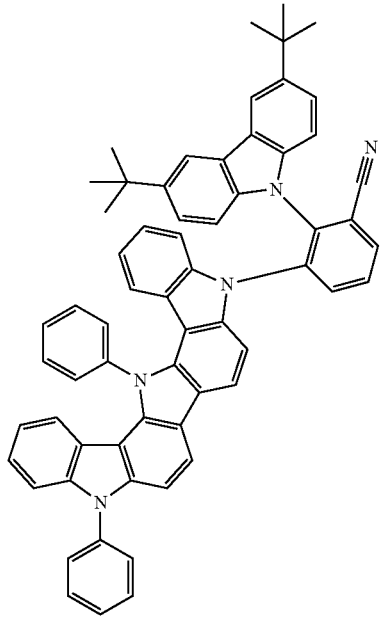
72
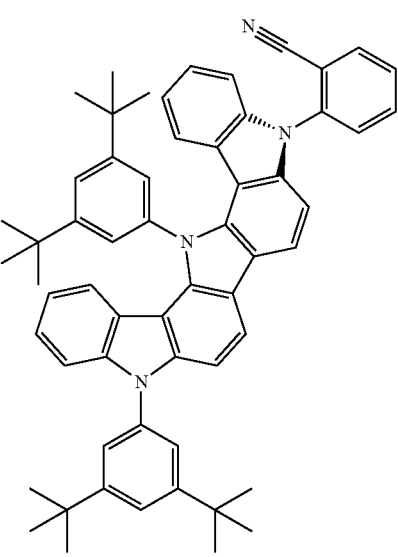
73
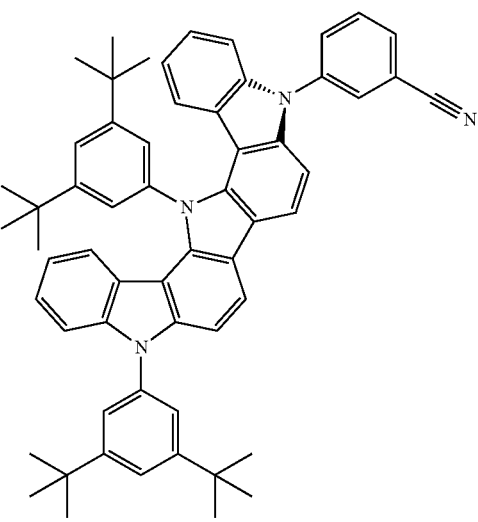
74
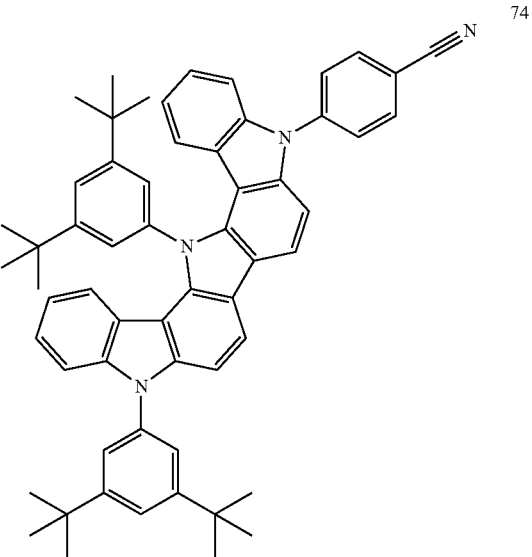

187
188
-continued
-continued
75
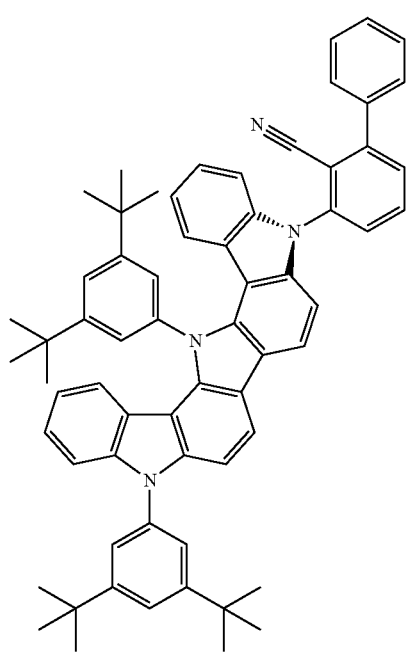
77
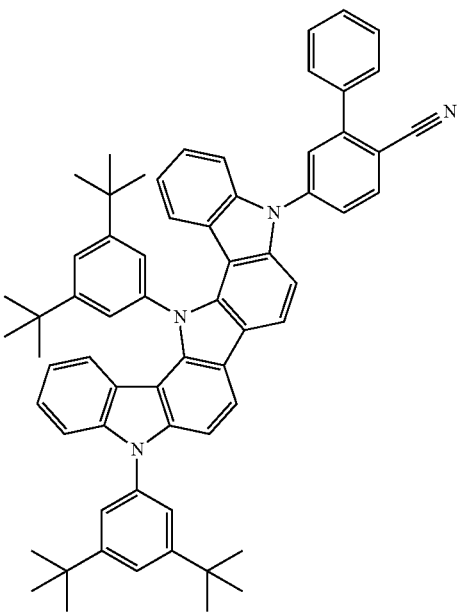
76
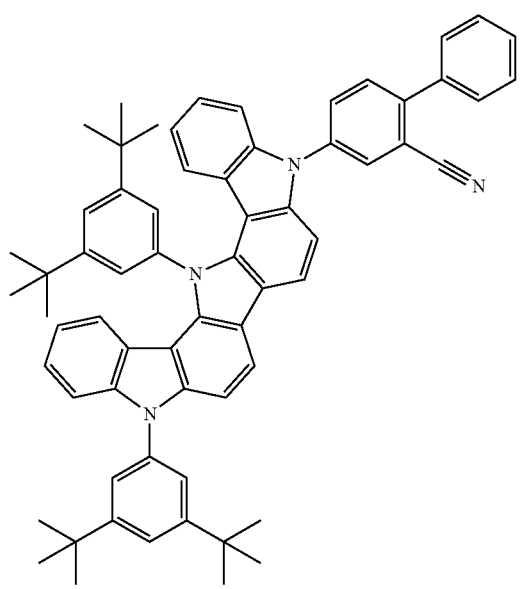
78
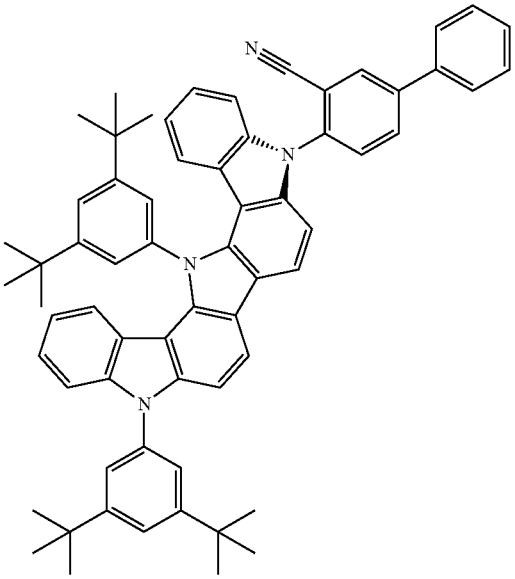

189
-continued
79
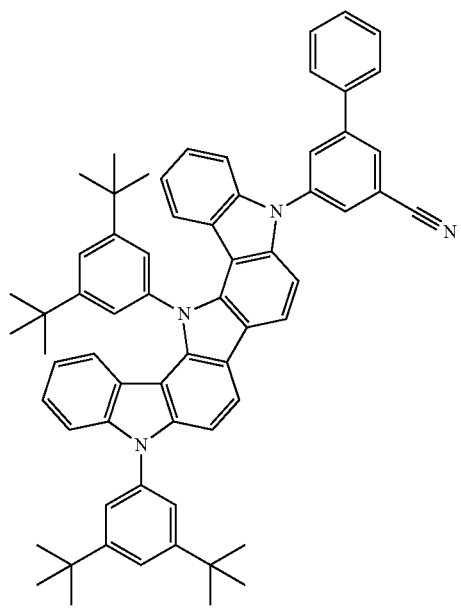
80
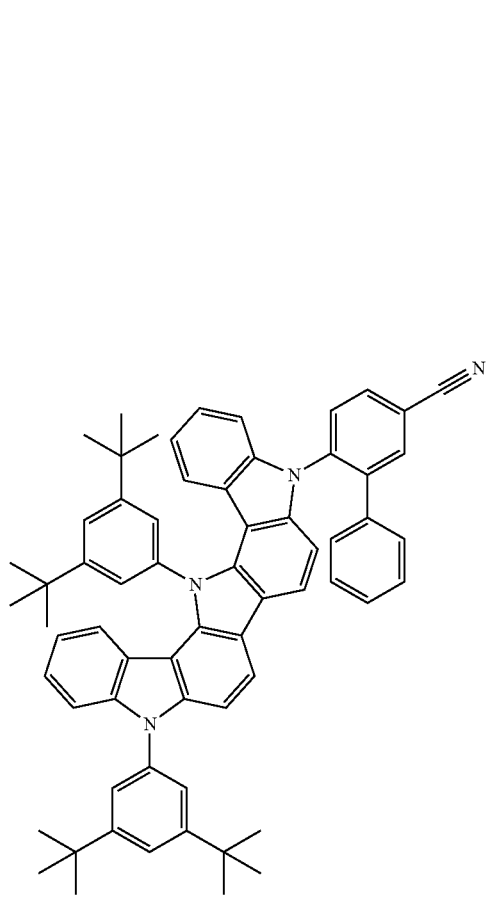
190
-continued
81
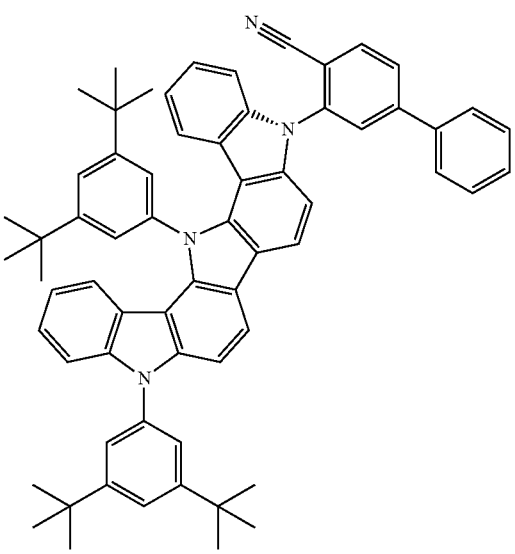
82
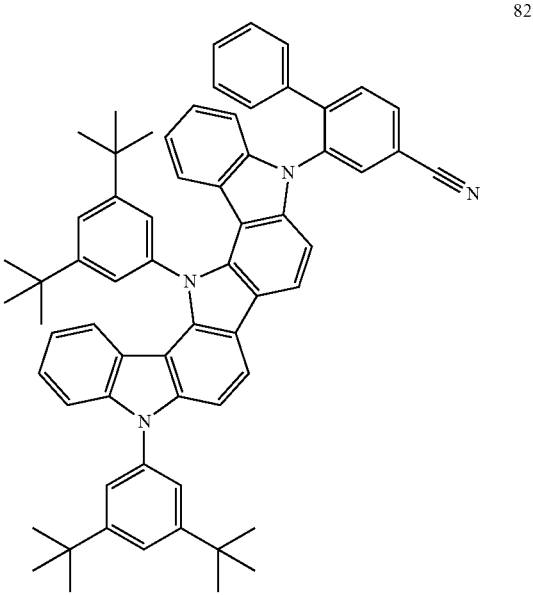

83
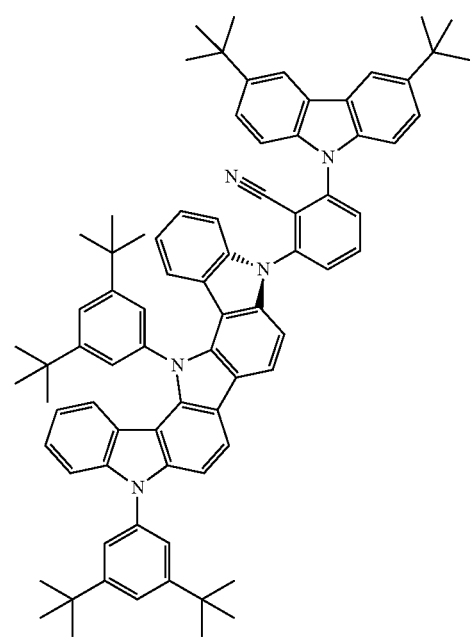
84
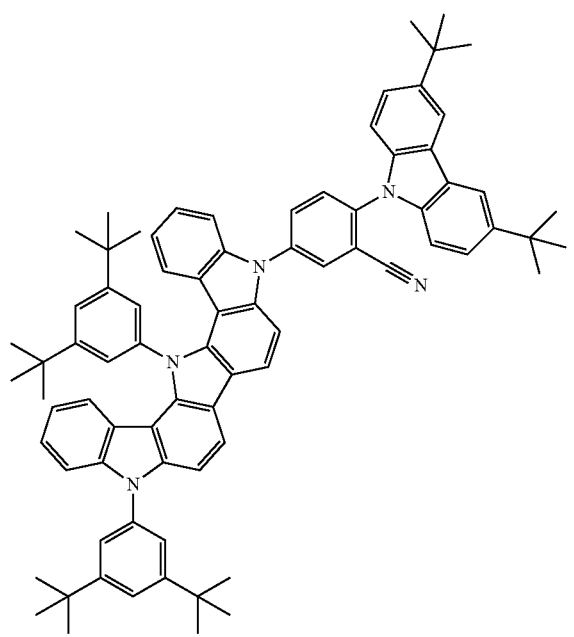
85
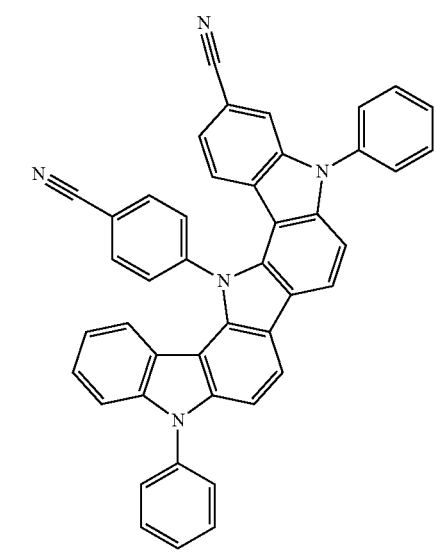
86
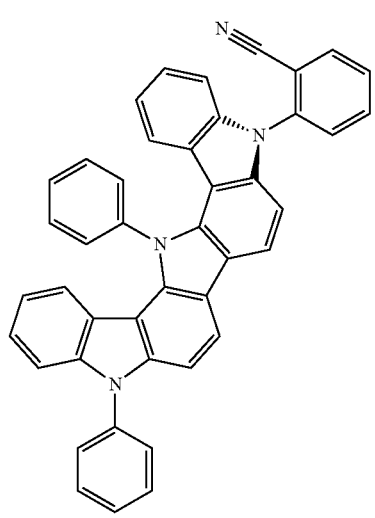
87
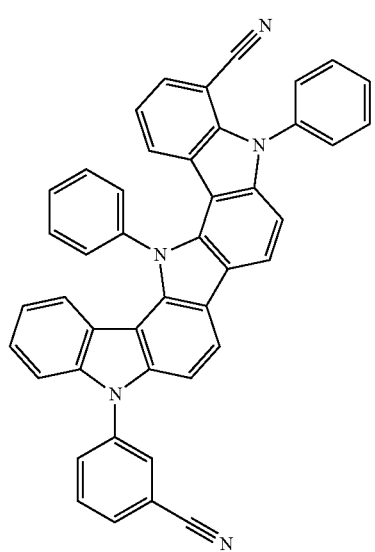

88
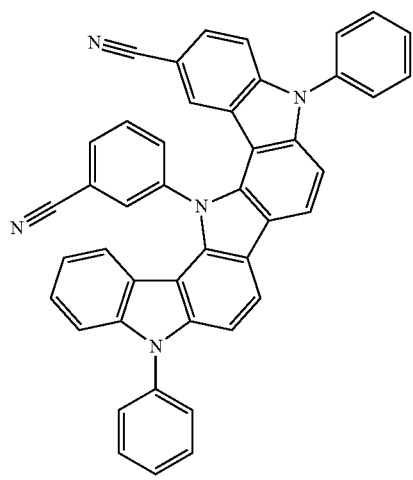
89
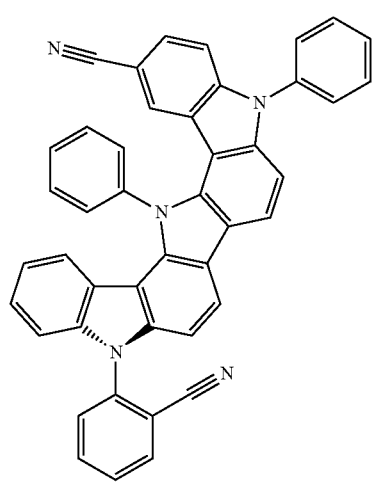
90
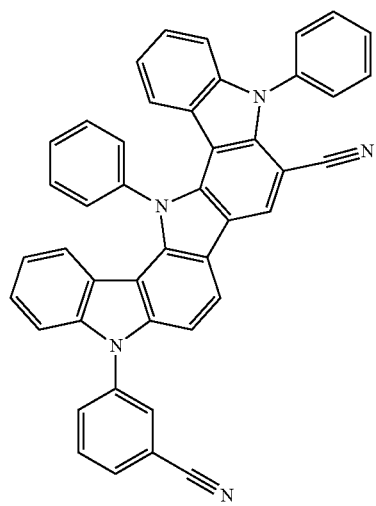
91
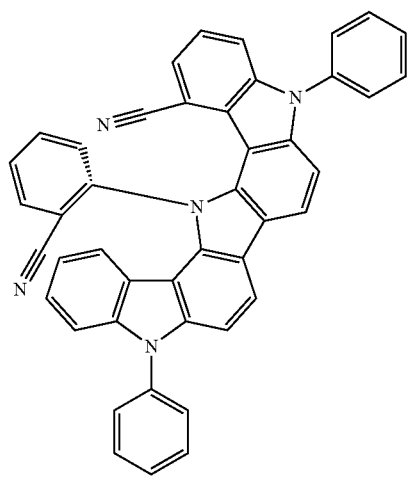
92
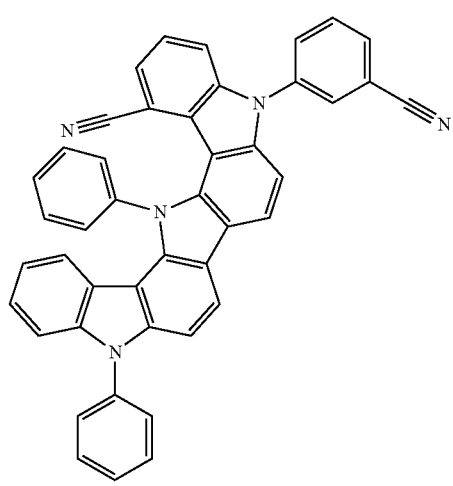
93
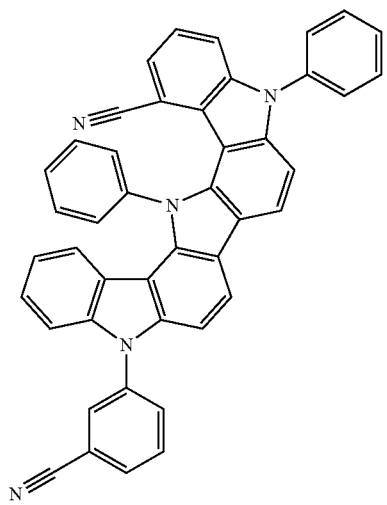

-continued
94
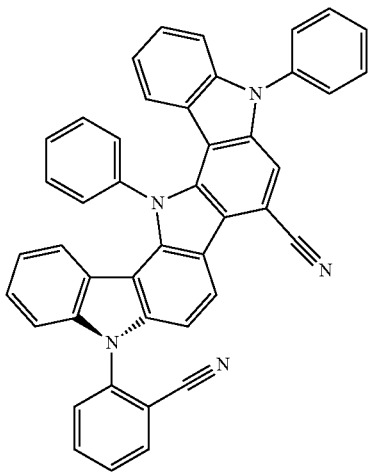
95
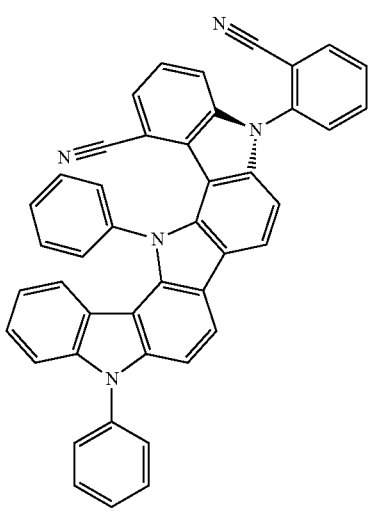
96
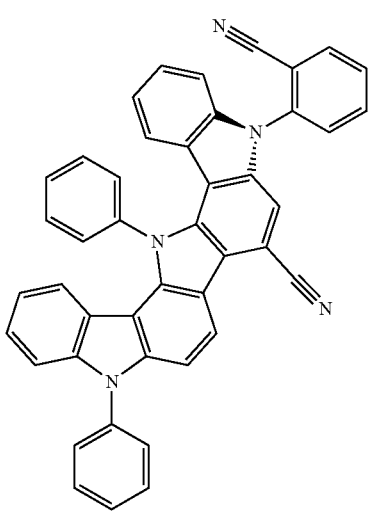
-continued
97
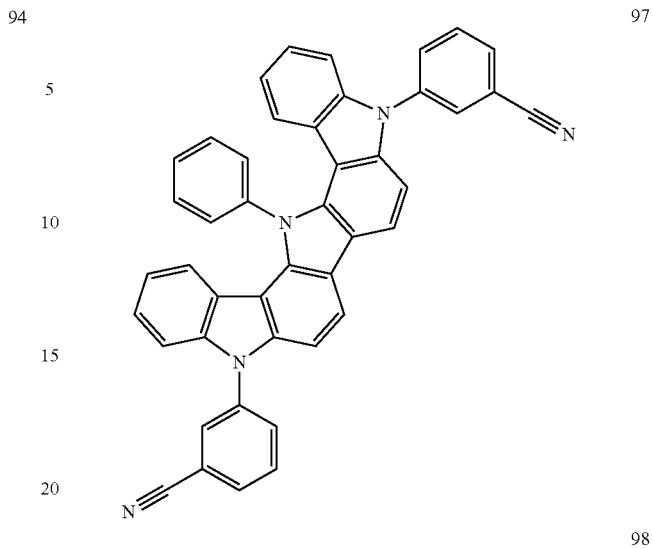
98
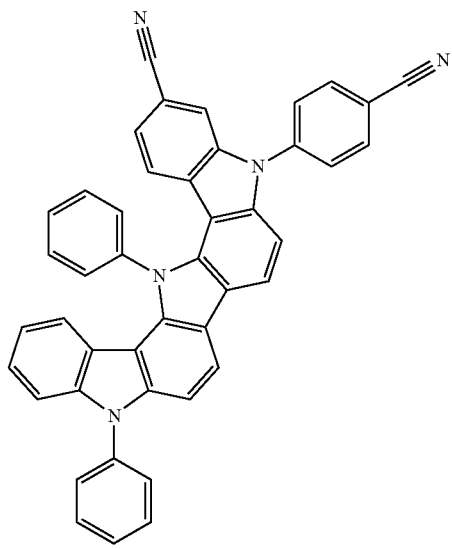
99
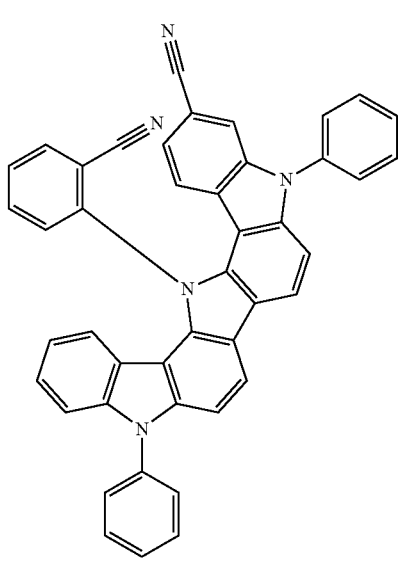

100
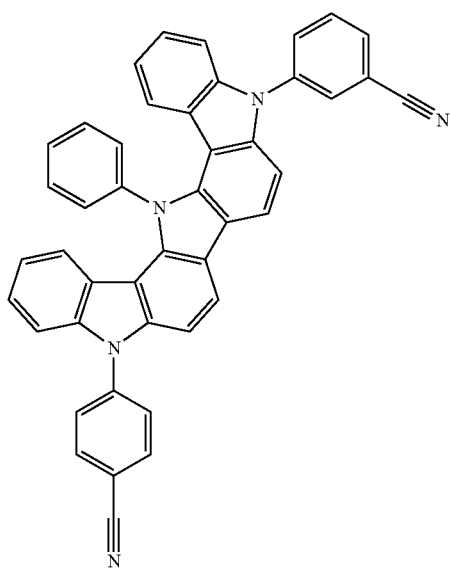
101
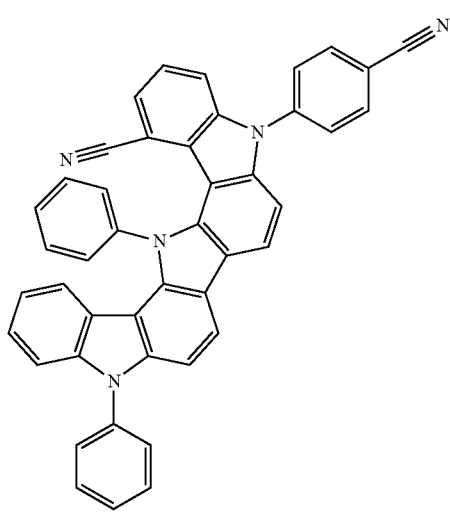
102
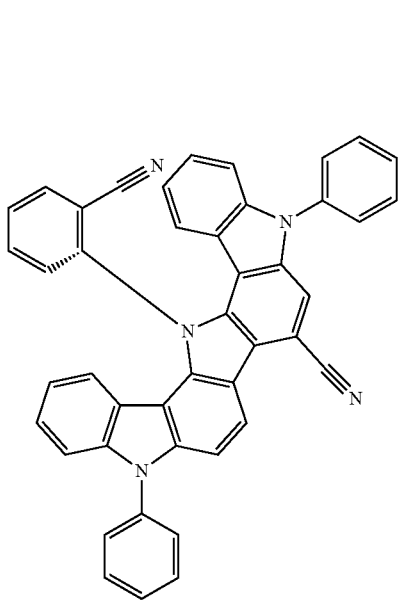
103
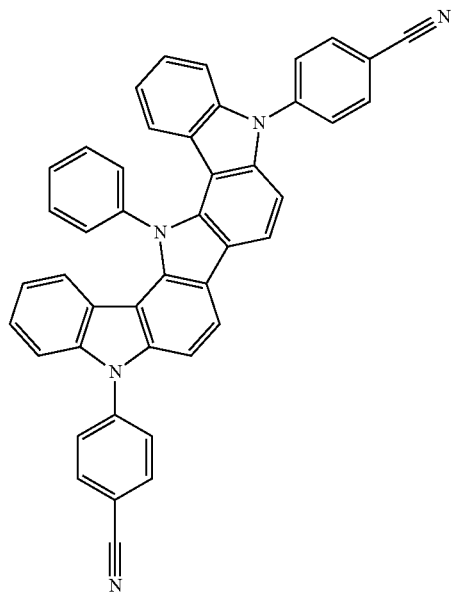
104
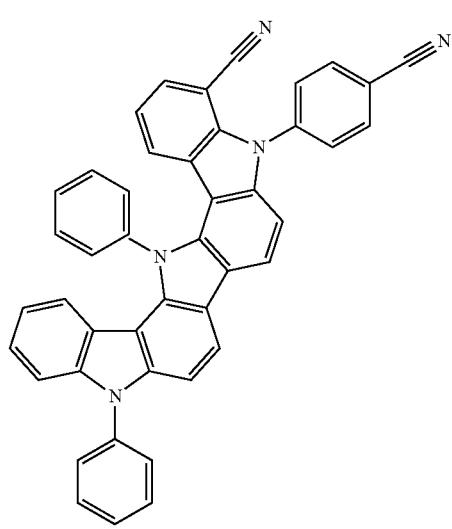
105
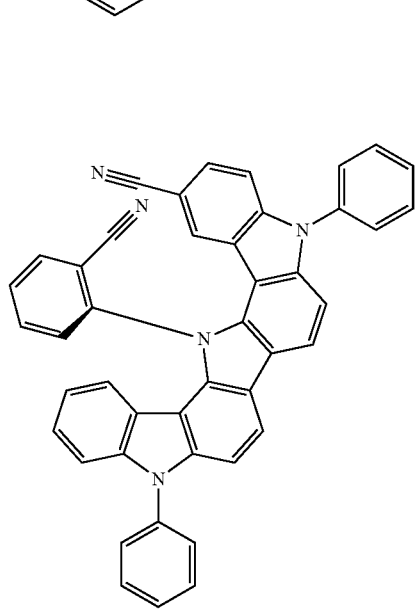

106
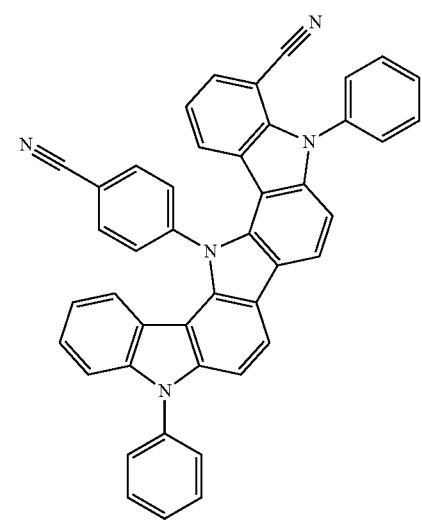
107
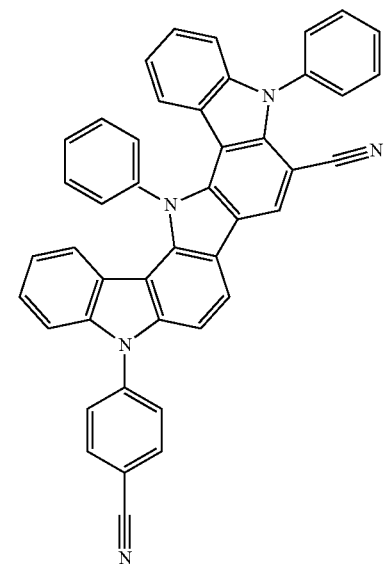
108
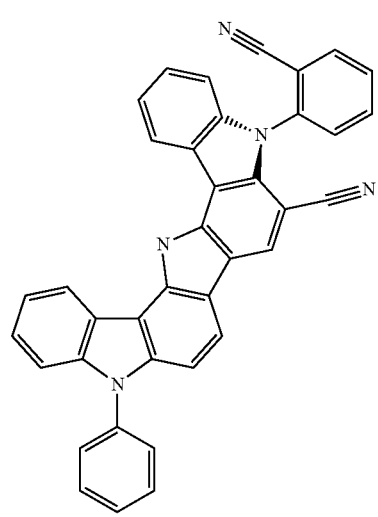
109
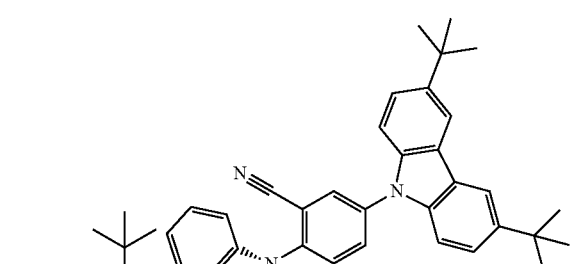
110
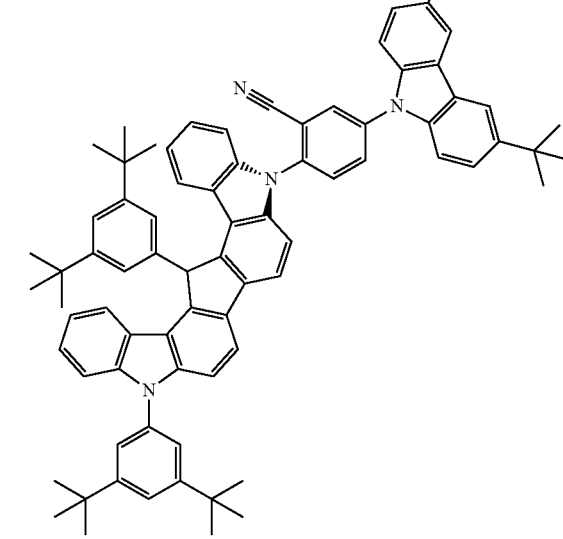

-continued

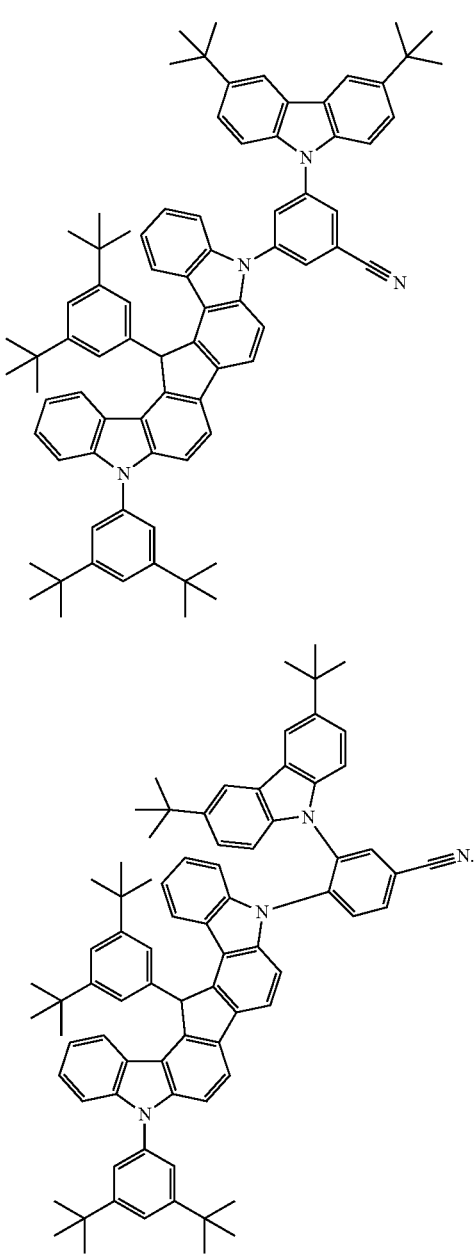

13. An organic light-emitting device comprising:
a first electrode;
a second electrode; and
an organic layer disposed between the first electrode and the second electrode and comprising an emission layer,
wherein the organic layer comprises at least one of the condensed cyclic compound represented by Formula 1 in claim 1.

14. The organic light-emitting device of claim 13, wherein
the first electrode is an anode,
the second electrode is a cathode,
the organic layer comprises a hole transport region disposed between the first electrode and the emission layer and an electron transport region disposed between the emission layer and the second electrode,
the hole transport region comprises at least one layer selected from a hole injection layer, a hole transport layer, and an electron blocking layer, and
the electron transport region comprises at least one layer selected from a hole blocking layer, an electron transport layer, and an electron injection layer.

15. The organic light-emitting device of claim 13, wherein the emission layer comprises the condensed cyclic compound represented by Formula 1.

16. The organic light-emitting device of claim 15, wherein the condensed cyclic compound comprised in the emission layer is a fluorescent emitter, and
a percentage of light-emitting components emitted from the condensed cyclic compound among the total light-emitting components emitted from the emission layer is about 80% or more.

17. The organic light-emitting device of claim 16, wherein the emission layer consists of the condensed cyclic compound; or
the emission layer further comprises a host.

18. The organic light-emitting device of claim 15, wherein the emission layer comprises a host and a fluorescent dopant,
the host comprises the condensed cyclic compound,
an amount of the host is larger than an amount of the fluorescent dopant, and
a percentage of light-emitting components of the fluorescent dopant among the total light-emitting components emitted from the emission layer is about 80% or more.

19. The organic light-emitting device of claim 15, wherein the emission layer comprises a host, an auxiliary dopant, and a fluorescent dopant,
the auxiliary dopant comprises the condensed cyclic compound, and
the emission layer satisfies Equations 3 and 4:

$$E_{T1(HOST)} - E_{T1(AD)} > 0.05 \text{ eV} \qquad \text{Equation 3}$$

$$E_{S1(FD)} - E_{S1(AD)} < 0 \text{ eV}, \qquad \text{Equation 4}$$

wherein, in Equation 3, $E_{T1(HOST)}$ is triplet energy (eV) of the host, and $E_{T1(AD)}$ is triplet energy (eV) of the auxiliary dopant,
in Equation 4, $E_{S1(FD)}$ is singlet energy (eV) of the fluorescent dopant, and $E_{S1(AD)}$ is singlet energy (eV) of the auxiliary dopant, and
$E_{T1(HOST)}$, $E_{T1(AD)}$, and $E_{S1(FD)}$ are evaluated by using a DFT method of Gaussian program structurally optimized at a level of B3LYP/6-31G(d,p).

* * * * *